(12) United States Patent
Noguchi et al.

(10) Patent No.: US 9,422,346 B2
(45) Date of Patent: Aug. 23, 2016

(54) TOBACCO ENZYMES FOR REGULATING CONTENT OF PLANT METABOLITES, AND USES THEREOF

(75) Inventors: Soichiro Noguchi, Tokyo (JP); Shoichi Suzuki, Tokyo (JP); Masao Arai, Tokyo (JP); Kaori Hamano, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 900 days.

(21) Appl. No.: 13/586,335

(22) Filed: Aug. 15, 2012

(65) Prior Publication Data

US 2013/0056014 A1 Mar. 7, 2013

Related U.S. Application Data

(63) Continuation of application No. PCT/JP2011/053297, filed on Feb. 16, 2011.

(30) Foreign Application Priority Data

Feb. 17, 2010 (JP) .................................. 2010-032537

(51) Int. Cl.
| | |
|---|---|
| C12N 15/82 | (2006.01) |
| A24B 13/00 | (2006.01) |
| A01H 5/00 | (2006.01) |
| C12N 15/63 | (2006.01) |
| C07K 14/415 | (2006.01) |
| A24B 15/10 | (2006.01) |

(52) U.S. Cl.
CPC ............... *C07K 14/415* (2013.01); *A24B 15/10* (2013.01); *C12N 15/8243* (2013.01); *C12N 15/8271* (2013.01); *C12N 15/8279* (2013.01); *C12N 15/8286* (2013.01)

(58) Field of Classification Search
None
See application file for complete search history.

(56) References Cited

U.S. PATENT DOCUMENTS

| | | | | |
|---|---|---|---|---|
| 5,260,205 | A * | 11/1993 | Nakatani et al. | 435/193 |
| 5,959,187 | A | 9/1999 | Bailey et al. | |
| 7,605,308 | B2 | 10/2009 | Conkling et al. | |
| 2003/0018997 | A1 | 1/2003 | Conkling et al. | |
| 2004/0103454 | A1 | 5/2004 | Conkling et al. | |
| 2006/0041962 | A1 | 2/2006 | Inze et al. | |
| 2006/0057723 | A1 | 3/2006 | Conkling et al. | |
| 2006/0107345 | A1* | 5/2006 | Alexandrov et al. | 800/278 |
| 2006/0191039 | A1 | 8/2006 | Conkling et al. | |
| 2006/0195936 | A1 | 8/2006 | Conkling et al. | |
| 2006/0236434 | A1 | 10/2006 | Conkling et al. | |
| 2006/0242730 | A1 | 10/2006 | Conkling et al. | |
| 2007/0016975 | A1 | 1/2007 | Conkling et al. | |
| 2007/0240728 | A1 | 10/2007 | Hashimoto et al. | |
| 2008/0120737 | A1 | 5/2008 | Hashimoto et al. | |
| 2008/0292735 | A1 | 11/2008 | Hashimoto et al. | |
| 2009/0210958 | A1 | 8/2009 | Page et al. | |
| 2010/0192244 | A1 | 7/2010 | Page et al. | |

FOREIGN PATENT DOCUMENTS

| | | |
|---|---|---|
| EP | 1586645 A2 | 10/2005 |
| JP | 2004-507250 A | 3/2004 |
| WO | WO 98/12913 A1 | 4/1998 |
| WO | WO 03/097790 A2 | 11/2003 |
| WO | WO 2006/109197 A2 | 10/2006 |
| WO | WO 2007/072224 A2 | 6/2007 |
| WO | WO 2009/063312 A2 | 5/2009 |

OTHER PUBLICATIONS

Maniatis et al., 1982, Molecular Cloning: A Laboratory Manual, Cold Spring Harbor Laboratory, pp. 324-343 and 387-389.*
Keskin et al., 2004, Protein Science 13: 1043-1055.*
Guo et al., 2004, Proceedings of the National Academy of Sciences USA 101: 9205-9210.*
Thornton et al., 2000, Nature Structural Biology, structural genomic supplement, Nov. 2000: 991-994.*
Oksman-Caldentey and Saito, 2005, Current Opinion in Biotechnology 16: 174-179.*
Wang et al., 2000, Plant Science 158: 19-32.*
Nicotiana tabacum PR48, GenBank Accession No. AF154657.1.*
Howell, 1982, Annu. Rev. Plant Physiol. 33: 609-650.*
Nicotiana tomentosiformis quinolinate synthase_GenBank XM_009612598.1.*
Baldwin et al., "Quantification, correlations and manipulations of wound-induced changes in jasmonic acid and nicotine in Nicotiana sylvestris", Planta (1997), vol. 201, pp. 397-404.
Chintapakorn et al., "Antisense-mediated reduction in ADC activity causes minor alterations in the alkaloid profile of cultured hairy roots and regenerated transgenic plants of Nicotiana tabacum", Phytochemistry, vol. 68 (2007), pp. 2465-2479.
Goossens et al., "A functional genomics approach toward the understanding of secondary metabolism in plant cells", PNAS, Jul. 8, 2003, vol. 100, No. 14, pp. 8595-8600.
Häkkinen et al., "Functional characterisation of genes involved in pyridine alkaloid biosynthesis in tobacco", Phytochemistry, vol. 68 (2007), pp. 2773-2785.
Kahl et al., "Herbivore-induced ethylene suppresses a direct defense but not a putative indirect defense against an adapted herbivore", Planta (2000), vol. 210, pp. 336-342.
Kazan et al., "Jasmonate Signaling: Toward an Integrated View", Plant Physiology, Apr. 2008, vol. 146, pp. 1459-1468.
Leffingwell, "8A Basic Chemical Constituents of Tobacco Leaf and Differences among Tobacco Types", Tobacco Production, Chemistry and Technology, Chapter 8, Leaf Chemistry, Blackwell Science Ltd, pp. 265-284 (1999).

(Continued)

*Primary Examiner* — David T Fox
*Assistant Examiner* — Bratislav Stankovic
(74) *Attorney, Agent, or Firm* — Birch, Stewart, Kolasch & Birch, LLP

(57) ABSTRACT

The present invention provides a polynucleotide having a function of regulating a content of a plant metabolite, a polypeptide having a function of regulating a content of a plant metabolite, a vector containing the polynucleotide or a part of the polynucleotide, and a transformed plant produced by using the vector, and a method for producing the transformed plant, and according to the above polynucleotide, polypeptide, vector, transformed plant and method, a novel gene regulating a content of a plant metabolite and use of the novel gene.

9 Claims, 2 Drawing Sheets

(56) References Cited

OTHER PUBLICATIONS

Sato et al., "Metabolic engineering of plant alkaloid biosynthesis", PNAS, Jan. 2, 2001, vol. 98, No. 1, pp. 367-372.
Shoji et al., "Ethylene Suppresses Jasmonate-Induced Gene Expression in Nicotine Bio-synthesis", Plant Cell Physiology, vol. 41, No. 9, pp. 1072-1076 (2000).
Shoji et al., "Jasmonate-Induced Nicotine Formation in Tobacco is Mediated by Tobacco COI1 and JAZ Genes", Plants and Cell Physiology, vol. 49, No. 7, pp. 1003-1012 (2008).
Wang et al., "Comparisons of LIPOXYGENASE3- and JASMONATE-RESISTANT4/6—Silenced Plants Reveal That Jasmonic Acid and Jasmonic Acid-Amino Acid Conjugates Play Different Roles . . . ", Plant Physiology, Mar. 2008, vol. 146, pp. 904-915.
Xie et al., "Biotechnology: A tool for reduced-risk tobacco products—the nicotine experience from test tube to cigarette pack", Recent Advances in Tobacco Science, vol. 30, pp. 17-37, Sep. 19-22, 2004.
Yasumatsu, "Studies on the Chemical Regulation of Alkaloid Biosynthesis in Tobacco Plants", Agr. Biol. Chem., vol. 31, No. 12, pp. 1441-1447 (1967).
Extended European Search Report dated Jul. 26, 2013 for European Application No. 11744680.7.
Oksman-Caldentey et al., "Integrating genomics and metabolomics for engineering plant metabolic pathways," Current Opinion in Biotechnology, vol. 16, 2005, pp. 174-179, XP004849208.

* cited by examiner

SEQUENCE LISTING

```
<160> NUMBER OF SEQ ID NOS: 132

<210> SEQ ID NO 1
<211> LENGTH: 1946
<212> TYPE: DNA
<213> ORGANISM: Nicotiana tabacum

<400> SEQUENCE: 1
gaagaggtga aaattcacaa agaaagagag agagaataga ggagataagg tctacgacat      60
ggaagtggct ttcagaaaat ctattaatgg aggcttagtc aaagaggaga agaggaacaa     120
attagcttat caatccagtt ctgatgagga gggttttgtt gaagacagta atgttcttaa     180
ggtcgggaag gaaagagaag tccatgagga cgataattcg aagtatcctc agcaagagga     240
tatcgacagt gacaaggagg acgatcagct acaatcagtc aaagctgata tgaaagaggt     300
aatgaaagaa aatcagaggc tgaagatgca cttggatcga attatgaagg attatcggaa     360
ccttcagctg caatttcacg acattgttca aagaaatgct gaaaaatcca atagtattat     420
tgatactgat cggcataatg aatgtaacga agctgaattt gtctccctta gcttaggaag     480
atcttcaagc gacactaaaa aagaagagta cttatccaaa atcttgagca aagataaggc     540
agaggaagag aataaaggag gcctaaccct aggactggat tgcaagtttg atttgtgtgt     600
gaaaacaaca ccgacagaat tttcaactgc aaatctcagt gaagagaata ggtcagagga     660
agttaaggac gaaaatggag aaacattgcc accccataaa attctcaaga caatgagaaa     720
tggagaagat gatacacaac caaacccttc taaaagagca aaggtttctg ttagagtcag     780
atgtgatgcc ccgacgatga atgatggatg ccaatggaga aaatatggac aaaaaattgc     840
aaaaggaaat ccgtgtcctc gagcttacta ccgttgcaca gtagcaccct cctgcccagt     900
gagaaagcag gttcagagat gcattgagga tatgtcaatc ttgatcacta catatgaggg     960
aacacacaat catccacttt ctctttcagc aacatcaatg gcttccacaa cttcagcagc    1020
tgcttctatg ctattatctg gttcatcgtc cagctctgaa tcaggcccca atccaccagc    1080
aactgacgcc acgaatatca atggactcaa cttctatctc tccgatagct caaaaccaaa    1140 accatttac cttcaaaatt cgtccatctc ttcttcatcc tcgcccccta caatcactct    1200
tgatttaacc tcaagctcgt tcacttcctt atttccccat cataacagaa tgagtagtaa    1260
```

```
ttatctcccc agatataatt cttccacaaa tattctcaac ttcagttcct tggaatctaa    1320
tcctcttctt cccatgtctt ggagtaatgg ggcctataac aagaaccaag aaattagttc    1380
tctcaacttt gcaaggcggc cacaagatat tcttttccaa tcttatctac aaaataatat    1440
tagtgcaaag cctacacaat ctttattacc acaagataca attgcagctg ctacaaaagc    1500
aataacatcc gacccaaatt ttcaatctgc attggctgtt gctcttgcat ctatcattgg    1560
ctcaggcagc ggaaatcatg caggtggtat tgaagaaaaa tctggtctaa atttgaaggt    1620
taccgaacca tttccagttc tttgcagctt cccatctacc tcaagaaat  aatatatcca    1680 attaactgtt cttcaaattt ttctgaataa atcgacttct acggcaaata gacaggctgc    1740
tagtaacttt cgcttgctga agtaagaaac taattgcggc gttaattaat cagatgtaat    1800
atttttttta tgatttggag gtacgatgtc caaagtgtag atattttagt ttgataaaac    1860
taattgacac ttcgcttact gaagtcattg ctttagcctt tacattgttt tttcgttaag    1920
tgttagttaa atgtgatttt aacaaa                                        1946

<210> SEQ ID NO 2
<211> LENGTH: 2598
<212> TYPE: DNA
<213> ORGANISM: Nicotiana tabacum

<400> SEQUENCE: 2
ggactttgca agaaaataga gaaaacagct tctctcattt cgtttcccaa aaaactacca     60
atatttcttt attggggcaa aactatagta ttttcccagt tgaattctag ttctattaca    120
gaacctcagt ttcttccaga gctcaaaagt ttgcttggtc accttcttga ctgcaaagat    180
accggtgtgt attttttcatg ctttttttacc aatcttcttt gtttgtccat ttatgcattt    240
ttatgtccaa gtttgtatcc tttctgggta ttttttttata gttacttata ccctctagtt    300
tccaagcttt tgagatctga aaagtagagg tatggacaat tgggtgttca ataagaagaa    360
gaagatcaat tgttttttctt gaagttacga tgagtttgct ttagattggt taattggtgt    420
tctagaatgt gttaaaggtt caagctttgg aggagaaaaa aaaagaattg tcttttttcag    480 ttcttgtttc atctaggaat ataaatttgg aatctctttt gggtcctagg ggtgttttgt    540
agttcaaggg attttttttta ctaggtagag atgggtacgg tgaatatgtc gtggagtgat    600
gaggataagg caacagtggc ggctgtactg gaaaagaag cttttgaata tttgatatct    660
agctcggttt cagcagaatg ttctttaatg gcaatagga  atgatcagaa tttgcagaat    720 aagcttttcag atctcgtgga acgcccgaac gccactaatt ttagctggaa ttatgccatc    780
ttttggcaaa tttcacggtc taaatcgggg gaattggtgc tagggtgggg cgatgggtgt    840
tgcagagaac ctagggaagg agaggagcgt gaagttaaaa gtatatttaa tctacgcctt    900
gaggatgagg ctccacaaag gatgaggaaa agggtccttc agaagttgca tatgttattt    960
ggtggaacag atgaagataa ctatgctatt ggattggata gggtcactga tactgaaata   1020
ttcttccttg cctcgatgta cttttcgttc cctcgaggag agggaggtcc agggaagtgt   1080
tttggttcgg gtaagcattt gtggttatca gatgcattga agtcccctct agattattgt   1140
gctagatctt tcctagctaa gtcagctggt atgcaaacta ttgttttgat cccaactgat   1200
gttggagttg tggaattggg atcagtgaga tcgataccgg aaagtttgga gctattgcat   1260
tctataaaat cttgcttctc ttcgtttctt gttagggcta agcaagcagc aggtttagca   1320
gttgtaacta gaaaaaaga tggaaataat tccccttttt cgagctcagc ttttagtgag   1380
cgaccagatg gaattcctaa gatttttggg cacgatttaa attccggtac ccactttagg   1440
```

-continued

```
gaaaaacttg ctgttaggaa agcggaggag agaccatggg atatttacca aaacggtacc    1500
aggatgccat tcatgaacgg gcgtactggt ttacatgctg cttcttgggc gcaattcagt    1560
aatgtgaagc cggtaaagcc agtggagctc tatagtcctc agacgccccc agcacacaac    1620
ctacaagagc ttgtcaatgg tggaagggaa gaattccgtt tgaacaactt tcagcatcaa    1680
aagcctgcta gaatgcaaat tgatttcact ggagcaacct cgagacccat tatttcgcca    1740
gcacacactg ttgagtctga gcattcagat gttgaagctt cgtgtaagga agactgtgca    1800
ggcccggttg atgaaaagag gcctagaaaa cgtggaagaa agccagccaa cggaagggaa    1860
gagcccctca atcatgtaga ggcggagagg cagcggcggg aaaagctgaa ccagcgattc    1920
tatgcattac gagctgttgt tccgaatatc tccaaaatgg acaaagcttc cctcttagga    1980
gatgccattg cttacataac tgagatgcag aaaaaactaa gagacatgga atccgagagg    2040
gagctgagat taggaagcac ttcaagggat gcaatggctg cagaagacag cccgaattca    2100
gagattcaaa tccgtggacc cgacatcaac gtagaagctg ccaatgatga agtcattgta    2160
agggtgagtt gtcctctgga aacccatcca atatcaagag tcatccaaac attcaaagat    2220
gcacagatca atgttgttga atcaaaactt tctgccggga atggaactgt atttcacaca    2280
tttgtactca agtctagtgg atctgaacag ctgacaaagg aaaagttgct ggctgcattt    2340
tccagcgaat cagactcgct gaggcaattt tcaccggtag gcaataaca gttttatgtt    2400 ttatgtagtt gctaggcata agtgtagtg aagaatcata tcgtagtttc tgcagagttt    2460
ttcgtataca tcagttcaag ataggtggaa ataactagct attgacaaag tagcagcaaa    2520
ttttctgtgt ttgtctatag tatacatgtt ttatcatgag gcatgatgga tcaattgcaa    2580
gcttaactat cttttgca                                                 2598
```

<210> SEQ ID NO 3
<211> LENGTH: 1235
<212> TYPE: DNA
<213> ORGANISM: Nicotiana tabacum

<400> SEQUENCE: 3

```
acgaggaata ttacaaaaag agttgaaaac agagggaga gatgggtaga ccaccttgtt      60
gtgataaaat aggggtgaag aaaggaccat ggactcctga agaagatatt atgttggtct     120
cttatgttca agaacatggt cctgggaatt ggagagcagt tcccactaat acagggttgc     180
gcagatgtag caagagctgc aggctaaggt ggactaatta cctcagaccg ggaattaaga     240
gaggcagttt cactgatcaa gaggagaaaa tgattatcca gcttcaggct ctcttaggca     300
acaaatgggc tgccatagct tcatatctcc cggagagaac agacaacgat gtcaaaaact     360
attggaatac tcatttaaag aaaaagttga aaaagctcga atcaagtgat ttatactcta     420
aagatggatc ttgtttatca ccatcaaact caacctcgag aggccagtgg aaaggacac      480 ttcaaactga tataaacaca gccaaacaag ctttacaaaa tgccctgtca ctggataagt     540
caagcccaat tcctgaatat acgaccactg atgtgaagcc tataaatctt ggctgttact     600
catacataaa acaagaagga aaagtgtcta cttctactta cgcatcaagt gctgaaaaca     660
tagccaaatt gcttaaacaa tggaccagaa gtgattcaac aaacatttct gagcaatcga     720
aagcttcatc aagtactcaa ctctcaagta ataacaatgc caccaccgag gaatttgagt     780 cacttttccag tttcgattca tttgaacagt caaattcaga tcaattttca cagagtttga     840
cacttgaggc tggtaaaatta cactgtgaaa ttagtaaaag agaagtggat gatcaagtac     900
```

| | |
|---|---:|
| ccttgtcagt aatgctggag agttggcttt tgatgaaaa tgacgatttg ctaatttaga | 960 |
| aggaattttt ttgcttttcc atttggggat tctatttgtt gcattatgtt tttgtttctt | 1020 |
| accccaagta ctagaatttt acctaggtat ggatgtgaca tccacattct tttttttttt | 1080 |
| tgggccaggt atgactgttt taacattagt gtatatttag cttattctta gaggaatttc | 1140 |
| gttcttttct aatatgataa gtgtctatca tttaacctcg tgtttcctaa gaatcgaaat | 1200 |
| atttattata ctaagattag tatgttgaat ccaaa | 1235 |

<210> SEQ ID NO 4
<211> LENGTH: 1185
<212> TYPE: DNA
<213> ORGANISM: Nicotiana tabacum

<400> SEQUENCE: 4

| | |
|---|---:|
| gaaagttgat agaattaata tcactcatca tatatatgga gtcccaatgg caagaaaact | 60 |
| cattgtctga tctgaaaatg ttaatcaaag agttgaattg cggccaagaa ttcacacaca | 120 |
| agctaagaga tgtgataaaa caatctctag taaatgagaa catgaatatg ttggctgaga | 180 |
| atttggtagg gcaaattatg ggttcatttt gtaagacttt gtcaatacta aacactagca | 240 |
| actccaatga agattctcag attccgatgg tggccgtttt ccttgtccg aaagacggac | 300 |
| ggacgtcgcc ggaagactca acgggcagtt gcaagaaatc atcagcaaaa gatcgaatag | 360 |
| gatgcaataa gaaaaggaaa atttcagcga aaccgttaa agaaacctca actttggcgg | 420 |
| atgacggaca tgtttggaga aaatatggcc aaaaacaaat tcttgatgcc ccttatccaa | 480 |
| ggcattatta tagatgtacc aacaaatttg atcaaggatg tgaagcaatt aaacaagtgc | 540 |
| aaagaattca agacaatcca ccacagtttc ggacaatata ccaaggtcat cacacatgta | 600 |
| caacttaccc cacagcttcc caaatactct tagattcttc aacagattat gaaaattctt | 660 |
| caatcctact cagttttaat accaaggata tcattatta ccatccttat aattttccca | 720 |
| cattttttttc aacaaaaaaa gaaactaaag aggaaaactc cccaagtttc ttctacccta | 780 |
| ataacaacca aaaccaaata tcaacttccg actatattct tccggccaat gattattgga | 840 |
| ctccggcaac tgaaacctcc ggcaatgtta tggcgacggc gttatcgtcg gcgtctgata | 900 |
| atgtggatta catctcatct gaatcagtta ctagcactca caatttggag atggagatgg | 960 |
| agatggagat ggagatgatg gcgggaattg actttgacga tttgcctttt gaattttaag | 1020 |
| ggtagatttt tctctcatat ttttttggga gtataggtag attcaggata agttcttgtg | 1080 |
| agttcaacta aattaattac tttcgggggtt ctaactatgt atacataagt ataagttaaa | 1140 |
| ataatatata gtgtatacat gtaataaaat tagacttatt ttaga | 1185 |

<210> SEQ ID NO 5
<211> LENGTH: 3592
<212> TYPE: DNA
<213> ORGANISM: Nicotiana tabacum

<400> SEQUENCE: 5

| | |
|---|---:|
| gtggaacaag aaatacatag agagagaaat agggagagag atacgaaaaa aaatacacac | 60 |
| acagatagag agaaaaattc cgaaaaatat ttaagctttc aaaataaaaa taaaactaaa | 120 |
| aaaaatctac tgctttcttt ctttgtttga aattagtatt aatggttgtt gtttcattta | 180 |
| aagcttaaag cttttgtttt tgggattact actccaccgg tctgttactg ggttgttact | 240 |
| gttgctgggc agttgttgct attgtactgt cattattgct gctgattctc atcatcattt | 300 |
| tcttttgctt ccaatatcag gtacatatct gaaaattcat gtcatgaaaa gcttcaacat | 360 |

```
ggcaagtaaa tgaagtttga ttataaggtt gttttctact catttaaatt ttattagttt    420
aaatttcatt tttgttttag ttggttaata tagtattaaa tcaattggta gattagttct    480
ctttcttaat aacaaatggc ttagttattt taggaacgcg atcaactcat ttcttttaat    540
atacgaaata atgtcaatga tttttttacaa aatatagagt tagtgtttgc agatattcgc   600
ataggtagaa tataagaatt ggtttattta tctcaaaccc aatcttcgta agcaaaatta   660
accaaacaat tataacctcg gactaaaaac aagtggtgta aaagaaggat gagatttata   720
gattgtaact ttttaagtca aaaaatgtgt aaatagtgtt tgctccaaat ataacaatga   780
aaattcttca aaaaatatta cttcatttat taaatcaatt gttttcctaa gttttatacg   840
caattcgctt tttgggtaga taaatattgt atttaccata aaaacggtag tattaatcac   900
acgttgttta ttttttatttt attttttattt tactctttaa actcatggtt tttgaggaat   960
ataattcaca cgtaaaaaaa tataatttgc ggtcacttaa tgaattgtga attcttttca   1020
aggaatttag aggcatctca aatagtgatt tctcatgact cttacattta aaatagatgg   1080
atgcaataaa catttgtaga gaatttatat tactgtcaag aatatttgca taattaagga   1140
tgcgttcgcg tgacttgatt atacttctaa aggcgattcg gattatgcgt tcgcgcaact   1200
tcgagcaaat ttttaataaa aagggttat tcggagatca tcaatattaa tttcatataa   1260
cctgagatgt gcagttcact atttaatcat acaagagcga cagacgttct taattttatt   1320
taagcacaat ttcgaactta agtctatttt tataataata aaaaaaattc gaaaataata   1380
ataattatat tatcaatatc attgtgtaca cgtgcgcgtg acacaactcc gcatgtttta   1440
aaaaatataa tttataacac gaatatacgt acgcgtgatt cgattcaaag aagggtcttt   1500
aaatctaaat agaagcggta acaataaaat catgcaataa aatgtatttt aacaaatcaa   1560
aataatcaag ccgaatataa cagttgagcg accgtgctag aaccacggaa ctcgggaatg   1620
cctaacacct tctcccgggt taacagaatt ccttatctgg atttctggtg cacagactgt   1680
taaatagaca gagtcatatt cttttcctcg attcgggatt aaaataggtg acttgggaca   1740
ccctaaatct cccaagtggc gactctgaaa taaagaaata aatcccgttt cgactgtact   1800
ttatttggaa aaaactccct tgcaccctcg cgggggcgga aaaggaggt gtgacaatta   1860 gtatttggta ttagcatgct ggttataaaa cttacccttg gtaatacaaa taaactcatc   1920
ttttatttta ttcttaattg ttgttcttgt atagtattaa agttttcaaa taattattcg   1980
catgatttca aacatatttt tttcatttat gccatataac ttcaaagttt gaatttgtgc   2040
ttttgtgatg gcaataatga atctcctaat ccgagaaata gttgaaattg agaaacatta   2100
tgatctcaac aggtagaatc aataaagctt tgctagaact ttccccaaat gtttatcaag   2160
gcgaaattat agacaatatt gagttttaaa tgaaattagg cttttcttga ttcacttttt   2220
agcctctctg ttttaccact acactcacac acacacacac acacacacac acacacacac   2280
acatatatat atatatatat atatatattc ctttagcacc caactttgag acttattaaa   2340
aaaacaagaa aggataaacc aactcttctt gatacaccat attggtttaa ccaaagagaa   2400
aaaaaattct tccagctata attgagcaga aatggctatt taatcaaggg atgaaggaat   2460
acttttggag taaagtttgt attcagagga aggtggattg gtttgtatat aaatttaaaa   2520
aaaatgatat gaatatcctt ctcaaaaaat gatgtgaata tacttatgga ataaattctt   2580
ggtgtaagaa gttagaactt atggagaata tttctgttga aaggaatgct gacttaattg   2640
gtgttaatca tggaactgaa gacatctcta gagtttatgt tctttgtatt aagttgtact   2700
```

-continued

| | |
|---|---|
| agttcctttg gtaaaataat tggctcacat tataaagctg gaaggaatac agtcactata | 2760 |
| aatatttcat ttacccttac cgcactaagc ctaacaataa aagcctgaaa aagtcataaa | 2820 |
| aagatcttaa aaatcaatgt tgattctata ttagtggaga ctgacatgaa gggcaagctt | 2880 |
| atgaacaaag tttgagaaac tcaaagattg tgatcataat gttatcaatc tcaaaaaaat | 2940 |
| tcatcaaaag gaggagaaaa agttttttgtc aaacaaaagc agagaaacac ggtaaagatt | 3000 |
| tggtgacttg aaaaacttat aggttttgaa tgttacgtga attttttattt tattactttt | 3060 |
| ctagtctaca agaaaaaata attactaata aaataattct cctcgaggac gagcaatgat | 3120 |
| tcaagtatgg gggagtttga tgaatataaa atattcatat attatatact aaaaaatata | 3180 |
| ctatttttaaa taaagtattt atataatatt tcgattctct gtattttcta acaatatttt | 3240 |
| gcaggagata agaatgctat taattaagca agaaaatgaa agaatcaaga agctcgtaac | 3300 |
| ggattcactc cataatgcaa gaagatcacg acgcatcttc ttcatgacgt atcttcctcg | 3360 |
| agatacatct tcctcaagac atattctcct caagatgcat cttcctcact tgagatcaca | 3420 |
| acacttcaag aagaaatgca cgtctataaa tagaaggcaa ttctctgtgt agtagacatc | 3480 |
| gaggaaaaag aaacaaaaga gccactttat tttctaaagc tttggtcact tattatttct | 3540 |
| tgttcttctt tcattactta taattttcag atttcctaga agtattggca aa | 3592 |

<210> SEQ ID NO 6
<211> LENGTH: 2913
<212> TYPE: DNA
<213> ORGANISM: Nicotiana tabacum

<400> SEQUENCE: 6

| | |
|---|---|
| ggagagctga gagatagcag cagaaaaggt cttcgattcc agcactttc taaagtttct | 60 |
| ttggagcttc taatattact gaagagcttt tttctactaa aggtggccat cgtcggaatt | 120 |
| tcaatttgct accattaatt tgcaaggccc tcctcctccc gttccctttg tcctctcctc | 180 |
| tctcttctgc acatccaaat ccaacttccc taccgccatt ttccgcactt cgataactcg | 240 |
| ttaaccccctc agtctctaat ttcttcctca ccccaaaaaa aaaaaaactt tcatttctct | 300 |
| gtcttctttc caaactttttt tcttcctccc ctgcttacac acaagaatct gtgatggatg | 360 |
| ccgcaaattt agtcatgaaa tcttccttgt tttcgaaatc cccatgtccc ctttttagtt | 420 |
| ctaaactcat tcctagagca ccaccctctg tctttactct gccttctacc tttagacccc | 480 |
| tcgttaaatg catacaagct tcattcccac caaaccctga ttccaaaaaa ccctcaaaca | 540 |
| attcaacctt tacgtgttca gctgtgactt ccttcccttc tcaacaatct cagcctcacg | 600 |
| cgccttccga tgccaagctc caactcctga tctctgaatt ccagtccctc gtcgaaccaa | 660 |
| tggaccgcgt gaaacgcctc ttgcactact ccacactcct ccctccaatg gacgcgtcct | 720 |
| tcaaaacccc tgagaatcgc gtaccgggtt gcactacaca ggtatggctg aacgtgagtt | 780 |
| tcgatgaggc tgaaacaggg atgaaatttt tggcggacag tgactcggaa ataactaaag | 840 |
| ggttttgcgc gtgtttggtt tcgctgctgg acgggctac tcccgatgag gtgctggcgt | 900 |
| tgaaaacgga ggacttgaat gctttgaatg ttgcggggtt gaacgggaaa ggatcggcat | 960 |
| ctagggcgaa tacgtggcat aatgtgttgg tcagcatgca gaaaaggaca agggccttag | 1020 |
| ttgcggagcg tgaaggcagg ccgcgcggcg agctcttttcc atctctagta atcacagctg | 1080 |
| atggtatcca accccaaggc agctacgctg aagcccaggc aaggttcctg tttcctgatg | 1140 |
| aatcaagggt ccaaaaactt gccaatttgc taaaggagaa gaaaatagga gttgttgctc | 1200 |
| atttctacat ggaccctgag gtgcaaggtg ttctaactgc agcgcagaag ctttggcccc | 1260 |

```
atatacatat atctgattct ttagtcatgg ctgataaagc tgtcagtatg gcaaaagctg    1320
gatgtgaata tatatctgta ttgggtgtag atttcatgtc agagaatgtg cgagccattc    1380
ttgatctagc tggattccca gaggttggag tttatcggat gtcggacgaa cgcattggtt    1440 gttcttttggc tgatgctgca gccagcccag catacttgga ttatcttaaa acagcttcaa    1500
cttcttctcc atctctgcat gttgtgtaca taaatacttc actggagaca aaagcatatt    1560
ctcatgagct tgttccgact ataacatgta cttcctctaa tgttgtgcaa actattctgc    1620
aggcatttgc tgaagtacct gacttggaag tgttgtatgg tcctgatacc tacatgggtt    1680
caaacattgc ggaattgttc acccagatgt ccacgatgac tgatgaagaa atttctgcga    1740
tacatccttt gcacaacaga atctccatta aatctttgct tcctcgactg cattatttc    1800 aggatgggac atgtattgtt catcacctct tggtcatga agttgtggag aagataaatg    1860
aaatgtatgg ggatgcattc cttactgcac actttgaagt tcctggtgaa atgttttccc    1920
tggcaatgga agcgaagaaa aggggcatgg gagtagtagg ttctacctcg aacatactcg    1980
actttatcaa agaaagggta gaagagtcct tgaatagaaa cgtagatgaa catcttcagt    2040
ttgttttggg aacggaatca ggaatgatta cggcaatagt tgcagcagtc ggtaaattac    2100
taggttctgc tgactcctct tccggtggag caaaagtaag tgttgagatt gtcttttcctg   2160 tctcgtcaga atcagtgaca agaacatcta cgggttcgcc tctggaccaa aataaggtca    2220
atattatacc tggagttgca agtggagagg ggtgttctct acatggtgga tgtgcctcct    2280
gtccatatat gaagatgaac tctcttagct cgttgctaaa agtttgccag agcttgcccc    2340
atggcaaagc cgaactttca gcttatgagg caggacgatt cagtttgcga acccccaagg    2400
gaaaacaaat tgcggatgtt ggttgtgagc cggttctgca catgagacac tttcaggcaa    2460
caaagagatt accagagcag ctaatcaatc aaatacttca acctcgtgat aatggacgat    2520
caagctctgc ttaaacaaga cgaaagctag acagacagtg gtatttactc gagacaaata    2580
aaagtttact tcccttcacc atacttggca agggaaggcc tagaggagca ttatgccagc    2640 ctcattttt ctgcatagga catggattat acaggaattt tatgctgtgc acatgctttg    2700
gttgttccgt ttcttacctt tctttttatt tttacctggt ttaagtgtga ttgtaataga    2760
tggaggaaaa taatggttgt acttttgttt cccctacaaa atattgaagg tgtttgtatt    2820
cgttatgctt aaataagctt taaagctctt ttagttttgt tcttttttag tgtttggcaa    2880
tattgtcaaa tttattttgg ttgaccaatc aaa                                  2913
```

<210> SEQ ID NO 7
<211> LENGTH: 2822
<212> TYPE: DNA
<213> ORGANISM: Nicotiana tabacum

<400> SEQUENCE: 7

```
gaagagctga gagattagca gcagataagg tcttcgattc cagttctaat attactgtag      60
agctttcttc tacaaaaggt ggccatcgtc ggaatttcaa tttgctacca ttaatttact     120
aggtcctcct cctcccttc cctctgtcct ctcctctctc ttctgcacat ccaaatccat     180
cttgcctacc gccattttcc gcacttcgag aactcgttaa ccctcactc tccaatttcg     240 tcctcaccca aaaaaaaaa aaaaaaaacc ttgtcagttc tctgtcttct tttcaaactc     300
ttttcttctt tctcctctgc ttaaacacaa gaatctgtta tggacgccgc aaatttagtc     360
atgaaatctt ccatgttttc gaaatcccca tgtcccgttt ttggttctaa actcattcct     420
```

```
agagcaccac cctctgtctt tactctgcct tctaccttta gacccctcgt taaatgcata    480
caagcttcct tcccacaaaa ccctgattcc aaaataccct caaacaattc aacctttacg    540
tgttcagccg tgacttcttt cccttctcaa cagtctcagc ctcacgcgac ttccgatgcc    600
aagctccaac tcctgatctc ggaattccag tccctcgtcg aaccaatgga ccgcgtgaaa    660
cgcctcttgc actactccac actcatccct tcaatggatg cgtccctcaa aaccccagag    720
aatcgcgtgc tgggttgcac tacacaggta tggctgcacg tgagtttcga tgaggccgag    780
aacaggatga aatttgtggc ggacagtgac tcggatataa ctaaagggtt ttgcgcgtgt    840
ttggtttcgc tgctggacgg agctactcct gatgaggtgc tggcgttgaa acggaggac     900 ttgaatgctt tgaatgttgc gggtttgaac gggaaaggat ctgcatctag ggcgaatacg    960
tggcataacg tgttggtcag catgcagaaa aggacaaggg ccttggtggc ggagcgtgaa    1020
ggcagaccgc gcaacgagct cttcccatct ctagtaatca ctgctgatgg tatccaaccc    1080
caaggcagct acgctgaagc ccaggcaagg ttcctgtttc ctgatgaatc aagagtccaa    1140
gaacttgcca gtttgctaaa ggagaagaaa ataggagttg ttgctcattt ctacatggac    1200
cctgaggtgc aaggtgttct aactgcagcg cagaagcttt ggccccatat acatatatct    1260 gattcttag tcatggctga taaagctgtc agtatggcaa aagctggatg tgaatatata     1320
tctgtattgg gtgtagattt catgtcagag aatgtgcgag ccattcttga tctagctgga    1380
ttcccagagg ttggagttta tcggatgtcg gatgaacgca tcggttgctc tttggctgat    1440
gctgcagcca gcccagcata cttggattat cttaaaacag cttcaacttc ttctccatct    1500
ctgcatgttg tgtacataaa tacttctctg gagacaaaag catattctca tgagcttgtt    1560
ccgactataa catgtacttc ctctaatgtt gtgcaaacta ttctgcaggc atttgctgaa    1620
gtacctgact tggaagtgtt gtatggtcct gatacctaca tgggttcaaa cattgcagaa    1680
ttgttcaccc agatgtccac gatgactgat gaagaaattt ctgagataca tcctttacac    1740
aacagaagct ccattaaatc tttgcttcct cgactccatt attttcagga tgggacatgt    1800
attgttcatc acctctttgg tcatgaagtt gtggagaaca taaatgaaat gtatggtgat    1860
gcattcctta ctgcacactt tgaagttcct ggtgaaatgt tttccctggc aatggaagcg    1920
aagaaaaggg gcatgggagt agtaggttct acctcgaaca tactcgattt tatcaaagaa    1980
agggtggaag aggccttgaa tagaaacgta gatgaacatc ttcagtttgt tttaggaacg    2040
gaatcaggaa tgattacggc aatagttgca gcagtcggta aattactagg ttctgctgac    2100
acctcttccg gtggagcaaa agtaagtgtt gagattgtct ttcctgtctc gtcggaatca    2160
gtgacaagaa catctaccgg ttcgtctctg gaccaaaata aggtcaatat tatacctgga    2220
gttgcaagtg gagagggatg ttctctacat ggtggctgtg cctcctgtcc atatatgaag    2280
atgaactctc ttagctcgtt gctaagagtt tgccagagct tgccccatgg caaagccgaa    2340
ctttcagctt atgaggcagg acgattcagt ttgcaaaccc ccaatggaaa acaaattgcg    2400
gatgttggtt gtgagccggt tctgcacatg agacactttc aggcaacaaa gagattacca    2460
gagcagctaa tcaatcaaat acttcaacga tcaagctccg cttaactaag acgaaagcta    2520
gatgaaaagt ggtatttact tgagacaaat aaaagtttac ttcccttcac catacttggc    2580
cagggaaggc ctggaggagc attatgccag cctcatttt  tctgcatagg acatggatta    2640
tacaggaatt ttatgctgtg cacatgcttt gattgttccg tttcttacct tttcttttc     2700 tttttacttt ggtttaagtg tgattgtaat agatggtgga aaataatgat tgtacttttg    2760
ttttccctac aaaatattga aggtgtttgt attggttctg gtcaaaaaaa aaaaaaaat    2820
```

```
ag                                                                      2822
```

<210> SEQ ID NO 8
<211> LENGTH: 1232
<212> TYPE: DNA
<213> ORGANISM: Nicotiana tabacum

<400> SEQUENCE: 8

```
ggattcccgg gattttgaat tcttgaaata tttgaaatta aattcccttc cgcccgtctt    60
tacaaataat tatattacag tatatatctt gtttcactaa attaaatatc aaaaaatggc   120
cttaccacaa gagaattgca ctacacttga tttaattagg caacatcttc ttgatgataa   180
tgttttcatg gaacattatt gtccccaacc aattctttat tctcaaagct cctcctcttc   240
tgaatcttta aactccattg cttctgagct caataacgac actttctcct ttgaaccaac   300
tctcaactat gccgacacag cccaaagttc aatcttgat atctcaacct tctttaacaa    360
ttcaaaaaca gagtttgact gctttgagtt tgagacaaaa ccaaacgtgt tagctgctcg   420
tattagtcca aattctccga agcaaacaag cttcaaagaa cgcaagcctt ctctaaatat   480
tgctataccc ctgaagcatc aagaggttgt tcagaaagtg gaaaaatcca atgagagcga   540
gaagaagcat tacagaggag ttaggcaaag gccgtggggc aagttcgcgg cagagattcg   600
tgacccgaac cgaaagggga ctcgggtttg gttaggaacc tttgacactg ccttagaggc   660
ggctaaggca tatgacaggg cggcgtttga gcttagaggc agcaaagcta tagtgaattt   720
ccctctcgaa gttgcaaact ttaagcaaga atttaataat gagattcggc cattggtgaa   780
ctcaagcagg aaaagggtga gagaaacagt gaatgaggag caactagtta tcaataagga   840
aatgaaaata gaagaagaaa gagtcccgac ggctccatta acgccgtcaa tttggtcggc   900
aatttgggac agtggagatg ggaagggtat ttttgaagtg ccgccattat ctccacatat   960
ggcctattct cagcttgtca tgatataatc aataatggat aaggagtata aatttgggga  1020
tgttagtatt tggaagatga tgaatatata aatatgcacc tgactatgaa gaaagtctga  1080
ggtgaaatca agaattaaga tgagattcaa taggaagatg tagaacaata aaatagtcca  1140
tggatgtgtc tttgggtctt taatctttc tgattttatt gatttagcgt tatttcatgt   1200
aaatacgcag tgagtttaac aatttgttcg at                                 1232
```

<210> SEQ ID NO 9
<211> LENGTH: 1026
<212> TYPE: DNA
<213> ORGANISM: Nicotiana tabacum

<400> SEQUENCE: 9

```
ctttcccctcg ttttattagc agatcaaaaa tggcctcacc acaagagaat tgcactacac   60
ttgatttgat aaggcagcat cttttgatg atgctgcttt tatggaatat tactgctctg   120
aacctaccac cctttattcc caaaactcct cctcttctga atctctggac cagagtttct   180
cttttgaacc aactctcaac tatgccgaca cagcacaaag ttccagtttt gaaatctcta   240
gcttctttga caattcaaaa acagagtttg actgctctga gttggagaca attcaaaaac   300
agagtttgaa ttctcggaag caaacaagct tcaagaacg caagccttct ctgaacattg   360
cgataccagt gaagcagcag aaagtggaag tagttccaag agggaagaag cattacagag   420
gagttaggca aaggccgtgg ggcaagttcg cagcagaaat tcgtgacccg aaccgaaagg   480
ggactcgggt ttggttagga acctttgaca ctgccttaga ggcggccaag gcatatgaca   540
```

```
gggcagcgtt taaacttaga ggaaacaaag caatagtgaa tttccctctc gaagttgcaa      600
actttaagca agaatataat aatgagattc cacagtcagc taactcaggc cggaaaaggg      660
tgagagaaac agagaatgag gagcaactcg ttatcaataa ggaaatgaaa atagaagaag      720
aaagagtccc tacgactcca ttaacgccgt caagttggtc ggcgatttgg gacagtggag      780
atgggaaggg tatatttgag atgccgctgc tttccccatt gtctccacat ttgccttatt      840
ctcagcttgt cattatataa tcaaaaggac accggtatat atacatatgc acctgaccgt      900
aaagaaagtc tgaggtgatt ccctgaattg ggattaggac tcaatagaag atgtgtagaa      960
gaggggtgtc tttgagtctt gaattctttt caatttcatt gattaagcgt taattcttgt     1020
aaatag                                                                1026

<210> SEQ ID NO 10
<211> LENGTH: 1355
<212> TYPE: DNA
<213> ORGANISM: Nicotiana tabacum

<400> SEQUENCE: 10
gatttctcca acccagaagg ctcctatgaa acctcttctc atctcaaaat tctgaccttt       60
ataactatcc tccccacact ctcttttttcc actcaactca atactctccc cactttgaat     120
tctttcaaga atttaaatat atatagctga aattagattc ttcaactctc tttccctcgt     180
tttattagca gatcaaaaat ggcctcacca caagagaatt gcacacttga tttgataagg      240
cagcatcttt tgatgatga tgcttttatg gaatgttact gctctgaacc taccacccctt     300 gattcccaaa actcctcctc ttctgaatct ctggaccaga gtttctcttt tgaaccaact      360
ctcaactatg ccgacacagc ccaaagttcc agttttgaaa tctctagctt ctttgacaat      420
tcaaaaacag agtttgactg ctttgagttg gagacaattc aaaaacgagag tttgaattct     480 cggaagcaaa caagcttcaa agaacgcaag ccttctctga acattgcaat acctgtgaag      540
ctgcagaaag tggaagtagt tccaagcgag aagaagcatt acagaggagt taggcaaagg      600
ccgtggggca agttcgcagc agaaattcgt gacccgaacc gaaaggggac tcgggtttgg      660
ttaggaacgt ttgacactgc cattgaggcg gccaaggcat atgacagggc ggcgtttaag      720
cttagaggaa gcaaagcaat agtgaatttc cctctcgaag ttgcaaactt taagcaagaa      780
tataataatg agattccaca gtcggctaac tcaggccgga aaagggtgag aggaacagag      840
aatgaggagc aattagttat caataaggaa atgaaaagag aagaagaaag agtccctact      900
gcggcggctc cattaacgcc gtcaagttgg tcggcgattt gggacagcgg agacggaaaa      960 ggaattttttg aggtgccgcc tctttcccca ttgtctccac atataggggta ttctcaggtt    1020 gtgatgatat gatcagataa ggaacggcaa cgtatataga ttgtggtgtt agtatttagt     1080
agatgaagga taaatattgc acctgactgt aaaaagtctg tggtgattaa tttctcagcc     1140
aaaaaaagaa atatgggga aggtgggggt agctacggga attagtatgg tgataataaa      1200
gattggtgtc tggtctcctc cttaagtctt ttgattaaat tttattgttt atgtaaaaac     1260
gtcagtcaga gatctgtttg attgttttat atattcatat ctatgaaact atgaaagcat     1320
atacctacta aaacctacgt atttattaa accca                                  1355

<210> SEQ ID NO 11
<211> LENGTH: 261
<212> TYPE: DNA
<213> ORGANISM: Nicotiana tabacum

<400> SEQUENCE: 11
```

```
gatgatagtt tatctttgag aaaggctcta atagtatgca gagtgattgc tggtagggtg      60
catagacctt tggaaaatgt tcaagaattg attggtcaat cagggtttga ttcattggct     120
ggaaaagtag gactctactc aaatattgaa gaactctatt tgctcaattc taaagctttg     180
cttccttgtt ttgtggtaat ctgtaaatca taaaaaatac aaggtgattg agccattctt     240
tcatgtaatt caattgaagt t                                               261
```

```
<210> SEQ ID NO 12
<211> LENGTH: 725
<212> TYPE: DNA
<213> ORGANISM: Nicotiana tabacum

<400> SEQUENCE: 12
acatggggat tcatacttta ctgcaatatt acaacttta ctagatccaa cttcaatttc       60
ttgattcact aatactctat atttcttgat tccttatctc cctcttctat ctctctctct     120
ctataaaaga aaaactctat tcattggcag ctagcttttg atctgtagag tttgtggctg     180
aagttaaacg aagatgagaa gaaactgtaa cttggagctc aggcttatgc ctccttcttt     240
ttcttttcct cctaagaatt gcactacccc ttacttctca acggataggg aggataaaga     300
aagcacagaa gagaaacaac cacagcagct aacaatattt tacaatggaa aatttgtggt     360
ttctgatgct actgaacttc aggctaaagc aataatatat ctggcaagta gagaaatgga     420
ggagaaaaca aaaatccggt caccaatttc agaatcatca tcaccaattt cagagccttc     480
atcaccattt ttacaatctc cagcttctga tctttctatg aagagatctc tacaaaggtt     540
tctgcagaag agaaaaaata gaattcaagc aacttctcct tatcatcact agtttagttc     600
catttgtaca tatattttgt aatttgcggg gagaaattgg aaaattggat tagtaagcaa     660
aacactagtg tatcacttaa ttttacagtt tcggcaatgc aattttttca taaaagggtg     720
ggcgc                                                                 725
```

```
<210> SEQ ID NO 13
<211> LENGTH: 1490
<212> TYPE: DNA
<213> ORGANISM: Nicotiana tabacum

<400> SEQUENCE: 13
atgtgggtac tatttccctc acattttcct ttcacaataa acaaacttcc gcctcaaagc      60
cgaaaaacca gagctctcag ctctatttc tcttgctatt ttcaacaaac tgttaacgat      120
ctcgtcagct atttccgaaa tcctgaagtt ggagctagtt ttaagtgaaa ataatgagag     180 gagatttat gggtttgact catcatgtga agcaagaagt cactgaagaa cctatagatc     240
cagcacctct gagaagttca gcaatgcagt ggtcattctc gaacaacatc tcgactcatc     300
ctcaatacct ctcttcaag ggtgctcaag aggataggcc aaaaactggt tttgattctc      360
ttgcatcaac tggattggtg actataacca caactgaagc tgtcgactcg agtcatcgat     420
catactctgg tgtcgggcag aaaaatatga tgcttgaaaa gcaaggtgga acacactaca     480
tgtcgacaac tttctctcct catcactatg atgcacacgc catgcatcga tctcatggtg     540
tcagagtgct cccagtttcc aacccagcaa atcagatttc tgtatcaatg actatgcctg     600
gtcataagtc ctttgtttct cctcttggac agaatccagt tgctagcccc atttcagctg     660
ttccaactaa cagcgctgtc gtgggcacaa ctgatttaag gggtgctccg aaaactcccc     720
caggtcctgc tcagttgacc atcttttatg ctggttccgt ctgcgtttat gataatgttt     780
```

| | |
|---|---|
| caccagagaa ggctcaagct attatgttgc ttgctggaaa tgcaccacct gttacgccaa | 840 |
| gtgcaacatc tgctctatct ccagttcagg cgcccatacc taagtcctct tctgttgact | 900 |
| cttttgttgt aaatcagtcc cataacacaa cacctactct ccccagcccc atttctataa | 960 |
| catcccattg tggatctcaa tctgctggag tgtctagtaa tacaaatgga gtaactatta | 1020 |
| tcaaatcaat tggggtccta ccatctcctt ctaataaagc agaactttct aaattttcca | 1080 |
| gttccatagg atctgttcct gccacctttg ttcaatcagc tgtaccacag gcacgcaagg | 1140 |
| catcattggc tcggttcttg gagaagcgca aagaagggt aataagtgca tcaccttacg | 1200 |
| tcagctgcaa gcaatcccca gaatgcagca ctcttggata tggaagcaga agtttcgcaa | 1260 |
| aagattcttt aggctctttt cctcccccat gtaatcaatt tggtcaagga gacgtgaaat | 1320 |
| gccaacagtg gcaaaataat gtagacacaa ggtgaagact gtaccagatt agattattaa | 1380 |
| agctaaattg gtggtcgttt tgacttcaat acttcagttc tctcttagat gcgatatatt | 1440 |
| attttaggtt gttttccttg taattgtgat cagagccttt tcatctgaaa | 1490 |

<210> SEQ ID NO 14
<211> LENGTH: 1078
<212> TYPE: DNA
<213> ORGANISM: Nicotiana tabacum

<400> SEQUENCE: 14

| | |
|---|---|
| gacttaaaaa ttgccttctt tttcatctca tccatagttt cttgaattct tgttttgg | 60 |
| atttcaactt ctatttcagc ttctatgtct ataccattcg aacatgatta tataggttta | 120 |
| tcagaagctt ctttaatgga aagaaattct gataaaata gtgatgttct taaccttaag | 180 |
| gagactgagc taagacttgg gttaccgggt actgaggaaa caaatacggg tcttaaccct | 240 |
| tcaaacaatt ttatatcaag aaccaaaagg ggttttttctg atgccattga tgcttctgga | 300 |
| aaatgggatt tgtccattaa ttgcagatca gaaactgatt ggagaaaaga agacttgtta | 360 |
| ttttccccca aaggaagtaa tggaagctca agccaactc catcaattga aaatagtgct | 420 |
| cctcagactt caaaggcaca agtagtagga tggccaccaa ttagatcatt ccgcaaaaat | 480 |
| acactggcca ccaaaaagaa tgatgctgaa ggaaaatcag gttcaggttg ccttatgtg | 540 |
| aaagttagaa tggatggtgc tccatatttg agaaaggttg atatcaaaac ttacagcgac | 600 |
| tatggggagc tctcatcagc acttgaaaag atgttcagct gctttagtat tgggcagtgc | 660 |
| gccagcgatg gacttccggg gcaagaggaa cttagtgaaa gtcacttgat ggatcttctc | 720 |
| aatggttctg agtatgttct gacttatgaa gacaaagatg gtgattggat gcttgttggc | 780 |
| gatgttcctt gggagatgtt catagactca tgcaagagat tgcggatcat gaaaagctca | 840 |
| gaggcaattg ggctagctcc aagggctata cacaagtgca agaacaaaaa ctagtgactg | 900 |
| aaaaaccatt caatggttc tatgtcgatg attatccttt ttctgctctc ttttgtatct | 960 |
| ggaattagac tagacgtgta gcattccctg aaaggaaaag cactggttta agaagatata | 1020 |
| accggtgata tccaagattt ttgtttagtg tttagtgttc cctacggaaa aaagaaa | 1078 |

<210> SEQ ID NO 15
<211> LENGTH: 621
<212> TYPE: DNA
<213> ORGANISM: Nicotiana tabacum

<400> SEQUENCE: 15

| | |
|---|---|
| cagaggataa aactccccaa cccagatgct ctccccaaat ccctaaatcc aacgtcagtg | 60 |
| attttttgcta tagtttataa aattaccaag aacgtcgtta cacgaattca acgtctcaac | 120 |

```
cccgatttga gacttgatcc tcacatacta atcttctgtg ctcgtgcacc tggagaagct      180
tcctctccac accaagctga tattcaacca atcaattttc catctgatgg tagtaacaat      240
caaggtcgag agtcctccaa ataggctatc agctcagcgg aaggttttgc tgcgctccat      300
ttgctccgga gttgcttatg tggtcaatat gattaggaca tgtactgatt agtatgtcgg      360
ggccgtgtcc cgacctttat gacatttatg tactcttaga ggtttgtaga catatgtcga      420
atacgtgaaa gattgtacgg ccttgtcggc ctatgttttg agtttataaa tgatcatgtt      480
ggcctattag gcccgtatgt cacatgtata tgatgatgta ataagaaaga tacgttacgt      540
tggtactcgg ttgagtaagg taccgggtgc ccgtcgtggc ccatcggttt gagtcgtgac      600
acttctctgc ctcaaattca a                                                621
```

```
<210> SEQ ID NO 16
<211> LENGTH: 496
<212> TYPE: DNA
<213> ORGANISM: Nicotiana tabacum

<400> SEQUENCE: 16
```

```
gcttttagaa ttgggattaa agagttttt acgactagag agagagagaa gcagaagctg       60
aaggagaaga gaatatcgga agaaggatga tacaccggaa atggagtttg ctaacaggcc      120
ccgctgcaat tctcggcggt atcgtcggta ctatcgtcgt cgccaatttt atcttcgtcc      180
aaaatgaccc gttccttaag cccgatcgga agcaggagaa ggcaccttca aacaagtgag      240
aaatgcgtgt gattttctct ggtttggggt tttctgttgg tttgatttgt cactacatta      300
cggcccaata aactcaaatt tgagcatta gcttgaatgt aggttttctt ttgttggctt       360
tctttctgta ctctttctct tcacagaata tgaaagtatg ctccaaacaa gagtcctagg      420
ttgggaactg gtcatctcct gtttcgtgac gctttattca ggttatgaat agaataaaat      480
gtggagatgc gacaaa                                                      496
```

```
<210> SEQ ID NO 17
<211> LENGTH: 546
<212> TYPE: DNA
<213> ORGANISM: Nicotiana tabacum

<400> SEQUENCE: 17
```

```
gtgagagacg gaaagttcaa tccaccagca cagagaacaa gagaaatccc taaatggcga       60
cggcgatgtt cagatctagt attcgctccg ccctccgcag cggcgctcct cgtgtaactc      120
cggcttccaa gagaaccttc tcttctcact catccgttga ggaagaggcc cgtgaagcct      180
ctaagtggga gaaaattact tatgttggaa tagtttcctg ctctattctt gctgcgattt      240
gtctgtcaaa gggtcaccct cactctgatg agcctcctgc ttactcatat ctgcacattc      300
gcaacaagga gtttccatgg ggtccagatg gcttttttga ggtcaagcac cactgaaact      360
gcgtggtttc tctgtgaagg cgttaaaata attcctgtcc atccgcgagg atgatcacat      420 tgttgaatt tccattagat gtctactttt ggttctttgc ttataagaaa cctttgcctt       480
ttctttgaca tatttccatc ttttgctgta tacttacaat gtgctttaaa gaataagaat      540
tcagga                                                                 546
```

```
<210> SEQ ID NO 18
<211> LENGTH: 537
<212> TYPE: PRT
<213> ORGANISM: Nicotiana tabacum
```

```
<400> SEQUENCE: 18

Met Glu Val Ala Phe Arg Lys Ser Ile Asn Gly Gly Leu Val Lys Glu
1               5                   10                  15

Glu Lys Arg Asn Lys Leu Ala Tyr Gln Ser Ser Asp Glu Glu Gly
            20                  25                  30

Phe Val Glu Asp Ser Asn Val Leu Lys Val Gly Lys Glu Arg Glu Val
                35                  40                  45

His Glu Asp Asp Asn Ser Lys Tyr Pro Gln Gln Glu Asp Ile Asp Ser
    50                  55                  60

Asp Lys Glu Asp Asp Gln Leu Gln Ser Val Lys Ala Asp Met Lys Glu
65                  70                  75                  80

Val Met Lys Glu Asn Gln Arg Leu Lys Met His Leu Asp Arg Ile Met
                85                  90                  95

Lys Asp Tyr Arg Asn Leu Gln Leu Gln Phe His Asp Ile Val Gln Arg
            100                 105                 110

Asn Ala Glu Lys Ser Asn Ser Ile Ile Asp Thr Asp Arg His Asn Glu
                115                 120                 125

Cys Asn Glu Ala Glu Phe Val Ser Leu Ser Leu Gly Arg Ser Ser Ser
130                 135                 140

Asp Thr Lys Lys Glu Glu Tyr Leu Ser Lys Ile Leu Ser Lys Asp Lys
145                 150                 155                 160

Ala Glu Glu Glu Asn Lys Gly Gly Leu Thr Leu Gly Leu Asp Cys Lys
                165                 170                 175

Phe Asp Leu Cys Val Lys Thr Thr Pro Thr Glu Phe Ser Thr Ala Asn
            180                 185                 190

Leu Ser Glu Glu Asn Arg Ser Glu Glu Val Lys Asp Glu Asn Gly Glu
                195                 200                 205

Thr Leu Pro Pro His Lys Ile Leu Lys Thr Met Arg Asn Gly Glu Asp
210                 215                 220

Asp Thr Gln Pro Asn Pro Ser Lys Arg Ala Lys Val Ser Val Arg Val
225                 230                 235                 240

Arg Cys Asp Ala Pro Thr Met Asn Asp Gly Cys Gln Trp Arg Lys Tyr
                245                 250                 255

Gly Gln Lys Ile Ala Lys Gly Asn Pro Cys Pro Arg Ala Tyr Tyr Arg
            260                 265                 270

Cys Thr Val Ala Pro Ser Cys Pro Val Arg Lys Gln Val Gln Arg Cys
                275                 280                 285

Ile Glu Asp Met Ser Ile Leu Ile Thr Thr Tyr Glu Gly Thr His Asn
290                 295                 300

His Pro Leu Ser Leu Ser Ala Thr Ser Met Ala Ser Thr Thr Ser Ala
305                 310                 315                 320

Ala Ala Ser Met Leu Leu Ser Gly Ser Ser Ser Ser Glu Ser Gly
                325                 330                 335

Pro Asn Pro Pro Ala Thr Asp Ala Thr Asn Ile Asn Gly Leu Asn Phe
                340                 345                 350

Tyr Leu Ser Asp Ser Ser Lys Pro Lys Pro Phe Tyr Leu Gln Asn Ser
            355                 360                 365

Ser Ile Ser Ser Ser Ser Pro Pro Thr Ile Thr Leu Asp Leu Thr
                370                 375                 380

Ser Ser Ser Phe Thr Ser Leu Phe Pro His His Asn Arg Met Ser Ser
385                 390                 395                 400

Asn Tyr Leu Pro Arg Tyr Asn Ser Ser Thr Asn Ile Leu Asn Phe Ser
                405                 410                 415
```

```
Ser Leu Glu Ser Asn Pro Leu Leu Pro Met Ser Trp Ser Asn Gly Ala
            420                 425                 430

Tyr Asn Lys Asn Gln Glu Ile Ser Ser Leu Asn Phe Ala Arg Arg Pro
        435                 440                 445

Gln Asp Ile Leu Phe Gln Ser Tyr Leu Gln Asn Asn Ile Ser Ala Lys
450                 455                 460

Pro Thr Gln Ser Leu Leu Pro Gln Asp Thr Ile Ala Ala Ala Thr Lys
465                 470                 475                 480

Ala Ile Thr Ser Asp Pro Asn Phe Gln Ser Ala Leu Ala Val Ala Leu
                485                 490                 495

Ala Ser Ile Ile Gly Ser Gly Ser Gly Asn His Ala Gly Gly Ile Glu
                500                 505                 510

Glu Lys Ser Gly Leu Asn Leu Lys Val Thr Glu Pro Phe Pro Val Leu
            515                 520                 525

Cys Ser Phe Pro Ser Thr Ser Lys Lys
            530                 535

<210> SEQ ID NO 19
<211> LENGTH: 605
<212> TYPE: PRT
<213> ORGANISM: Nicotiana tabacum

<400> SEQUENCE: 19

Met Gly Thr Val Asn Met Ser Trp Ser Asp Glu Asp Lys Ala Thr Val
1               5                   10                  15

Ala Ala Val Leu Gly Lys Glu Ala Phe Glu Tyr Leu Ile Ser Ser Ser
                20                  25                  30

Val Ser Ala Glu Cys Ser Leu Met Ala Ile Gly Asn Asp Gln Asn Leu
            35                  40                  45

Gln Asn Lys Leu Ser Asp Leu Val Glu Arg Pro Asn Ala Thr Asn Phe
50                  55                  60

Ser Trp Asn Tyr Ala Ile Phe Trp Gln Ile Ser Arg Ser Lys Ser Gly
65                  70                  75                  80

Glu Leu Val Leu Gly Trp Gly Asp Gly Cys Cys Arg Glu Pro Arg Glu
                85                  90                  95

Gly Glu Glu Arg Glu Val Lys Ser Ile Phe Asn Leu Arg Leu Glu Asp
                100                 105                 110

Glu Ala Pro Gln Arg Met Arg Lys Arg Val Leu Gln Lys Leu His Met
            115                 120                 125

Leu Phe Gly Gly Thr Asp Glu Asp Asn Tyr Ala Ile Gly Leu Asp Arg
130                 135                 140

Val Thr Asp Thr Glu Ile Phe Phe Leu Ala Ser Met Tyr Phe Ser Phe
145                 150                 155                 160

Pro Arg Gly Glu Gly Gly Pro Gly Lys Cys Phe Gly Ser Gly Lys His
                165                 170                 175

Leu Trp Leu Ser Asp Ala Leu Lys Ser Pro Leu Asp Tyr Cys Ala Arg
            180                 185                 190

Ser Phe Leu Ala Lys Ser Ala Gly Met Gln Thr Ile Val Leu Ile Pro
        195                 200                 205

Thr Asp Val Gly Val Val Glu Leu Gly Ser Val Arg Ser Ile Pro Glu
210                 215                 220

Ser Leu Glu Leu Leu His Ser Ile Lys Ser Cys Phe Ser Ser Phe Leu
225                 230                 235                 240

Val Arg Ala Lys Gln Ala Ala Gly Leu Ala Val Val Thr Glu Lys Lys
```

```
                        245                 250                 255
Asp Gly Asn Asn Ser Pro Phe Ser Ser Ser Ala Phe Ser Glu Arg Pro
                260                 265                 270

Asp Gly Ile Pro Lys Ile Phe Gly His Asp Leu Asn Ser Gly Thr His
                275                 280                 285

Phe Arg Glu Lys Leu Ala Val Arg Lys Ala Glu Glu Arg Pro Trp Asp
                290                 295                 300

Ile Tyr Gln Asn Gly Thr Arg Met Pro Phe Met Asn Gly Arg Thr Gly
305                 310                 315                 320

Leu His Ala Ala Ser Trp Ala Gln Phe Ser Asn Val Lys Pro Val Lys
                325                 330                 335

Pro Val Glu Leu Tyr Ser Pro Gln Thr Pro Ala His Asn Leu Gln
                340                 345                 350

Glu Leu Val Asn Gly Gly Arg Glu Glu Phe Arg Leu Asn Asn Phe Gln
                355                 360                 365

His Gln Lys Pro Ala Arg Met Gln Ile Asp Phe Thr Gly Ala Thr Ser
                370                 375                 380

Arg Pro Ile Ile Ser Pro Ala His Thr Val Glu Ser Glu His Ser Asp
385                 390                 395                 400

Val Glu Ala Ser Cys Lys Glu Asp Cys Ala Gly Pro Val Asp Glu Lys
                405                 410                 415

Arg Pro Arg Lys Gly Arg Lys Pro Ala Asn Gly Arg Glu Glu Pro
                420                 425                 430

Leu Asn His Val Glu Ala Glu Arg Gln Arg Arg Glu Lys Leu Asn Gln
                435                 440                 445

Arg Phe Tyr Ala Leu Arg Ala Val Val Pro Asn Ile Ser Lys Met Asp
                450                 455                 460

Lys Ala Ser Leu Leu Gly Asp Ala Ile Ala Tyr Ile Thr Glu Met Gln
465                 470                 475                 480

Lys Lys Leu Arg Asp Met Glu Ser Glu Arg Glu Leu Arg Leu Gly Ser
                485                 490                 495

Thr Ser Arg Asp Ala Met Ala Ala Glu Asp Ser Pro Asn Ser Glu Ile
                500                 505                 510

Gln Ile Arg Gly Pro Asp Ile Asn Val Glu Ala Ala Asn Asp Glu Val
                515                 520                 525

Ile Val Arg Val Ser Cys Pro Leu Glu Thr His Pro Ile Ser Arg Val
                530                 535                 540

Ile Gln Thr Phe Lys Asp Ala Gln Ile Asn Val Val Glu Ser Lys Leu
545                 550                 555                 560

Ser Ala Gly Asn Gly Thr Val Phe His Thr Phe Val Leu Lys Ser Ser
                565                 570                 575

Gly Ser Glu Gln Leu Thr Lys Glu Lys Leu Leu Ala Ala Phe Ser Ser
                580                 585                 590

Glu Ser Asp Ser Leu Arg Gln Phe Ser Pro Val Gly Gln
                595                 600                 605

<210> SEQ ID NO 20
<211> LENGTH: 305
<212> TYPE: PRT
<213> ORGANISM: Nicotiana tabacum

<400> SEQUENCE: 20

Met Gly Arg Pro Pro Cys Cys Asp Lys Ile Gly Val Lys Lys Gly Pro
1               5                   10                  15
```

```
Trp Thr Pro Glu Glu Asp Ile Met Leu Val Ser Tyr Val Gln His
             20                  25                  30

Gly Pro Gly Asn Trp Arg Ala Val Pro Thr Asn Thr Gly Leu Arg Arg
         35                  40                  45

Cys Ser Lys Ser Cys Arg Leu Arg Trp Thr Asn Tyr Leu Arg Pro Gly
 50                  55                  60

Ile Lys Arg Gly Ser Phe Thr Asp Gln Glu Glu Lys Met Ile Ile Gln
65                   70                  75                  80

Leu Gln Ala Leu Leu Gly Asn Lys Trp Ala Ala Ile Ala Ser Tyr Leu
                 85                  90                  95

Pro Glu Arg Thr Asp Asn Asp Val Lys Asn Tyr Trp Asn Thr His Leu
             100                 105                 110

Lys Lys Lys Leu Lys Lys Leu Glu Ser Ser Asp Leu Tyr Ser Lys Asp
        115                 120                 125

Gly Ser Cys Leu Ser Pro Ser Asn Ser Thr Ser Arg Gly Gln Trp Glu
130                 135                 140

Arg Thr Leu Gln Thr Asp Ile Asn Thr Ala Lys Gln Ala Leu Gln Asn
145                 150                 155                 160

Ala Leu Ser Leu Asp Lys Ser Ser Pro Ile Pro Glu Tyr Thr Thr Thr
                165                 170                 175

Asp Val Lys Pro Ile Asn Leu Gly Cys Tyr Ser Tyr Ile Lys Gln Glu
            180                 185                 190

Gly Lys Val Ser Thr Ser Thr Tyr Ala Ser Ser Ala Glu Asn Ile Ala
        195                 200                 205

Lys Leu Leu Lys Gln Trp Thr Arg Ser Asp Ser Thr Asn Ile Ser Glu
210                 215                 220

Gln Ser Lys Ala Ser Ser Ser Thr Gln Leu Ser Ser Asn Asn Asn Ala
225                 230                 235                 240

Thr Thr Glu Glu Phe Glu Ser Leu Ser Ser Phe Asp Ser Phe Glu Gln
                245                 250                 255

Ser Asn Ser Asp Gln Phe Ser Gln Ser Leu Thr Leu Glu Ala Gly Lys
            260                 265                 270

Leu His Cys Glu Ile Ser Lys Arg Glu Val Asp Asp Gln Val Pro Leu
        275                 280                 285

Ser Val Met Leu Glu Ser Trp Leu Phe Asp Glu Asn Asp Asp Leu Leu
290                 295                 300

Ile
305

<210> SEQ ID NO 21
<211> LENGTH: 327
<212> TYPE: PRT
<213> ORGANISM: Nicotiana tabacum

<400> SEQUENCE: 21

Met Glu Ser Gln Trp Gln Glu Asn Ser Leu Ser Asp Leu Lys Met Leu
1               5                   10                  15

Ile Lys Glu Leu Asn Cys Gly Gln Glu Phe Thr His Lys Leu Arg Asp
            20                  25                  30

Val Ile Lys Gln Ser Leu Val Asn Gly Asp Met Asn Met Leu Ala Glu
        35                  40                  45

Asn Leu Val Gly Gln Ile Met Gly Ser Phe Cys Lys Thr Leu Ser Ile
    50                  55                  60

Leu Asn Thr Ser Asn Ser Asn Glu Asp Ser Gln Ile Pro Met Val Ala
65                  70                  75                  80
```

Val Phe Pro Cys Pro Lys Asp Gly Arg Thr Ser Pro Glu Asp Ser Thr
                85                  90                  95

Gly Ser Cys Lys Lys Ser Ser Ala Lys Asp Arg Ile Gly Cys Asn Lys
            100                 105                 110

Lys Arg Lys Ile Ser Ala Lys Thr Val Lys Glu Thr Ser Thr Leu Ala
        115                 120                 125

Asp Asp Gly His Val Trp Arg Lys Tyr Gly Gln Lys Gln Ile Leu Asp
130                 135                 140

Ala Pro Tyr Pro Arg His Tyr Tyr Arg Cys Thr Asn Lys Phe Asp Gln
145                 150                 155                 160

Gly Cys Glu Ala Ile Lys Gln Val Gln Arg Ile Gln Asp Asn Pro Pro
                165                 170                 175

Gln Phe Arg Thr Ile Tyr Gln Gly His His Thr Cys Thr Thr Tyr Pro
            180                 185                 190

Thr Ala Ser Gln Ile Leu Leu Asp Ser Ser Thr Asp Tyr Glu Asn Ser
        195                 200                 205

Ser Ile Leu Leu Ser Phe Asn Thr Lys Asp Asn His Tyr Tyr His Pro
210                 215                 220

Tyr Asn Phe Pro Thr Phe Phe Ser Thr Lys Lys Glu Thr Lys Glu Glu
225                 230                 235                 240

Asn Ser Pro Ser Phe Phe Tyr Pro Asn Asn Asn Gln Asn Gln Ile Ser
                245                 250                 255

Thr Ser Asp Tyr Ile Leu Pro Ala Asn Asp Tyr Trp Thr Pro Ala Thr
            260                 265                 270

Glu Thr Ser Gly Asn Val Met Ala Thr Ala Leu Ser Ser Ala Ser Asp
        275                 280                 285

Asn Val Asp Tyr Ile Ser Ser Glu Ser Val Thr Ser Thr His Asn Leu
290                 295                 300

Glu Met Glu Met Glu Met Glu Met Met Ala Gly Ile Asp Phe
305                 310                 315                 320

Asp Asp Leu Pro Phe Glu Phe
            325

<210> SEQ ID NO 22
<211> LENGTH: 726
<212> TYPE: PRT
<213> ORGANISM: Nicotiana tabacum

<400> SEQUENCE: 22

Met Asp Ala Ala Asn Leu Val Met Lys Ser Ser Leu Phe Ser Lys Ser
1               5                   10                  15

Pro Cys Pro Leu Phe Ser Ser Lys Leu Ile Pro Arg Ala Pro Pro Ser
            20                  25                  30

Val Phe Thr Leu Pro Ser Thr Phe Arg Pro Leu Val Lys Cys Ile Gln
        35                  40                  45

Ala Ser Phe Pro Pro Asn Pro Asp Ser Lys Lys Pro Ser Asn Asn Ser
    50                  55                  60

Thr Phe Thr Cys Ser Ala Val Thr Ser Phe Pro Ser Gln Gln Ser Gln
65                  70                  75                  80

Pro His Ala Pro Ser Asp Ala Lys Leu Gln Leu Leu Ile Ser Glu Phe
                85                  90                  95

Gln Ser Leu Val Glu Pro Met Asp Arg Val Lys Arg Leu Leu His Tyr
            100                 105                 110

Ser Thr Leu Leu Pro Pro Met Asp Ala Ser Phe Lys Thr Pro Glu Asn

-continued

```
            115                 120                 125
Arg Val Pro Gly Cys Thr Thr Gln Val Trp Leu Asn Val Ser Phe Asp
    130                 135                 140
Glu Ala Glu Asn Arg Met Lys Phe Leu Ala Asp Ser Asp Ser Glu Ile
145                 150                 155                 160
Thr Lys Gly Phe Cys Ala Cys Leu Val Ser Leu Leu Asp Gly Ala Thr
                165                 170                 175
Pro Asp Glu Val Leu Ala Leu Lys Thr Glu Asp Leu Asn Ala Leu Asn
            180                 185                 190
Val Ala Gly Leu Asn Gly Lys Gly Ser Ala Ser Arg Ala Asn Thr Trp
        195                 200                 205
His Asn Val Leu Val Ser Met Gln Lys Arg Thr Arg Ala Leu Val Ala
    210                 215                 220
Glu Arg Glu Gly Arg Pro Arg Gly Glu Leu Phe Pro Ser Leu Val Ile
225                 230                 235                 240
Thr Ala Asp Gly Ile Gln Pro Gln Gly Ser Tyr Ala Glu Ala Gln Ala
                245                 250                 255
Arg Phe Leu Phe Pro Asp Glu Ser Arg Val Gln Lys Leu Ala Asn Leu
            260                 265                 270
Leu Lys Glu Lys Lys Ile Gly Val Ala His Phe Tyr Met Asp Pro
        275                 280                 285
Glu Val Gln Gly Val Leu Thr Ala Ala Gln Lys Leu Trp Pro His Ile
    290                 295                 300
His Ile Ser Asp Ser Leu Val Met Ala Asp Lys Ala Val Ser Met Ala
305                 310                 315                 320
Lys Ala Gly Cys Glu Tyr Ile Ser Val Leu Gly Val Asp Phe Met Ser
                325                 330                 335
Glu Asn Val Arg Ala Ile Leu Asp Leu Ala Gly Phe Pro Glu Val Gly
            340                 345                 350
Val Tyr Arg Met Ser Asp Glu Arg Ile Gly Cys Ser Leu Ala Asp Ala
        355                 360                 365
Ala Ala Ser Pro Ala Tyr Leu Asp Tyr Leu Lys Thr Ala Ser Thr Ser
    370                 375                 380
Ser Pro Ser Leu His Val Val Tyr Ile Asn Thr Ser Leu Glu Thr Lys
385                 390                 395                 400
Ala Tyr Ser His Glu Leu Val Pro Thr Ile Thr Cys Thr Ser Ser Asn
                405                 410                 415
Val Val Gln Thr Ile Leu Gln Ala Phe Ala Glu Val Pro Asp Leu Glu
            420                 425                 430
Val Leu Tyr Gly Pro Asp Thr Tyr Met Gly Ser Asn Ile Ala Glu Leu
        435                 440                 445
Phe Thr Gln Met Ser Thr Met Thr Asp Glu Glu Ile Ser Ala Ile His
    450                 455                 460
Pro Leu His Asn Arg Ile Ser Ile Lys Ser Leu Leu Pro Arg Leu His
465                 470                 475                 480
Tyr Phe Gln Asp Gly Thr Cys Ile Val His His Leu Phe Gly His Glu
                485                 490                 495
Val Val Glu Lys Ile Asn Glu Met Tyr Gly Asp Ala Phe Leu Thr Ala
            500                 505                 510
His Phe Glu Val Pro Gly Glu Met Phe Ser Leu Ala Met Glu Ala Lys
        515                 520                 525
Lys Arg Gly Met Gly Val Val Gly Ser Thr Ser Asn Ile Leu Asp Phe
    530                 535                 540
```

```
Ile Lys Glu Arg Val Glu Glu Ser Leu Asn Arg Asn Val Asp Glu His
545                 550                 555                 560

Leu Gln Phe Val Leu Gly Thr Glu Ser Gly Met Ile Thr Ala Ile Val
                565                 570                 575

Ala Ala Val Gly Lys Leu Leu Gly Ser Ala Asp Ser Ser Ser Gly Gly
            580                 585                 590

Ala Lys Val Ser Val Glu Ile Val Phe Pro Val Ser Ser Glu Ser Val
        595                 600                 605

Thr Arg Thr Ser Thr Gly Ser Pro Leu Asp Gln Asn Lys Val Asn Ile
    610                 615                 620

Ile Pro Gly Val Ala Ser Gly Glu Gly Cys Ser Leu His Gly Gly Cys
625                 630                 635                 640

Ala Ser Cys Pro Tyr Met Lys Met Asn Ser Leu Ser Ser Leu Leu Lys
                645                 650                 655

Val Cys Gln Ser Leu Pro His Gly Lys Ala Glu Leu Ser Ala Tyr Glu
                660                 665                 670

Ala Gly Arg Phe Ser Leu Arg Thr Pro Lys Gly Lys Gln Ile Ala Asp
            675                 680                 685

Val Gly Cys Glu Pro Val Leu His Met Arg His Phe Gln Ala Thr Lys
        690                 695                 700

Arg Leu Pro Glu Gln Leu Ile Asn Gln Ile Leu Gln Pro Arg Asp Asn
705                 710                 715                 720

Gly Arg Ser Ser Ser Ala
                725

<210> SEQ ID NO 23
<211> LENGTH: 721
<212> TYPE: PRT
<213> ORGANISM: Nicotiana tabacum

<400> SEQUENCE: 23

Met Asp Ala Ala Asn Leu Val Met Lys Ser Ser Met Phe Ser Lys Ser
1               5                   10                  15

Pro Cys Pro Val Phe Gly Ser Lys Leu Ile Pro Arg Ala Pro Pro Ser
            20                  25                  30

Val Phe Thr Leu Pro Ser Thr Phe Arg Pro Leu Val Lys Cys Ile Gln
        35                  40                  45

Ala Ser Phe Pro Gln Asn Pro Asp Ser Lys Ile Pro Ser Asn Asn Ser
    50                  55                  60

Thr Phe Thr Cys Ser Ala Val Thr Ser Phe Pro Ser Gln Gln Ser Gln
65                  70                  75                  80

Pro His Ala Thr Ser Asp Ala Lys Leu Gln Leu Leu Ile Ser Glu Phe
                85                  90                  95

Gln Ser Leu Val Glu Pro Met Asp Arg Val Lys Arg Leu Leu His Tyr
                100                 105                 110

Ser Thr Leu Ile Pro Ser Met Asp Ala Ser Leu Lys Thr Pro Glu Asn
            115                 120                 125

Arg Val Leu Gly Cys Thr Thr Gln Val Trp Leu His Val Ser Phe Asp
        130                 135                 140

Glu Ala Glu Asn Arg Met Lys Phe Val Ala Asp Ser Asp Ser Asp Ile
145                 150                 155                 160

Thr Lys Gly Phe Cys Ala Cys Leu Val Ser Leu Leu Asp Gly Ala Thr
                165                 170                 175

Pro Asp Glu Val Leu Ala Leu Lys Thr Glu Asp Leu Asn Ala Leu Asn
```

-continued

```
                180                 185                 190
Val Ala Gly Leu Asn Gly Lys Gly Ser Ala Ser Arg Ala Asn Thr Trp
                195                 200                 205
His Asn Val Leu Val Ser Met Gln Lys Arg Thr Arg Ala Leu Val Ala
                210                 215                 220
Glu Arg Glu Gly Arg Pro Arg Asn Glu Leu Phe Pro Ser Leu Val Ile
225                 230                 235                 240
Thr Ala Asp Gly Ile Gln Pro Gln Gly Ser Tyr Ala Glu Ala Gln Ala
                245                 250                 255
Arg Phe Leu Phe Pro Asp Glu Ser Arg Val Gln Glu Leu Ala Ser Leu
                260                 265                 270
Leu Lys Glu Lys Lys Ile Gly Val Ala His Phe Tyr Met Asp Pro
        275                 280                 285
Glu Val Gln Gly Val Leu Thr Ala Ala Gln Lys Leu Trp Pro His Ile
        290                 295                 300
His Ile Ser Asp Ser Leu Val Met Ala Asp Lys Ala Val Ser Met Ala
305                 310                 315                 320
Lys Ala Gly Cys Glu Tyr Ile Ser Val Leu Gly Val Asp Phe Met Ser
                325                 330                 335
Glu Asn Val Arg Ala Ile Leu Asp Leu Ala Gly Phe Pro Glu Val Gly
                340                 345                 350
Val Tyr Arg Met Ser Asp Glu Arg Ile Gly Cys Ser Leu Ala Asp Ala
                355                 360                 365
Ala Ala Ser Pro Ala Tyr Leu Asp Tyr Leu Lys Thr Ala Ser Thr Ser
        370                 375                 380
Ser Pro Ser Leu His Val Val Tyr Ile Asn Thr Ser Leu Glu Thr Lys
385                 390                 395                 400
Ala Tyr Ser His Glu Leu Val Pro Thr Ile Thr Cys Thr Ser Ser Asn
                405                 410                 415
Val Val Gln Thr Ile Leu Gln Ala Phe Ala Glu Val Pro Asp Leu Glu
                420                 425                 430
Val Leu Tyr Gly Pro Asp Thr Tyr Met Gly Ser Asn Ile Ala Glu Leu
                435                 440                 445
Phe Thr Gln Met Ser Thr Met Thr Asp Glu Glu Ile Ser Glu Ile His
        450                 455                 460
Pro Leu His Asn Arg Ser Ser Ile Lys Ser Leu Leu Pro Arg Leu His
465                 470                 475                 480
Tyr Phe Gln Asp Gly Thr Cys Ile Val His His Leu Phe Gly His Glu
                485                 490                 495
Val Val Glu Asn Ile Asn Glu Met Tyr Gly Asp Ala Phe Leu Thr Ala
                500                 505                 510
His Phe Glu Val Pro Gly Glu Met Phe Ser Leu Ala Met Glu Ala Lys
        515                 520                 525
Lys Arg Gly Met Gly Val Val Gly Ser Thr Ser Asn Ile Leu Asp Phe
        530                 535                 540
Ile Lys Glu Arg Val Glu Glu Ala Leu Asn Arg Asn Val Asp Glu His
545                 550                 555                 560
Leu Gln Phe Val Leu Gly Thr Glu Ser Gly Met Ile Thr Ala Ile Val
                565                 570                 575
Ala Ala Val Gly Lys Leu Leu Gly Ser Ala Asp Thr Ser Ser Gly Gly
                580                 585                 590
Ala Lys Val Ser Val Glu Ile Val Phe Pro Val Ser Ser Glu Ser Val
        595                 600                 605
```

```
Thr Arg Thr Ser Thr Gly Ser Ser Leu Asp Gln Asn Lys Val Asn Ile
            610                 615                 620
Ile Pro Gly Val Ala Ser Gly Glu Gly Cys Ser Leu His Gly Gly Cys
625                 630                 635                 640
Ala Ser Cys Pro Tyr Met Lys Met Asn Ser Leu Ser Ser Leu Leu Arg
                645                 650                 655
Val Cys Gln Ser Leu Pro His Gly Lys Ala Glu Leu Ser Ala Tyr Glu
            660                 665                 670
Ala Gly Arg Phe Ser Leu Gln Thr Pro Asn Gly Lys Gln Ile Ala Asp
            675                 680                 685
Val Gly Cys Glu Pro Val Leu His Met Arg His Phe Gln Ala Thr Lys
            690                 695                 700
Arg Leu Pro Glu Gln Leu Ile Asn Gln Ile Leu Gln Arg Ser Ser Ser
705                 710                 715                 720
Ala

<210> SEQ ID NO 24
<211> LENGTH: 290
<212> TYPE: PRT
<213> ORGANISM: Nicotiana tabacum

<400> SEQUENCE: 24

Met Ala Leu Pro Gln Glu Asn Cys Thr Thr Leu Asp Leu Ile Arg Gln
1               5                   10                  15
His Leu Leu Asp Asp Asn Val Phe Met Glu His Tyr Cys Pro Gln Pro
            20                  25                  30
Ile Leu Tyr Ser Gln Ser Ser Ser Ser Glu Ser Leu Asn Ser Ile
            35                  40                  45
Ala Ser Glu Leu Asn Asn Asp Thr Phe Ser Phe Glu Pro Thr Leu Asn
50                  55                  60
Tyr Ala Asp Thr Ala Gln Ser Ser Asn Leu Asp Ile Ser Thr Phe Phe
65                  70                  75                  80
Asn Asn Ser Lys Thr Glu Phe Asp Cys Phe Glu Phe Glu Thr Lys Pro
                85                  90                  95
Asn Val Leu Ala Ala Arg Ile Ser Pro Asn Ser Pro Lys Gln Thr Ser
            100                 105                 110
Phe Lys Glu Arg Lys Pro Ser Leu Asn Ile Ala Ile Pro Leu Lys His
            115                 120                 125
Gln Glu Val Val Gln Lys Val Glu Lys Ser Asn Glu Ser Glu Lys Lys
130                 135                 140
His Tyr Arg Gly Val Arg Gln Arg Pro Trp Gly Lys Phe Ala Ala Glu
145                 150                 155                 160
Ile Arg Asp Pro Asn Arg Lys Gly Thr Arg Val Trp Leu Gly Thr Phe
                165                 170                 175
Asp Thr Ala Leu Glu Ala Ala Lys Ala Tyr Asp Arg Ala Ala Phe Glu
            180                 185                 190
Leu Arg Gly Ser Lys Ala Ile Val Asn Phe Pro Leu Glu Val Ala Asn
            195                 200                 205
Phe Lys Gln Glu Phe Asn Asn Glu Ile Arg Pro Leu Val Asn Ser Ser
210                 215                 220
Arg Lys Arg Val Arg Glu Thr Val Asn Glu Glu Gln Leu Val Ile Asn
225                 230                 235                 240
Lys Glu Met Lys Ile Glu Glu Arg Val Pro Thr Ala Pro Leu Thr
                245                 250                 255
```

```
Pro Ser Ile Trp Ser Ala Ile Trp Asp Ser Gly Asp Gly Lys Gly Ile
            260                 265                 270

Phe Glu Val Pro Pro Leu Ser Pro His Met Ala Tyr Ser Gln Leu Val
            275                 280                 285

Met Ile
    290

<210> SEQ ID NO 25
<211> LENGTH: 276
<212> TYPE: PRT
<213> ORGANISM: Nicotiana tabacum

<400> SEQUENCE: 25

Met Ala Ser Pro Gln Glu Asn Cys Thr Thr Leu Asp Leu Ile Arg Gln
1               5                   10                  15

His Leu Phe Asp Asp Ala Ala Phe Met Glu Tyr Tyr Cys Ser Glu Pro
            20                  25                  30

Thr Thr Leu Tyr Ser Gln Asn Ser Ser Ser Glu Ser Leu Asp Gln
        35                  40                  45

Ser Phe Ser Phe Glu Pro Thr Leu Asn Tyr Ala Asp Thr Ala Gln Ser
    50                  55                  60

Ser Ser Phe Glu Ile Ser Ser Phe Phe Asp Asn Ser Lys Thr Glu Phe
65                  70                  75                  80

Asp Cys Ser Glu Leu Glu Thr Ile Gln Lys Gln Ser Leu Asn Ser Arg
                85                  90                  95

Lys Gln Thr Ser Phe Lys Glu Arg Lys Pro Ser Leu Asn Ile Ala Ile
            100                 105                 110

Pro Val Lys Gln Gln Lys Val Glu Val Val Pro Arg Gly Lys Lys His
            115                 120                 125

Tyr Arg Gly Val Arg Gln Arg Pro Trp Gly Lys Phe Ala Ala Glu Ile
    130                 135                 140

Arg Asp Pro Asn Arg Lys Gly Thr Arg Val Trp Leu Gly Thr Phe Asp
145                 150                 155                 160

Thr Ala Leu Glu Ala Ala Lys Ala Tyr Asp Arg Ala Ala Phe Lys Leu
                165                 170                 175

Arg Gly Asn Lys Ala Ile Val Asn Phe Pro Leu Glu Val Ala Asn Phe
            180                 185                 190

Lys Gln Glu Tyr Asn Asn Glu Ile Pro Gln Ser Ala Asn Ser Gly Arg
        195                 200                 205

Lys Arg Val Arg Glu Thr Glu Asn Glu Glu Leu Val Ile Asn Lys
    210                 215                 220

Glu Met Lys Ile Glu Glu Glu Arg Val Pro Thr Thr Pro Leu Thr Pro
225                 230                 235                 240

Ser Ser Trp Ser Ala Ile Trp Asp Ser Gly Asp Gly Lys Gly Ile Phe
                245                 250                 255

Glu Met Pro Leu Leu Ser Pro Leu Ser Pro His Leu Pro Tyr Ser Gln
            260                 265                 270

Leu Val Ile Ile
        275

<210> SEQ ID NO 26
<211> LENGTH: 277
<212> TYPE: PRT
<213> ORGANISM: Nicotiana tabacum

<400> SEQUENCE: 26
```

```
Met Ala Ser Pro Gln Glu Asn Cys Thr Leu Asp Leu Ile Arg Gln His
1               5                   10                  15

Leu Phe Asp Asp Ala Phe Met Glu Cys Tyr Cys Ser Glu Pro Thr
            20                  25                  30

Thr Leu Asp Ser Gln Asn Ser Ser Ser Glu Ser Leu Asp Gln Ser
            35                  40                  45

Phe Ser Phe Glu Pro Thr Leu Asn Tyr Ala Asp Thr Ala Gln Ser Ser
50                      55                  60

Ser Phe Glu Ile Ser Ser Phe Phe Asp Asn Ser Lys Thr Glu Phe Asp
65                  70                  75                  80

Cys Phe Glu Leu Glu Thr Ile Gln Lys Gln Ser Leu Asn Ser Arg Lys
                85                  90                  95

Gln Thr Ser Phe Lys Glu Arg Lys Pro Ser Leu Asn Ile Ala Ile Pro
                100                 105                 110

Val Lys Leu Gln Lys Val Glu Val Pro Ser Glu Lys Lys His Tyr
            115                 120                 125

Arg Gly Val Arg Gln Arg Pro Trp Gly Lys Phe Ala Ala Glu Ile Arg
130                     135                 140

Asp Pro Asn Arg Lys Gly Thr Arg Val Trp Leu Gly Thr Phe Asp Thr
145                 150                 155                 160

Ala Ile Glu Ala Ala Lys Ala Tyr Asp Arg Ala Ala Phe Lys Leu Arg
                165                 170                 175

Gly Ser Lys Ala Ile Val Asn Phe Pro Leu Glu Val Ala Asn Phe Lys
                180                 185                 190

Gln Glu Tyr Asn Asn Glu Ile Pro Gln Ser Ala Asn Ser Gly Arg Lys
                195                 200                 205

Arg Val Arg Gly Thr Glu Asn Glu Gln Leu Val Ile Asn Lys Glu
            210                 215                 220

Met Lys Arg Glu Glu Gly Arg Val Pro Thr Ala Ala Pro Leu Thr
225                 230                 235                 240

Pro Ser Ser Trp Ser Ala Ile Trp Asp Ser Gly Asp Gly Lys Gly Ile
                245                 250                 255

Phe Glu Val Pro Pro Leu Ser Pro Leu Ser Pro His Ile Gly Tyr Ser
            260                 265                 270

Gln Val Val Met Ile
        275

<210> SEQ ID NO 27
<211> LENGTH: 70
<212> TYPE: PRT
<213> ORGANISM: Nicotiana tabacum

<400> SEQUENCE: 27

Asp Asp Ser Leu Ser Leu Arg Lys Ala Leu Ile Val Cys Arg Val Ile
1               5                   10                  15

Ala Gly Arg Val His Arg Pro Leu Glu Asn Val Gln Glu Leu Ile Gly
            20                  25                  30

Gln Ser Gly Phe Asp Ser Leu Ala Gly Lys Val Gly Leu Tyr Ser Asn
            35                  40                  45

Ile Glu Glu Leu Tyr Leu Leu Asn Ser Lys Ala Leu Leu Pro Cys Phe
            50                  55                  60

Val Val Ile Cys Lys Ser
65                  70
```

```
<210> SEQ ID NO 28
<211> LENGTH: 132
<212> TYPE: PRT
<213> ORGANISM: Nicotiana tabacum

<400> SEQUENCE: 28

Met Arg Arg Asn Cys Asn Leu Glu Leu Arg Leu Met Pro Pro Ser Phe
1               5                   10                  15

Ser Phe Ser Pro Lys Asn Cys Thr Thr Pro Tyr Phe Ser Thr Asp Arg
            20                  25                  30

Glu Asp Lys Glu Ser Thr Glu Glu Lys Gln Pro Gln Gln Leu Thr Ile
        35                  40                  45

Phe Tyr Asn Gly Lys Phe Val Val Ser Asp Ala Thr Glu Leu Gln Ala
    50                  55                  60

Lys Ala Ile Ile Tyr Leu Ala Ser Arg Glu Met Glu Glu Lys Thr Lys
65                  70                  75                  80

Ile Arg Ser Pro Ile Ser Glu Ser Ser Ser Pro Ile Ser Glu Pro Ser
                85                  90                  95

Ser Pro Phe Leu Gln Ser Pro Ala Ser Asp Leu Ser Met Lys Arg Ser
            100                 105                 110

Leu Gln Arg Phe Leu Gln Lys Arg Lys Asn Arg Ile Gln Ala Thr Ser
        115                 120                 125

Pro Tyr His His
    130

<210> SEQ ID NO 29
<211> LENGTH: 393
<212> TYPE: PRT
<213> ORGANISM: Nicotiana tabacum

<400> SEQUENCE: 29

Met Glu Arg Asp Phe Met Gly Leu Thr His His Val Lys Gln Glu Val
1               5                   10                  15

Thr Glu Glu Pro Ile Asp Pro Ala Pro Leu Arg Ser Ser Ala Met Gln
            20                  25                  30

Trp Ser Phe Ser Asn Asn Ile Ser Thr His Pro Gln Tyr Leu Ser Phe
            35                  40                  45

Lys Gly Ala Gln Glu Asp Arg Pro Lys Thr Gly Phe Asp Ser Leu Ala
    50                  55                  60

Ser Thr Gly Leu Val Thr Ile Thr Thr Thr Glu Ala Val Asp Ser Ser
65                  70                  75                  80

His Arg Ser Tyr Ser Gly Val Gly Gln Lys Asn Met Met Leu Glu Lys
                85                  90                  95

Gln Gly Gly Thr His Tyr Met Ser Thr Thr Phe Ser Pro His His Tyr
            100                 105                 110

Asp Ala His Ala Met His Arg Ser His Gly Val Arg Val Leu Pro Val
        115                 120                 125

Ser Asn Pro Ala Asn Gln Ile Ser Val Ser Met Thr Met Pro Gly His
    130                 135                 140

Lys Ser Phe Val Ser Pro Leu Gly Gln Asn Pro Val Ala Ser Pro Ile
145                 150                 155                 160

Ser Ala Val Pro Thr Asn Ser Ala Val Val Gly Thr Thr Asp Leu Arg
                165                 170                 175

Gly Ala Pro Lys Thr Pro Pro Gly Pro Ala Gln Leu Thr Ile Phe Tyr
            180                 185                 190

Ala Gly Ser Val Cys Val Tyr Asp Asn Val Ser Pro Glu Lys Ala Gln
```

```
            195                 200                 205
Ala Ile Met Leu Leu Ala Gly Asn Ala Pro Val Thr Pro Ser Ala
210                 215                 220

Thr Ser Ala Leu Ser Pro Val Gln Ala Pro Ile Pro Lys Ser Ser
225                 230                 235                 240

Val Asp Ser Phe Val Val Asn Gln Ser His Asn Thr Thr Pro Thr Leu
                    245                 250                 255

Pro Ser Pro Ile Ser Ile Thr Ser His Cys Gly Ser Gln Ser Ala Gly
                260                 265                 270

Val Ser Ser Asn Thr Asn Gly Val Thr Ile Ile Lys Ser Ile Gly Val
            275                 280                 285

Leu Pro Ser Pro Ser Asn Lys Ala Glu Leu Ser Lys Phe Ser Ser Ser
        290                 295                 300

Ile Gly Ser Val Pro Ala Thr Phe Val Gln Ser Ala Val Pro Gln Ala
305                 310                 315                 320

Arg Lys Ala Ser Leu Ala Arg Phe Leu Glu Lys Arg Lys Glu Arg Val
                325                 330                 335

Ile Ser Ala Ser Pro Tyr Val Ser Cys Lys Gln Ser Pro Glu Cys Ser
                340                 345                 350

Thr Leu Gly Tyr Gly Ser Arg Ser Phe Ala Lys Asp Ser Leu Gly Ser
            355                 360                 365

Phe Pro Pro Pro Cys Asn Gln Phe Gly Gln Gly Asp Val Lys Cys Gln
        370                 375                 380

Gln Trp Gln Asn Asn Val Asp Thr Arg
385                 390

<210> SEQ ID NO 30
<211> LENGTH: 269
<212> TYPE: PRT
<213> ORGANISM: Nicotiana tabacum

<400> SEQUENCE: 30

Met Ser Ile Pro Phe Glu His Asp Tyr Ile Gly Leu Ser Glu Ala Ser
1               5                   10                  15

Leu Met Glu Arg Asn Ser Asp Lys Asn Ser Asp Val Leu Asn Leu Lys
                20                  25                  30

Glu Thr Glu Leu Arg Leu Gly Leu Pro Gly Thr Glu Glu Thr Asn Thr
            35                  40                  45

Gly Leu Asn Pro Ser Asn Asn Phe Ile Ser Arg Thr Lys Arg Gly Phe
    50                  55                  60

Ser Asp Ala Ile Asp Ala Ser Gly Lys Trp Asp Leu Ser Ile Asn Cys
65                  70                  75                  80

Arg Ser Glu Thr Asp Trp Arg Lys Glu Asp Leu Leu Phe Ser Pro Lys
                85                  90                  95

Gly Ser Asn Gly Ser Ser Lys Pro Thr Pro Ser Ile Glu Asn Ser Ala
            100                 105                 110

Pro Gln Thr Ser Lys Ala Gln Val Gly Trp Pro Pro Ile Arg Ser
        115                 120                 125

Phe Arg Lys Asn Thr Leu Ala Thr Lys Lys Asn Asp Ala Glu Gly Lys
    130                 135                 140

Ser Gly Ser Gly Cys Leu Tyr Val Lys Val Arg Met Asp Gly Ala Pro
145                 150                 155                 160

Tyr Leu Arg Lys Val Asp Ile Lys Thr Tyr Ser Asp Tyr Gly Glu Leu
                165                 170                 175
```

```
Ser Ser Ala Leu Glu Lys Met Phe Ser Cys Phe Ser Ile Gly Gln Cys
            180                 185                 190

Ala Ser Asp Gly Leu Pro Gly Gln Glu Glu Leu Ser Glu Ser His Leu
        195                 200                 205

Met Asp Leu Leu Asn Gly Ser Glu Tyr Val Leu Thr Tyr Glu Asp Lys
    210                 215                 220

Asp Gly Asp Trp Met Leu Val Gly Asp Val Pro Trp Glu Met Phe Ile
225                 230                 235                 240

Asp Ser Cys Lys Arg Leu Arg Ile Met Lys Ser Ser Glu Ala Ile Gly
                245                 250                 255

Leu Ala Pro Arg Ala Ile His Lys Cys Lys Asn Lys Asn
                260                 265
```

<210> SEQ ID NO 31
<211> LENGTH: 50
<212> TYPE: PRT
<213> ORGANISM: Nicotiana tabacum

<400> SEQUENCE: 31

```
Met Ile His Arg Lys Trp Ser Leu Leu Thr Gly Pro Ala Ala Ile Leu
1               5                   10                  15

Gly Gly Ile Val Gly Thr Ile Val Val Ala Asn Phe Ile Phe Val Gln
            20                  25                  30

Asn Asp Pro Phe Leu Lys Pro Asp Arg Lys Gln Glu Lys Ala Pro Ser
        35                  40                  45

Asn Lys
    50
```

<210> SEQ ID NO 32
<211> LENGTH: 100
<212> TYPE: PRT
<213> ORGANISM: Nicotiana tabacum

<400> SEQUENCE: 32

```
Met Ala Thr Ala Met Phe Arg Ser Ser Ile Arg Ser Ala Leu Arg Ser
1               5                   10                  15

Gly Ala Pro Arg Val Thr Pro Ala Ser Lys Arg Thr Phe Ser Ser His
            20                  25                  30

Ser Ser Val Glu Glu Glu Ala Arg Glu Ala Ser Lys Trp Glu Lys Ile
        35                  40                  45

Thr Tyr Val Gly Ile Val Ser Cys Ser Ile Leu Ala Ala Ile Cys Leu
    50                  55                  60

Ser Lys Gly His Pro His Ser Asp Glu Pro Pro Ala Tyr Ser Tyr Leu
65                  70                  75                  80

His Ile Arg Asn Lys Glu Phe Pro Trp Gly Pro Asp Gly Leu Phe Glu
                85                  90                  95

Val Lys His His
        100
```

<210> SEQ ID NO 33
<211> LENGTH: 90
<212> TYPE: DNA
<213> ORGANISM: Nicotiana tabacum

<400> SEQUENCE: 33
taaggttaaa tcttttttta tcataatact catcaaatct aagagacaca gagctcatta    60
atagcccgtt tggccaagct gcaaaaatca                                    90

```
<210> SEQ ID NO 34
<211> LENGTH: 72
<212> TYPE: DNA
<213> ORGANISM: Artificial Sequence
<220> FEATURE:
<223> OTHER INFORMATION: Synthetic DNA

<400> SEQUENCE: 34
actaataatt gcaccgagac aaacactaat aattgcaccg agacaaacac taataattgc      60
accgagacaa ac                                                         72

<210> SEQ ID NO 35
<211> LENGTH: 28
<212> TYPE: DNA
<213> ORGANISM: Nicotiana tabacum

<400> SEQUENCE: 35
caccacaaga tacaattgca gctgctac                                        28

<210> SEQ ID NO 36
<211> LENGTH: 26
<212> TYPE: DNA
<213> ORGANISM: Nicotiana tabacum

<400> SEQUENCE: 36
ggctaaagca atgacttcag taagcg                                          26

<210> SEQ ID NO 37
<211> LENGTH: 26
<212> TYPE: DNA
<213> ORGANISM: Nicotiana tabacum

<400> SEQUENCE: 37
caccattgct tacataactg agatgc                                          26

<210> SEQ ID NO 38
<211> LENGTH: 30
<212> TYPE: DNA
<213> ORGANISM: Nicotiana tabacum

<400> SEQUENCE: 38
acgatatgat tcttcactac actttatgcc                                      30

<210> SEQ ID NO 39
<211> LENGTH: 28
<212> TYPE: DNA
<213> ORGANISM: Nicotiana tabacum

<400> SEQUENCE: 39
caccgcatca agtgctgaaa acatagcc                                        28

<210> SEQ ID NO 40
<211> LENGTH: 29
<212> TYPE: DNA
<213> ORGANISM: Nicotiana tabacum

<400> SEQUENCE: 40
cactaatgtt aaaacagtca tacctggcc                                       29

<210> SEQ ID NO 41
<211> LENGTH: 30
<212> TYPE: DNA
<213> ORGANISM: Nicotiana tabacum
```

```
<400> SEQUENCE: 41
caccattatt accatcctta taattttccc                                       30

<210> SEQ ID NO 42
<211> LENGTH: 29
<212> TYPE: DNA
<213> ORGANISM: Nicotiana tabacum

<400> SEQUENCE: 42
gaacttatcc tgaatctacc tatactccc                                        29

<210> SEQ ID NO 43
<211> LENGTH: 26
<212> TYPE: DNA
<213> ORGANISM: Nicotiana tabacum

<400> SEQUENCE: 43
caccgagcaa tgattcaagt atgggg                                           26

<210> SEQ ID NO 44
<211> LENGTH: 26
<212> TYPE: DNA
<213> ORGANISM: Nicotiana tabacum

<400> SEQUENCE: 44
cgatgtctac tacacagaga attgcc                                           26

<210> SEQ ID NO 45
<211> LENGTH: 29
<212> TYPE: DNA
<213> ORGANISM: Nicotiana tabacum

<400> SEQUENCE: 45
caccatcgtc ggaatttcaa tttgctacc                                        29

<210> SEQ ID NO 46
<211> LENGTH: 28
<212> TYPE: DNA
<213> ORGANISM: Nicotiana tabacum

<400> SEQUENCE: 46
attgttgaga agggaaggaa gtcacagc                                         28

<210> SEQ ID NO 47
<211> LENGTH: 26
<212> TYPE: DNA
<213> ORGANISM: Nicotiana tabacum

<400> SEQUENCE: 47
caccatcttg cctaccgcca ttttcc                                           26

<210> SEQ ID NO 48
<211> LENGTH: 28
<212> TYPE: DNA
<213> ORGANISM: Nicotiana tabacum

<400> SEQUENCE: 48
tgtatgcatt taacgagggg tctaaagg                                         28

<210> SEQ ID NO 49
<211> LENGTH: 28
<212> TYPE: DNA
```

```
<213> ORGANISM: Nicotiana tabacum

<400> SEQUENCE: 49
caccaagaat ttaataatga gattcggc                                         28

<210> SEQ ID NO 50
<211> LENGTH: 27
<212> TYPE: DNA
<213> ORGANISM: Nicotiana tabacum

<400> SEQUENCE: 50
atcgaacaaa ttgttaaact cactgcg                                          27

<210> SEQ ID NO 51
<211> LENGTH: 29
<212> TYPE: DNA
<213> ORGANISM: Nicotiana tabacum

<400> SEQUENCE: 51
caccaagttc gcagcagaaa ttcgtgacc                                        29

<210> SEQ ID NO 52
<211> LENGTH: 28
<212> TYPE: DNA
<213> ORGANISM: Nicotiana tabacum

<400> SEQUENCE: 52
tacacatctt ctattgagtc ctaatccc                                         28

<210> SEQ ID NO 53
<211> LENGTH: 26
<212> TYPE: DNA
<213> ORGANISM: Nicotiana tabacum

<400> SEQUENCE: 53
tataataatg agattccaca gtcggc                                           26

<210> SEQ ID NO 54
<211> LENGTH: 31
<212> TYPE: DNA
<213> ORGANISM: Nicotiana tabacum

<400> SEQUENCE: 54
aataaatacg taggttttag taggtatatg c                                     31

<210> SEQ ID NO 55
<211> LENGTH: 30
<212> TYPE: DNA
<213> ORGANISM: Nicotiana tabacum

<400> SEQUENCE: 55
caccgatgat agtttatctt tgagaaaggc                                       30

<210> SEQ ID NO 56
<211> LENGTH: 30
<212> TYPE: DNA
<213> ORGANISM: Nicotiana tabacum

<400> SEQUENCE: 56
aacttcaatt gaattacatg aaagaatggc                                       30

<210> SEQ ID NO 57
<211> LENGTH: 30
```

```
<212> TYPE: DNA
<213> ORGANISM: Nicotiana tabacum

<400> SEQUENCE: 57
caccgaagat gagaagaaac tgtaacttgg                                          30

<210> SEQ ID NO 58
<211> LENGTH: 29
<212> TYPE: DNA
<213> ORGANISM: Nicotiana tabacum

<400> SEQUENCE: 58
ctggagattg taaaaatggt gatgaaggc                                           29

<210> SEQ ID NO 59
<211> LENGTH: 27
<212> TYPE: DNA
<213> ORGANISM: Nicotiana tabacum

<400> SEQUENCE: 59
cacccataac acaacaccta ctctccc                                             27

<210> SEQ ID NO 60
<211> LENGTH: 30
<212> TYPE: DNA
<213> ORGANISM: Nicotiana tabacum

<400> SEQUENCE: 60
tattgaagtc aaaacgacca ccaatttagc                                          30

<210> SEQ ID NO 61
<211> LENGTH: 30
<212> TYPE: DNA
<213> ORGANISM: Nicotiana tabacum

<400> SEQUENCE: 61
caccaaaggt tgatatcaaa acttacagcg                                          30

<210> SEQ ID NO 62
<211> LENGTH: 29
<212> TYPE: DNA
<213> ORGANISM: Nicotiana tabacum

<400> SEQUENCE: 62
cttcttaaac cagtgctttt cctttcagg                                           29

<210> SEQ ID NO 63
<211> LENGTH: 35
<212> TYPE: DNA
<213> ORGANISM: Nicotiana tabacum

<400> SEQUENCE: 63
caccgctata gtttataaaa ttaccaagaa cgtcg                                    35

<210> SEQ ID NO 64
<211> LENGTH: 29
<212> TYPE: DNA
<213> ORGANISM: Nicotiana tabacum

<400> SEQUENCE: 64
tacatcatca tatacatgtg acatacggg                                           29

<210> SEQ ID NO 65
```

```
<211> LENGTH: 31
<212> TYPE: DNA
<213> ORGANISM: Nicotiana tabacum

<400> SEQUENCE: 65
caccagaagc tgaaggagaa gagaatatcg g                              31

<210> SEQ ID NO 66
<211> LENGTH: 26
<212> TYPE: DNA
<213> ORGANISM: Nicotiana tabacum

<400> SEQUENCE: 66
aaacaggaga tgaccagttc ccaacc                                    26

<210> SEQ ID NO 67
<211> LENGTH: 28
<212> TYPE: DNA
<213> ORGANISM: Nicotiana tabacum

<400> SEQUENCE: 67
caccaagaga aatccctaaa tggcgacg                                  28

<210> SEQ ID NO 68
<211> LENGTH: 30
<212> TYPE: DNA
<213> ORGANISM: Nicotiana tabacum

<400> SEQUENCE: 68
agcacattgt aagtatacag caaaagatgg                                30

<210> SEQ ID NO 69
<211> LENGTH: 24
<212> TYPE: DNA
<213> ORGANISM: Escherichia coli

<400> SEQUENCE: 69
cacctacggc aaagtgtggg tcaa                                      24

<210> SEQ ID NO 70
<211> LENGTH: 20
<212> TYPE: DNA
<213> ORGANISM: Escherichia coli

<400> SEQUENCE: 70
tgtctggctt ttggctgtga                                           20

<210> SEQ ID NO 71
<211> LENGTH: 431
<212> TYPE: DNA
<213> ORGANISM: Nicotiana tabacum

<400> SEQUENCE: 71
accacaagat acaattgcag ctgctacaaa agcaataaca tccgacccaa attttcaatc    60
tgcattggct gttgctcttg catctatcat tggctcaggc agcggaaatc atgcaggtgg   120
tattgaagaa aaatctggtc taaatttgaa ggttaccgaa ccatttccag ttctttgcag   180
cttcccatct acctcaaaga aataatatat ccaattaact gttcttcaaa ttttttctgaa   240 taaatcgact tctacggcaa atagacaggc tgctagtaac tttcgcttgc tgaagtaaga   300
aactaattgc ggcgttaatt aatcagatgt aatatttttt ttatgatttg gaggtacgat   360
gtccaaagtg tagatatttt agtttgataa aactaattga cacttcgctt actgaagtca   420
```
ttgctttagc c                                                          431

<210> SEQ ID NO 72
<211> LENGTH: 460
<212> TYPE: DNA
<213> ORGANISM: Nicotiana tabacum

<400> SEQUENCE: 72
ccattgctta cataactgag atgcagaaaa aactaagaga catggaatcc gagagggagc      60
tgagattagg aagcacttca agggatgcaa tggctgcaga agacagcccg aattcagaga     120
ttcaaatccg tggacccgac atcaacgtag aagctgccaa tgatgaagtc attgtaaggg     180
tgagttgtcc tctggaaacc catccaatat caagagtcat ccaaacattc aaagatgcac     240
agatcaatgt tgttgaatca aaactttctg ccgggaatgg aactgtattt cacacatttg     300
tactcaagtc tagtggatct gaacagctga caaaggaaaa gttgctggct gcattttcca     360
gcgaatcaga ctcgctgagg caattttcac cggtagggca ataacagttt tatgttttat     420
gtagttgcta ggcataaagt gtagtgaaga atcatatcgt                           460

<210> SEQ ID NO 73
<211> LENGTH: 471
<212> TYPE: DNA
<213> ORGANISM: Nicotiana tabacum

<400> SEQUENCE: 73
cgcatcaagt gctgaaaaca tagccaaatt gcttaaacaa tggaccagaa gtgattcaac      60
aaacatttct gagcaatcga aagcttcatc aagtactcaa ctctcaagta ataacaatgc     120
caccaccgag gaatttgagt cactttccag tttcgattca tttgaacagt caaattcaga     180
tcaattttca cagagtttga cacttgaggc tggtaaatta cactgtgaaa ttagtaaaag     240
agaagtggat gatcaagtac ccttgtcagt aatgctggag agttggcttt ttgatgaaaa     300
tgacgatttg ctaatttaga aggaatttt ttgcttttcc atttggggat tctatttgtt      360
gcattatgtt tttgtttctt accccaagta ctagaatttt acctaggtat ggatgtgaca     420
tccacattct ttttttttt tgggccaggt atgactgttt taacattagt g               471

<210> SEQ ID NO 74
<211> LENGTH: 383
<212> TYPE: DNA
<213> ORGANISM: Nicotiana tabacum

<400> SEQUENCE: 74
cattattacc atccttataa ttttcccaca ttttttttcaa caaaaaaga aactaaagag       60 gaaaactccc caagtttctt ctaccctaat aacaaccaaa accaaatatc aacttccgac     120
tatattcttc cggccaatga ttattggact ccggcaactg aaacctccgg caatgttatg     180
gcgacggcgt tatcgtcggc gtctgataat gtggattaca tctcatctga atcagttact     240
agcactcaca atttggagat ggagatggag atggagatgg agatgatggc gggaattgac     300
tttgacgatt tgccttttga attttaaggg tagattttc tctcatattt ttttgggagt      360
ataggtagat tcaggataag ttc                                             383

<210> SEQ ID NO 75
<211> LENGTH: 372
<212> TYPE: DNA
<213> ORGANISM: Nicotiana tabacum

<400> SEQUENCE: 75

```
cgagcaatga ttcaagtatg ggggagtttg atgaatataa aatattcata tattatatac    60
ttaaaaatat actattttaa ataaagtatt tatataatat ttcgattctc tgtattttct   120
aacaatattt tgcaggagat aagaatgcta ttaattaagc aagaaaatga aagaatcaag   180
aagctcgtaa cggattcact ccataatgca agaagatcac gacgcatctt cttcatgacg   240
tatcttcctc gagatacatc ttcctcaaga catattctcc tcaagatgca tcttcctcac   300
ttgagatcac aacacttcaa gaagaaatgc acgtctataa atagaaggca attctctgtg   360
tagtagacat cg                                                       372
```

<210> SEQ ID NO 76
<211> LENGTH: 482
<212> TYPE: DNA
<213> ORGANISM: Nicotiana tabacum

<400> SEQUENCE: 76

```
ccatcgtcgg aatttcaatt tgctaccatt aatttgcaag gccctcctcc tcccgttccc    60
tttgtcctct cctctctctt ctgcacatcc aaatccaact tccctaccgc catttttccgc  120
acttcgataa ctcgttaacc cctcagtctc taatttcttc ctcaccccaa aaaaaaaaa   180
actttcattt ctctgtcttc tttccaaact ttttcttcc tccctgctt acacacaaga   240
atctgtgatg gatgccgcaa atttagtcat gaaatcttcc ttgttttcga atccccatg   300
tccccttttt agttctaaac tcattcctag agcaccaccc tctgtcttta ctctgccttc   360
tacctttaga cccctcgtta aatgcataca agcttcattc ccaccaaacc ctgattccaa   420
aaaccctca aacaattcaa cctttacgtg ttcagctgtg acttccttcc cttctcaaca   480
at                                                                 482
```

<210> SEQ ID NO 77
<211> LENGTH: 306
<212> TYPE: DNA
<213> ORGANISM: Nicotiana tabacum

<400> SEQUENCE: 77

```
ccatcttgcc taccgccatt ttccgcactt cgagaactcg ttaaccccctc actctccaat    60
ttcgtcctca cccaaaaaaa aaaaaaaaa aaccttgtca gttctctgtc ttcttttcaa   120
actcttttct tctttctcct ctgcttaaac acaagaatct gttatggacg ccgcaaattt   180
agtcatgaaa tctccatgt tttcgaaatc cccatgtccc gttttggttt ctaaactcat   240
tcctagagca ccacctctg tctttactct gccttctacc tttagacccc tcgttaaatg   300
cataca                                                             306
```

<210> SEQ ID NO 78
<211> LENGTH: 486
<212> TYPE: DNA
<213> ORGANISM: Nicotiana tabacum

<400> SEQUENCE: 78

```
aagaatttaa taatgagatt cggccattgg tgaactcaag caggaaaagg gtgagagaaa    60
cagtgaatga ggagcaacta gttatcaata aggaaatgaa aatagaagaa gaaagagtcc   120
cgacggctcc attaacgccg tcaatttggt cggcaatttg ggacagtgga gatgggaagg   180
gtattttga agtgccgcca ttatctccac atatggccta ttctcagctt gtcatgatat   240
aatcaataat ggataaggag tatataattt gggatgttag tatttggaag atgatgaata   300
```

```
tataaatatg cacctgacta tgaagaaagt ctgaggtgaa atcaagaatt aagatgagat      360
tcaataggaa gatgtagaac aataaaatag tccatggatg tgtctttggg tctttaatct      420
tttctgattt tattgattta gcgttatttc atgtaaatac gcagtgagtt taacaatttg      480
ttcgat                                                                 486

<210> SEQ ID NO 79
<211> LENGTH: 515
<212> TYPE: DNA
<213> ORGANISM: Nicotiana tabacum

<400> SEQUENCE: 79
caagttcgca gcagaaattc gtgacccgaa ccgaaagggg actcgggttt ggttaggaac       60
ctttgacact gccttagagg cggccaaggc atatgacagg gcagcgttta aacttagagg      120
aaacaaagca atagtgaatt tccctctcga agttgcaaac tttaagcaag aatataataa      180
tgagattcca cagtcagcta actcaggccg gaaaagggtg agagaaacag agaatgagga      240
gcaactcgtt atcaataagg aaatgaaaat agaagaagaa agagtcccta cgactccatt      300
aacgccgtca gttggtcgg cgatttggga cagtggagat gggaagggta tatttgagat       360
gccgctgctt tccccattgt ctccacattt gccttattct cagcttgtca ttatataatc      420
aaaaggacac cggtatatat acatatgcac ctgaccgtaa agaaagtctg aggtgattcc      480
ctgaattggg attaggactc aatagaagat gtgta                                 515

<210> SEQ ID NO 80
<211> LENGTH: 567
<212> TYPE: DNA
<213> ORGANISM: Escherichia coli

<400> SEQUENCE: 80
tataataatg agattccaca gtcggctaac tcaggccgga aagggtgag aggaacagag        60 aatgaggagc aattagttat caataaggaa atgaaaagag aagaagaaag agtccctact      120
gcggcggctc cattaacgcc gtcaagttgg tcggcgattt gggacagcgg agacggaaaa      180
ggaatttttg aggtgccgcc tctttcccca ttgtctccac atatagggta ttctcaggtt      240
gtgatgatat gatcagataa ggaacggcaa cgtatataga ttgtggtgtt agtatttagt      300
agatgaagga taaatattgc acctgactgt aaaaagtctg tggtgattaa tttctcagcc      360
aaaaaaagaa atatggggga aggtgggggt agctacggga attagtatgg tgataataaa      420
gattggtgtc tggtctcctc cttaagtctt ttgattaaat tttattgttt atgtaaaaac      480
gtcagtcaga gatctgtttg attgttttat atattcatat ctatgaaact atgaaagcat      540
atacctacta aaacctacgt atttatt                                          567

<210> SEQ ID NO 81
<211> LENGTH: 261
<212> TYPE: DNA
<213> ORGANISM: Nicotiana tabacum

<400> SEQUENCE: 81
gatgatagtt tatctttgag aaaggctcta atagtatgca gagtgattgc tggtagggtg       60
catagacctt tggaaaatgt tcaagaattg attggtcaat cagggtttga ttcattggct      120
ggaaaagtag gactctactc aaatattgaa gaactctatt tgctcaattc taaagctttg      180
cttccttgtt ttgtggtaat ctgtaaatca taaaaaatac aaggtgattg agccattctt      240
```
tcatgtaatt caattgaagt t                                          261

<210> SEQ ID NO 82
<211> LENGTH: 314
<212> TYPE: DNA
<213> ORGANISM: Nicotiana tabacum

<400> SEQUENCE: 82
gaagatgaga agaaactgta acttggagct caggcttatg cctccttctt tttcttttc    60 tcctaagaat tgcactaccc cttacttctc aacggatagg gaggataaag aaagcacaga  120
agagaaacaa ccacagcagc taacaatatt ttacaatgga aaatttgtgg tttctgatgc  180
tactgaactt caggctaaag caataatata tctggcaagt agagaaatgg aggagaaaac  240
aaaaatccgg tcaccaattt cagaatcatc atcaccaatt tcagagcctt catcaccatt  300
tttacaatct ccag                                                  314

<210> SEQ ID NO 83
<211> LENGTH: 493
<212> TYPE: DNA
<213> ORGANISM: Nicotiana tabacum

<400> SEQUENCE: 83
cccataacac aacacctact ctccccagcc ccatttctat aacatcccat tgtggatctc    60
aatctgctgg agtgtctagt aatacaaatg gagtaactat tatcaaatca attggggtcc  120
taccatctcc ttctaataaa gcagaacttt ctaaattttc cagttccata ggatctgttc  180
ctgccacctt tgttcaatca gctgtaccac aggcacgcaa ggcatcattg gctcggttct  240
tggagaagcg caaagaaagg gtaataagtg catcaccctta cgtcagctgc aagcaatccc  300
cagaatgcag cactcttgga tatggaagca gaagtttcgc aaaagattct ttaggctctt  360
ttcctccccc atgtaatcaa tttggtcaag agacgtgaa atgccaacag tggcaaaata  420
atgtagacac aaggtgaaga ctgtaccaga ttagattatt aaagctaaat tggtggtcgt  480
tttgacttca ata                                                  493

<210> SEQ ID NO 84
<211> LENGTH: 443
<212> TYPE: DNA
<213> ORGANISM: Nicotiana tabacum

<400> SEQUENCE: 84
aaaggttgat atcaaaactt acagcgacta tggggagctc tcatcagcac ttgaaaagat    60
gttcagctgc tttagtattg ggcagtgcgc cagcgatgga cttccggggc aagaggaact  120
tagtgaaagt cacttgatgg atcttctcaa tggttctgag tatgttctga cttatgaaga  180
caaagatggt gattggatgc ttgttggcga tgttccttgg agatgttca tagactcatg  240 caagagattg cggatcatga aaagctcaga ggcaattggg ctagctccaa gggctataca  300
caagtgcaag aacaaaaact agtgactgaa aaaccattca atggtttcta tgtcgatgat  360
tatccttttt ctgctctctt ttgtatctgg aattagacta gacgtgtagc attccctgaa  420
aggaaaagca ctggtttaag aag                                        443

<210> SEQ ID NO 85
<211> LENGTH: 454
<212> TYPE: DNA
<213> ORGANISM: Nicotiana tabacum

<400> SEQUENCE: 85

```
gctatagttt ataaaattac caagaacgtc gttacacgaa ttcaacgtct caaccccgat      60
ttgagacttg atcctcacat actaatcttc tgtgctcgtg cacctggaga agcttcctct     120
ccacaccaag ctgatattca accaatcaat tttccatctg atggtagtaa caatcaaggt     180
cgagagtcct ccaaataggc tatcagctca gcggaaggtt ttgctgcgct ccatttgctc     240
cggagttgct tatgtggtca atatgattag gacatgtact gattagtatg tcggggccgt     300
gtcccgacct ttatgacatt tatgtactct tagaggtttg tagacatatg tcgaatacgt     360
gaaagattgt acggccttgt cggcctatgt tttgagttta taaatgatca tgttggccta     420
ttaggcccgt atgtcacatg tatatgatga tgta                                 454

<210> SEQ ID NO 86
<211> LENGTH: 393
<212> TYPE: DNA
<213> ORGANISM: Nicotiana tabacum

<400> SEQUENCE: 86
cagaagctga aggagaagag aatatcggaa gaaggatgat acaccggaaa tggagtttgc      60
taacaggccc cgctgcaatt ctcggcggta tcgtcggtac tatcgtcgtc gccaatttta     120
tcttcgtcca aaatgacccg ttccttaagc ccgatcggaa gcaggagaag gcaccttcaa     180
acaagtgaga aatgcgtgtg attttctctg gtttggggtt ttctgttggt ttgatttgtc     240
actacattac ggcccaataa actcaaattt tgagcattag cttgaatgta ggttttcttt     300
tgttggcttt ctttctgtac tctttctctt cacagaatat gaaagtatgc tccaaacaag     360
agtcctaggt tgggaactgg tcatctcctg ttt                                  393

<210> SEQ ID NO 87
<211> LENGTH: 488
<212> TYPE: DNA
<213> ORGANISM: Nicotiana tabacum

<400> SEQUENCE: 87
caagagaaat ccctaaatgg cgacggcgat gttcagatct agtattcgct ccgccctccg      60
cagcggcgct cctcgtgtaa ctccggcttc aagagaacc ttctcttctc actcatccgt     120
tgaggaagag gcccgtgaag cctctaagtg ggagaaaatt acttatgttg aatagtttc     180 ctgctctatt cttgctgcga tttgtctgtc aaagggtcac cctcactctg atgagcctcc     240
tgcttactca tatctgcaca ttcgcaacaa ggagtttcca tggggtccag atgggctttt     300
tgaggtcaag caccactgaa actgcgtggt ttctctgtga aggcgttaaa ataattcctg     360
tccatccgcg aggatgatca catttgttga attttcatta gatgtctact tttggttctt     420
tgcttataag aaacctttgc cttttctttg acatatttcc atcttttgct gtatacttac     480
aatgtgct                                                              488

<210> SEQ ID NO 88
<211> LENGTH: 501
<212> TYPE: DNA
<213> ORGANISM: Nicotiana tabacum

<400> SEQUENCE: 88
tacggcaaag tgtgggtcaa taatcaggaa gtgatggagc atcagggcgg ctatacgcca      60
tttgaagccg atgtcacgcc gtatgttatt gccgggaaaa gtgtacgtat caccgtttgt     120
gtgaacaacg aactgaactg gcagactatc ccgccgggaa tggtgattac cgacgaaaac     180
```

```
ggcaagaaaa agcagtctta cttccatgat ttctttaact atgccggaat ccatcgcagc    240
gtaatgctct acaccacgcc gaacacctgg gtggacgata tcaccgtggt gacgcatgtc    300
gcgcaagact gtaaccacgc gtctgttgac tggcaggtgg tggccaatgg tgatgtcagc    360
gttgaactgc gtgatgcgga tcaacaggtg gttgcaactg acaaggcac tagcgggact     420 ttgcaagtgg tgaatccgca cctctggcaa ccgggtgaag gttatctcta tgaactgtgc    480
gtcacagcca aaagccagac a                                              501
```

```
<210> SEQ ID NO 89
<211> LENGTH: 25
<212> TYPE: DNA
<213> ORGANISM: Nicotiana tabacum

<400> SEQUENCE: 89
ggattcccgg gattttgaat tcttg                                           25

<210> SEQ ID NO 90
<211> LENGTH: 29
<212> TYPE: DNA
<213> ORGANISM: Nicotiana tabacum

<400> SEQUENCE: 90
atcgaacaaa ttgttaaact cactgcgta                                       29

<210> SEQ ID NO 91
<211> LENGTH: 26
<212> TYPE: DNA
<213> ORGANISM: Nicotiana tabacum

<400> SEQUENCE: 91
ctttccctcg ttttattagc agatca                                          26

<210> SEQ ID NO 92
<211> LENGTH: 30
<212> TYPE: DNA
<213> ORGANISM: Nicotiana tabacum

<400> SEQUENCE: 92
ctatttacaa gaattaacgc ttaatcaatg                                      30

<210> SEQ ID NO 93
<211> LENGTH: 24
<212> TYPE: DNA
<213> ORGANISM: Nicotiana tabacum

<400> SEQUENCE: 93
actaataatt gcaccgagac aaac                                            24

<210> SEQ ID NO 94
<211> LENGTH: 9
<212> TYPE: PRT
<213> ORGANISM: Arabidopsis thaliana

<400> SEQUENCE: 94

Thr Glu Leu Arg Leu Gly Leu Pro Gly
1               5

<210> SEQ ID NO 95
<211> LENGTH: 9
<212> TYPE: PRT
<213> ORGANISM: Arabidopsis thaliana
```

```
<400> SEQUENCE: 95

Thr Asp Leu Arg Leu Gly Leu Ser Phe
1               5

<210> SEQ ID NO 96
<211> LENGTH: 8
<212> TYPE: PRT
<213> ORGANISM: Arabidopsis thaliana

<400> SEQUENCE: 96

Glu Leu Glu Leu Gly Leu Gly Leu
1               5

<210> SEQ ID NO 97
<211> LENGTH: 8
<212> TYPE: PRT
<213> ORGANISM: Arabidopsis thaliana

<400> SEQUENCE: 97

Glu Leu Gly Leu Thr Leu Ser Leu
1               5

<210> SEQ ID NO 98
<211> LENGTH: 8
<212> TYPE: PRT
<213> ORGANISM: Arabidopsis thaliana

<400> SEQUENCE: 98

Glu Leu Asp Leu Gly Leu Ser Leu
1               5

<210> SEQ ID NO 99
<211> LENGTH: 8
<212> TYPE: PRT
<213> ORGANISM: Arabidopsis thaliana

<400> SEQUENCE: 99

Asp Leu Gly Leu Ser Leu Arg Thr
1               5

<210> SEQ ID NO 100
<211> LENGTH: 8
<212> TYPE: PRT
<213> ORGANISM: Arabidopsis thaliana

<400> SEQUENCE: 100

Asn Leu Ser Leu Ser Leu Thr Phe
1               5

<210> SEQ ID NO 101
<211> LENGTH: 7
<212> TYPE: PRT
<213> ORGANISM: Arabidopsis thaliana

<400> SEQUENCE: 101

Lys Lys Leu Glu Leu Arg Leu
1               5

<210> SEQ ID NO 102
<211> LENGTH: 9
<212> TYPE: PRT
<213> ORGANISM: Nicotiana tabacum

<400> SEQUENCE: 102
```

Ile Asp Leu Asp Leu Asn Leu Ala Pro
1               5

<210> SEQ ID NO 103
<211> LENGTH: 9
<212> TYPE: PRT
<213> ORGANISM: Arabidopsis thaliana

<400> SEQUENCE: 103

Leu Asp Leu Asp Leu Asn Leu Pro Pro
1               5

<210> SEQ ID NO 104
<211> LENGTH: 9
<212> TYPE: PRT
<213> ORGANISM: Arabidopsis thaliana

<400> SEQUENCE: 104

Leu Asp Leu Asp Leu Asn Leu Ala Pro
1               5

<210> SEQ ID NO 105
<211> LENGTH: 8
<212> TYPE: PRT
<213> ORGANISM: Oryza sativa

<400> SEQUENCE: 105

Phe Asp Leu Asp Leu Asn Arg Pro
1               5

<210> SEQ ID NO 106
<211> LENGTH: 9
<212> TYPE: PRT
<213> ORGANISM: Arabidopsis thaliana

<400> SEQUENCE: 106

Phe Gln Phe Asp Leu Asn Phe Pro Pro
1               5

<210> SEQ ID NO 107
<211> LENGTH: 7
<212> TYPE: PRT
<213> ORGANISM: Arabidopsis thaliana

<400> SEQUENCE: 107

Leu Asp Leu Asn Ala Ser Pro
1               5

<210> SEQ ID NO 108
<211> LENGTH: 9
<212> TYPE: PRT
<213> ORGANISM: Arabidopsis thaliana

<400> SEQUENCE: 108

Leu Asp Leu Asp Leu Asn Phe Pro Pro
1               5

<210> SEQ ID NO 109
<211> LENGTH: 7
<212> TYPE: PRT
<213> ORGANISM: Arabidopsis thaliana

<400> SEQUENCE: 109

Phe Asp Leu Asn Ile Pro Pro
1               5

```
<210> SEQ ID NO 110
<211> LENGTH: 7
<212> TYPE: PRT
<213> ORGANISM: Arabidopsis thaliana

<400> SEQUENCE: 110

Leu Asp Leu Asn Leu Thr Pro
1               5

<210> SEQ ID NO 111
<211> LENGTH: 6
<212> TYPE: PRT
<213> ORGANISM: Arabidopsis thaliana

<400> SEQUENCE: 111

Ile Asp Leu Asn Leu Pro
1               5

<210> SEQ ID NO 112
<211> LENGTH: 7
<212> TYPE: PRT
<213> ORGANISM: Catharanthus roseus

<400> SEQUENCE: 112

Leu Asp Leu Asn Leu Thr Pro
1               5

<210> SEQ ID NO 113
<211> LENGTH: 7
<212> TYPE: PRT
<213> ORGANISM: Catharanthus roseus

<400> SEQUENCE: 113

Phe Asp Leu Asn Leu Pro Ala
1               5

<210> SEQ ID NO 114
<211> LENGTH: 28
<212> TYPE: DNA
<213> ORGANISM: Nicotiana tabacum

<400> SEQUENCE: 114
cacctacgac atggaagtgg ctttcaga                                         28

<210> SEQ ID NO 115
<211> LENGTH: 25
<212> TYPE: DNA
<213> ORGANISM: Nicotiana tabacum

<400> SEQUENCE: 115
gccttatctt tgctcaagat tttgg                                            25

<210> SEQ ID NO 116
<211> LENGTH: 25
<212> TYPE: DNA
<213> ORGANISM: Nicotiana tabacum

<400> SEQUENCE: 116
cacctgacta tgaagaaagt ctgag                                            25

<210> SEQ ID NO 117
<211> LENGTH: 33
<212> TYPE: DNA
```

<213> ORGANISM: Nicotiana tabacum

<400> SEQUENCE: 117
ggctttaatt gaataacttc ataaaatgaa tcg                             33

<210> SEQ ID NO 118
<211> LENGTH: 25
<212> TYPE: DNA
<213> ORGANISM: Nicotiana tabacum

<400> SEQUENCE: 118
caccattgtc tccacatttg cctta                                      25

<210> SEQ ID NO 119
<211> LENGTH: 28
<212> TYPE: DNA
<213> ORGANISM: Nicotiana tabacum

<400> SEQUENCE: 119
gaaaagaatt caagactcaa agacaccc                                   28

<210> SEQ ID NO 120
<211> LENGTH: 24
<212> TYPE: DNA
<213> ORGANISM: Nicotiana tabacum

<400> SEQUENCE: 120
cacctcaacg gctaccagaa tggc                                       24

<210> SEQ ID NO 121
<211> LENGTH: 29
<212> TYPE: DNA
<213> ORGANISM: Nicotiana tabacum

<400> SEQUENCE: 121
ccaccattct ctgtatgttg aattgctcc                                  29

<210> SEQ ID NO 122
<211> LENGTH: 492
<212> TYPE: DNA
<213> ORGANISM: Nicotiana tabacum

<400> SEQUENCE: 122
cacctacgac atggaagtgg ctttcagaaa atctattaat ggaggcttag tcaaagagga    60
gaagaggaac aaattagctt atcaatccag ttctgatgag gagggttttg ttgaagacag   120
taatgttctt aaggtcggga aggaaagaga agtccatgag gacgataatt cgaagtatcc   180
tcagcaagag gatatcgaca gtgacaagga ggacgatcag ctacaatcag tcaaagctga   240
tatgaaagag gtaatgaaag aaaatcagag gctgaagatg cacttggatc gaattatgaa   300
ggattatcgg aaccttcagc tgcaatttca cgacattgtt caaagaaatg ctgaaaaatc   360
caatagtatt attgatactg atcggcataa tgaatgtaac gaagctgaat tgtctccct    420 tagcttagga agatcttcaa gcgacactaa aaaagaagag tacttatcca aaatcttgag   480
caaagataag gc                                                      492

<210> SEQ ID NO 123
<211> LENGTH: 205
<212> TYPE: DNA
<213> ORGANISM: Nicotiana tabacum

<400> SEQUENCE: 123

```
cacctgacta tgaagaaagt ctgaggtgaa atcaagaatt aagatgagat tcaataggaa    60
gatgtagaac aataaaatag tccatggatg tgtctttggg tctttaatct tttctgattt   120
tattgattta gcgttatttc atgtaaatac gcagtgagtt taacaatttg ttcgattcat   180
tttatgaagt tattcaatta aagcc                                         205

<210> SEQ ID NO 124
<211> LENGTH: 178
<212> TYPE: DNA
<213> ORGANISM: Nicotiana tabacum

<400> SEQUENCE: 124
caccattgtc tccacatttg ccttattctc agcttgtcat tatataatca aaaggacacc    60
ggtatatata catatgcacc tgaccgtaaa gaaagtctga ggtgattccc tgaattggga   120
ttaggactca atagaagatg tgtagaagag gggtgtcttt gagtcttgaa ttcttttc     178

<210> SEQ ID NO 125
<211> LENGTH: 341
<212> TYPE: DNA
<213> ORGANISM: Nicotiana tabacum

<400> SEQUENCE: 125
cacctcaacg gctaccagaa tggcacttcc aaacaccaaa acgggcacca gaatggcact    60
ttcgaacatc ggaacggcca ccagaatggg acatccgaac aacagaacgg acaatcagc   120 catgacaatg gcaacgagct actgggaagc tccgactcta ttaagcctgg ctggttttca   180
gagtttagcg cattatggcc aggtgaagca ttctcactta aggttgagaa gttactattc   240
caggggaagt ctgattacca agatgtcatg ctctttgagt cagcaactta tgggaaggtt   300
ctgactttgg atggagcaat tcaacataca gagaatggtg g                       341

<210> SEQ ID NO 126
<211> LENGTH: 37
<212> TYPE: DNA
<213> ORGANISM: Artificial Sequence
<220> FEATURE:
<223> OTHER INFORMATION: Synthetic primer

<400> SEQUENCE: 126
gcgattaatg gaagtcatat ctaccaacac aaatggc                             37

<210> SEQ ID NO 127
<211> LENGTH: 35
<212> TYPE: DNA
<213> ORGANISM: Artificial Sequence
<220> FEATURE:
<223> OTHER INFORMATION: Synthetic primer

<400> SEQUENCE: 127
cgtggtcgac ttaagactcg atcatacttc tggcg                               35

<210> SEQ ID NO 128
<211> LENGTH: 1145
<212> TYPE: DNA
<213> ORGANISM: Nicotiana tabacum

<400> SEQUENCE: 128
gcgattaatg gaagtcatat ctaccaacac aaatggctct accatcttca agaatggtgc    60
cattcccatg aacggccacc aaaatggcac ttctgaacac ctcaacggct accagaatgg   120
```

```
cacttccaaa caccaaaacg ggcaccagaa tggcactttc gaacatcgga acggccacca    180
gaatgggaca tccgaacaac agaacgggac aatcagccat gacaatggca acgagctact    240
gggaagctcc gactctatta agcctggctg gttttcagag tttagcgcat tatggccagg    300
tgaagcattc tcacttaagg ttgagaagtt actattccag gggaagtctg attaccaaga    360
tgtcatgctc tttgagtcag caacttatgg gaaggttctg actttggatg gagcaattca    420
acatacagag aatggtggat ttccatacac tgaaatgatt gttcatctac cacttggttc    480
catcccaaac ccaaaaaagg ttttgatcat cggcggagga attggttttta cattattcga    540 aatgcttcgt tatccttcaa tcgaaaaaat tgacattgtt gagatcgatg acgtggtagt    600
tgatgtatcc agaaaatttt tcccttatct ggcagctaat tttaacgatc ctcgtgtaac    660
cctagttctc ggagatggag ctgcatttgt aaaggctgca caagcgggat attatgatgc    720
tattatagtg gactcttctg atcccattgg tccagcaaaa gatttgtttg agaggccatt    780
ctttgaggca gtagccaaag cccttaggcc aggaggagtt gtatgcacac aggctgaaag    840
catttggctt catatgcata ttattaagca aatcattgct aactgtcgtc aagtctttaa    900
gggttctgtc aactatgctt ggacaaccgt tccaacatat cccaccggtg tgatcggtta    960
tatgctctgc tctactgaag ggccagaagt tgacttcaag aatccagtaa atccaattga    1020
caaagagaca actcaagtca gtccaaatt aggacctctc aagttctaca actctgatat    1080
tcacaaagca gcattcattt taccatcttt cgccagaagt atgatcgagt cttaagtcga    1140
ccacg                                                                1145

<210> SEQ ID NO 129
<211> LENGTH: 24
<212> TYPE: DNA
<213> ORGANISM: Artificial Sequence
<220> FEATURE:
<223> OTHER INFORMATION: Synthetic primer

<400> SEQUENCE: 129
ggatccgtga tggatgccgc aaat                                           24

<210> SEQ ID NO 130
<211> LENGTH: 27
<212> TYPE: DNA
<213> ORGANISM: Artificial Sequence
<220> FEATURE:
<223> OTHER INFORMATION: Synthetic primer

<400> SEQUENCE: 130
ggtaccttaa gcagagcttg atcgtcc                                        27

<210> SEQ ID NO 131
<211> LENGTH: 24
<212> TYPE: DNA
<213> ORGANISM: Artificial Sequence
<220> FEATURE:
<223> OTHER INFORMATION: Synthetic primer

<400> SEQUENCE: 131
ggatccgtta tggacgccgc aaat                                           24

<210> SEQ ID NO 132
<211> LENGTH: 27
<212> TYPE: DNA
<213> ORGANISM: Artificial Sequence
<220> FEATURE:
<223> OTHER INFORMATION: Synthetic primer
```

```
<400> SEQUENCE: 132
ggtaccttaa gcggagcttg atcgttg                                27
```

TOBACCO ENZYMES FOR REGULATING CONTENT OF PLANT METABOLITES, AND USES THEREOF

This application is a Continuation of PCT International Application No PCT/JP2011/053297 filed in Japan on Feb. 16, 2011, which claims the benefit of Patent Application No. 2010-032537 filed in Japan on Feb. 17, 2010, the entire contents of which are hereby incorporated by reference.

TECHNICAL FIELD

The present invention relates to a regulatory factor of a component in a plant, more specifically, to a base sequence and an amino acid sequence of a gene regulating a component in a plant, a genetically modified plant modified with the gene, and a preparation method of the genetically modified plant.

BACKGROUND ART

Generally, tobacco products are produced from a material obtained by blending various types of leaf tobacco. Blending is a process generally carried out not only for tobacco products but also for various food products such as products of coffee, tea, rice and wheat flour. Because leaf tobacco is an agricultural product, amounts of components in the leaf tobacco vary every year depending on weather conditions. However, blending a various types of leaf tobacco as appropriate makes it possible to reproduce a material having a target quality. This allows providing products having a stable quality. Further, if development of leaf tobacco can provide leaf tobacco having different components in terms of quantity and quality from those of conventional leaf tobacco, a range of taste and flavor created by blending will be able to extend. This makes it possible to further develop various new products. Presently, a diversity of leaf tobacco is created by combinations of varieties, cultivation methods, curing methods, storage/fermentation methods, production regions, stalk positions and the like. For further extending possibilities of such blending techniques, it is desired to develop new leaf tobacco having different components, for example, components relevant to flavor and smoking taste, in terms of quantity and quality from those of conventional leaf tobacco.

Examples of components relevant to flavor and smoking taste in leaf tobacco are sugars, amino acids, organic acids, phenolic compounds, terpenoids, and alkaloids (nicotine).

Among the above components, nicotine is one of main components of leaf tobacco. Leffingwell reports that respective nicotine contents of *Nicotiana tabacum* and *Nicotiana rustica* are in a range of 0.2% to 8% (Non-Patent Literature 1). The nicotine contents in leaf tobacco vary in a wide range due to great influences from not only genetic factors that each variety has but also environmental factors such as meteorological factors and edaphic factors, and cultivation factors such as fertilization methods, topping methods, and harvesting methods.

Among such factors, our understanding on genetic factors has greatly progressed in recent years, as a result of development of molecular biology and genetic recombination techniques. Such progress has lead to identification of many genes that influence nicotine contents of *Nicotiana* plants.

For example, Sato et al. report transgenic plants (*Nicotiana sylvestris*) whose leaf nicotine contents are decreased by suppression of expression of putrescine methyl transferase (PMT) gene or increased by overexpression of the PMT gene (Non-Patent Literature 2). Xie et al. report transgenic plants whose leaf nicotine contents are decreased by suppression of expression of quinolate phosphoribosyl transferase (QPT) gene (Non-Patent Literature 3). Hashimoto et al. report transformed tobacco hairy roots (variety K326) whose nicotine contents are increased by overexpression of one or both of A622 and NBB1 genes and transformed tobacco plants (variety K326) whose leaf nicotine contents are increased by overexpression of one or both of PMT and QPT genes (Patent Literature 1). Further, Hashimoto et al. report transformed tobacco hairy roots (variety SR-1) whose nicotine contents are decreased by suppressing expression of N-methyl putrescine oxidase (MPO) gene and transformed tobacco cells (BY-2) whose nicotine contents are increased by overexpression of the MPO gene (Patent Literature 2). Furthermore, Hashimoto et al. report transformed tobacco cells (BY-2) and transformed tobacco hairy roots (variety Petit Havana SR1) nicotine contents of which transformed tobacco cells and transformed hairy roots are decreased by suppressing expression of A622 gene or NBB1 gene and also reports transformed tobacco plants (variety Petit Havana SR1) whose leaf nicotine contents are decreased by suppressing expression of the NBB1 gene (Patent Literature 3). Chintapakorn and Hamill report transformed hairy roots (variety NC-95) whose nicotine content is decreased by suppressing expression of arginine decarboxylase (ADC) gene (Non-Patent Literature 4). Hakkinen et al. report transformed tobacco cells (BY-2) whose nicotine contents are increased by overexpression of MAP2, MC126 or MT401 gene and transformed tobacco hairy roots (variety BY-2) whose nicotine contents are increased by overexpression of C127 gene (Non-Patent Literature 5). Shoji et al. report transformed tobacco plants whose leaf nicotine contents are decreased by suppressing expression of COI1 gene (Non-Patent Literature 6). Wang et al. report transformed plants whose leaf nicotine contents are decreased by concurrently suppressing expression of JAR4 and JAR6 genes in *Nicotiana attenuata* (Non-Patent Literature 7). Bailey et al. report transformed tobacco plants whose nicotine contents are increased by overexpression of VHb gene (Patent Literature 4). Inze et al. report transformed tobacco cells (BY-2) whose nicotine contents are increased by overexpression of MAP3 gene (Patent Literature 5). Page and Todd report transformed plants (*Nicotiana benthamiana*) whose nicotine contents are decreased by suppressing expression of NbTF1, NbTF4, or NbTF5 gene encoding a transcription factor and transformed plants (*Nicotiana benthamiana*) whose nicotine contents are increased by overexpression of the NbTF1, NbTF4, or NbTF5 (Patent Literature 6).

Regarding biosynthesis and an accumulation mechanism of nicotine in *Nicotiana* plants, a lot of physiological studies have been made for ages. As a result, involvement of plant hormones such as auxin, jasmonic acid, salicylic acid, and ethylene has become evident. For example, Solt (Non-Patent Literature 8), Yasumatsu (Non-Patent Literature 9), Mizusaki et al. (Non-Patent Literature 10), and Takahashi and Yamada (Non-Patent Literature 11) report that auxin negatively regulates the biosynthesis or accumulation of nicotine. Further, Baldwin et al. (Non-Patent Literature 12) report that salicylic acid negatively regulates accumulation of nicotine. Furthermore, Baldwin et al. (Non-Patent Literature 13), Imanishi et al. (Non-Patent Literature 14), and Goossens et al. (Non-Patent Literature 15) report that jasmonic acid positively regulates biosynthesis and accumulation of nicotine. Shoji et al. (Non-Patent Literature 16) and Kahl et al. (Non-Patent Literature 17) report that ethylene negatively regulates biosynthesis or accumulation of nicotine.

Such involvement of various plant hormones indicates that biosynthesis and accumulation of nicotine is regulated by complex networks including a plurality of signaling systems and a plurality of transcriptional regulation systems. Such networks are reported by Kazan and Manners (Non-Patent Literature 18), for example. Among the above-described genes that influence nicotine contents of *Nicotiana* plants, for example, COI1, JAR4, JAR6, MAP3, NbTF1, NbTF4, and NbTF5 genes are considered to be not genes encoding nicotine biosynthetic enzymes but genes involved in signaling or transcriptional regulation.

Plant hormones act on various aspects of various life processes. For example, plant hormones act on growth and regulation of morphology of plants, regulation of a secondary metabolic system, and regulation of response to biological/non-biological stresses. Accordingly, genes affecting leaf nicotine contents via signaling or transcriptional regulation of the plant hormones may vary not only nicotine but also other components in plants. The genes having such functions are important in increasing a diversity of leaf tobacco as described above. Accordingly, studies have been continued for identification of not only known genes but also new genes.

CITATION LIST

Patent Literatures

Patent Literature

[Patent Literature 1] International Publication No. WO2007/072224 A2 (Publication Date: Jun. 28, 2007)
[Patent Literature 2] Specification of US Patent Application Publication No. 2008/0292735 A1 (Publication date: Nov. 27, 2008)
[Patent Literature 3] International Publication No. WO2006/109197 A2 (Publication Date: Sep. 29, 2006)
[Patent Literature 4] International Publication No. WO1998/012913 A1 (Publication Date: Apr. 2, 1998)
[Patent Literature 5] International Publication No. WO2003/097790 A2 (Publication Date: Nov. 27, 2003)
[Patent Literature 6] International Publication No. WO2009/063312 A2 (Publication Date: May 22, 2009)

Non-Patent Literatures

[Non-Patent Literature 1] D. Layton Davis and Mark T. Nielsen., eds Chapter 8, Leaf Chemistry, 8A Basic Chemical Constituents of Tobacco Leaf and Differences among Tobacco Types, Tobacco Production, Chemistry and Technology, Blackwell Science Ltd, 265-284 (1999).
[Non-Patent Literature 2] Sato et al., Metabolic engineering of plant alkaloid biosynthesis., Proc. Natl. Acad. Sci. USA. 98: 367-372 (2001).
[Non-Patent Literature 3] Xie et al., BIOTECHNOLOGY: A TOOL FOR REDUCED-RISK TOBACCO PRODUCTS-THE NICOTINEEXPREENCE FROM TEST TUBE TO CIGARETTE PACK, In Recent Advances in Tobacco Science Vomule 30, Synposium Proceedings 58th Meeting, TOBACCO SCIENCE RESEARCH CONFERENCE (2004).
[Non-Patent Literature 4] Chintapakorn and Hamill, Antisense-mediated regulation in ADC activity causes minor alterations in the alkaloid profile of cultured hairy roots and regenerated transgenic plants of *Nicotiana tabacum*. Phytochemistry. 68: 2465-2479 (2007).
[Non-Patent Literature 5] Hakkinen et al., Functional characterization of genes involved in pyridine alkaloid biosynthesis in tobacco. Phytochemistry. 68: 2773-2785 (2007).
[Non-Patent Literature 6] Shoji et al., Jasmonate-Induced Nicotine Formation in Tobacco is Mediated by Tobacco COI1 and JAZ Genes. Plant and Cell Physiology. 49: 1003-1012 (2008).
[Non-Patent Literature 7] Wang et al., Comparisons of LIPDXYGENASE3- and JASMONATE-RESISTANT4/6—Silenced Plants Reveal That Jasmonic Acid and Jasmonic Acid-Amino Acid Conjugates Play Different Roles in Herbivore Resistance of *Nicotiana* attenuate. Plant Physiology. 146: 904-915 (2008).
[Non-Patent Literature 8] Solt, Nicotine production and growth of excised tobacco root cultures. Plant Physiology. 32: 480-484 (1957).
[Non-Patent Literature 9] Yasumatsu, Studies on the chemical regulation of alkaloid biosynthesis in tobacco plants. Part II. Inhibition of alkaloid biosynth esis by exogenous auxins. Agr. Biol. Chem. 31: 1441-1447 (1967).
[Non-Patent Literature 10] Mizusaki et al., Changes in the activities of ornithine decarboxylase, putorescine N-methyltransferase and N-methylputorescine oxidase in tobacco roots in relation to nicotine biosynthesis. Plant and Cell Physiology. 14: 103-110 (1973).
[Non-Patent Literature 11] Takahashi and Yamada, Regulation of nicotine production by auxins in tobacco cultured cells in vitro. Agr. Biol. Chem. 37: 1755-1757 (1973).
[Non-Patent Literature 12] Baldwin et al., Quantification, correlations and manipulations of wound-induced changes in jasmonic acid and nicotine in *Nicotiana sylvestris*. Planta. 201: 397-404 (1997).
[Non-Patent Literature 13] Baldwin et al., Wound-induced changes in root and shoot jasmonic acid pools correlate with induced nicotine synthesis in *Nicotiana sylvestris* Spegazzini and Comes. J. Chem. Ecol. 20: 1573-1561 (1994).
[Non-Patent Literature 14] Imanishi et al., Differential induction by methyl jasmonate of genes encoding ornithine decarboxylase and other enzymes involved in nicotine biosynthesis in tobacco cell cultures. Plant Mol. Biol. 38: 1101-1111 (1998).
[Non-Patent Literature 15] Goossens et al., A functional genomics approach toward the understanding of secondary metabolism in plant cells. Proc. Natl. Acad. Sci. USA. 100: 8595-8600 (2003).
[Non-Patent Literature 16] Shoji et al., Ethylene supresses jasmonate-induced gene expression in nicotine biosynthesis. Plant and Cell Physiology. 41: 1072-1076 (2000).
[Non-Patent Literature 17] Kahl et al., Herbivore-induced ethylene suppresses a direct defense but not a putative indirect defense against an adapted herbivore. Planta. 210: 336-342 (2000).
[Non-Patent Literature 18] Kazan and Manners, Jasmonate Signaling Toward an Integrated View. Plant Physiology. 146: 1459-1468 (2008).

SUMMARY OF INVENTION

Technical Problem

Accordingly, an object of the present invention is to provide a novel regulatory factor for regulating biosynthesis or accumulation of plant metabolites which new regulatory factor is usable for increasing a diversity of leaf tobacco.

Solution to Problem

As a result of diligent studies in light of the above-described object, the inventors of the present invention found a novel regulatory factor that regulates biosynthesis or accumulation of a plant metabolite. Such a new regulatory factor was found from among a group of genes whose expression varies in a plant body due to a treatment caused by external plant hormones or a treatment varying an amount of an endogenous plant hormone. As a result, the inventors of the present invention accomplished the present invention. Further, the inventors of the present invention successfully produced a plant whose content of a plant metabolite in leaves is regulated by using the novel regulatory factor, and thereby accomplished the present invention.

That is, in order to achieve the object above, a polynucleotide of the present invention is any one of the following (a), (b), and (c), the polynucleotide having a function of regulating a content of a plant metabolite: (a) a polynucleotide consisting of the base sequence of any of SEQ ID NO: 1 to 17; (b) a polynucleotide consisting of a base sequence in which one or several bases are deleted, inserted, substituted or added in the base sequence of any of SEQ ID NO: 1 to 17; and (c) a polynucleotide that hybridizes, under a stringent condition, to a polynucleotide consisting of a complementary sequence of the polynucleotide (a).

In order to achieve the object above, a polynucleotide of the present invention is a polynucleotide encoding a polypeptide set forth in any one of the following (d) and (e), the polypeptide having a function of regulating a content of a plant metabolite: (d) a polypeptide consisting of the amino acid sequence of any of SEQ ID NO: 18 to 32; and (e) a polypeptide consisting of an amino acid sequence in which one or several amino acids are deleted, inserted, substituted or added in the amino acid sequence of any of SEQ ID NO: 18 to 32.

In order to achieve the object above, a polypeptide of the present invention is any one of the following (d) and (e), the polypeptide having a function of regulating a content of a plant metabolite: (d) a polypeptide consisting of the amino acid sequence of any of SEQ ID NO: 18 to 32; and (e) a polypeptide consisting of an amino acid sequence in which one or several amino acids are deleted, inserted, substituted or added in the amino acid sequence of any of SEQ ID NO: 18 to 32.

A vector of the present invention is configured to include the polynucleotide described above.

A method for producing a transformed plant whose content of a plant metabolite is regulated, the method includes the step of transforming a plant cell by using the vector described above.

A transformed plant whose content of a plant metabolite is regulated, the transformed plant is produced by using the vector as described above.

A tobacco product of the present invention is being produced by using a plant body of the transformed plant described above, the transformed plant being *Nicotiana tabacum* or *Nicotiana rustica* whose content of the plant metabolite in a leaf is regulated.

Advantageous Effects of Invention

According to the present invention, an amount of a plant metabolite can be regulated in a plant. This makes it possible to obtain a plant whose amount of a plant metabolite is regulated.

DESCRIPTION OF EMBODIMENTS

Figure 1:
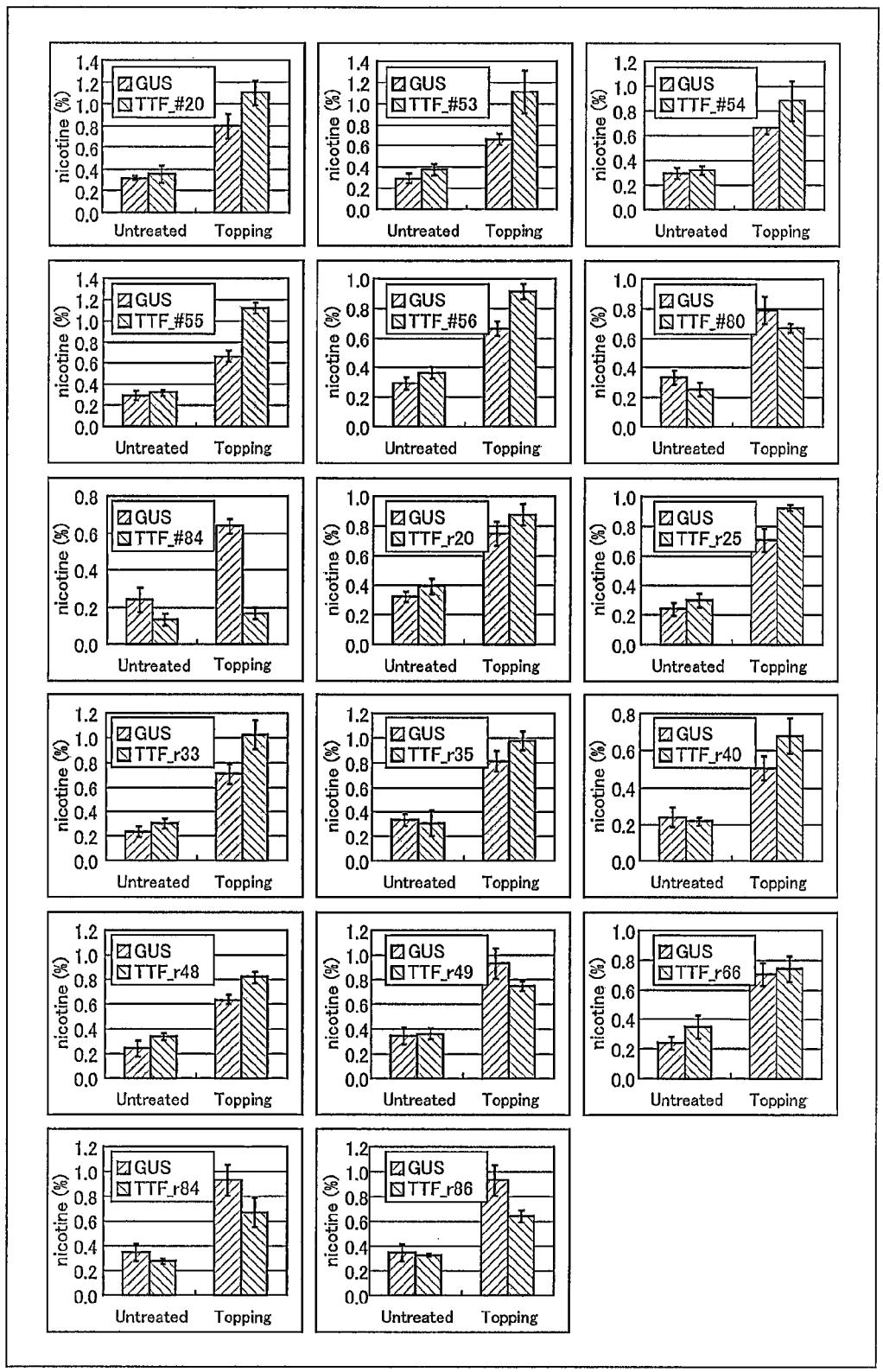
FIG. 1 is a diagram showing changes in nicotine contents in cases where levels of endogenous gene expression are varied by use of genes of the present invention.

Polynucleotide Having Function of Regulating Content of Plant Metabolite

In one aspect, the present invention provides an isolated polynucleotide having a function of regulating a content of a plant metabolite.

Specific examples of the polynucleotide of the present invention are: (a) a polynucleotide encoding the amino acid sequence of any of SEQ ID NO: 18 to 32 or a mutant of the amino acid sequence, or (b) a polynucleotide having the base sequence of any of SEQ ID NO: 1 to 17 or a mutant of the polynucleotide having the base sequence. Here, note that: the polynucleotide of SEQ ID NO: 1 is called TTF_#20 gene; the polynucleotide of SEQ ID NO: 2 is called TTF_#53 gene; the polynucleotide of SEQ ID NO: 3 is called TTF_#54 gene; the polynucleotide of SEQ ID NO: 4 is called TTF_#55 gene; the polynucleotide of SEQ ID NO: 5 is called TTF_#56 gene; the polynucleotide of SEQ ID NO: 6 is called TTF_#80 gene; the polynucleotide of SEQ ID NO: 7 is called TTF_#84 gene; the polynucleotide of SEQ ID NO: 8 is called TTF_r20 gene; the polynucleotide of SEQ ID NO: 9 is called TTF_r25 gene; the polynucleotide of SEQ ID NO: 10 is called TTF_r33 gene; the polynucleotide of SEQ ID NO: 11 is called TTF_r35 gene; the polynucleotide of SEQ ID NO: 12 is called TTF_r40 gene; the polynucleotide of SEQ ID NO: 13 is called TTF_r48 gene; the polynucleotide of SEQ ID NO: 14 is called TTF_r49 gene; the polynucleotide of SEQ ID NO: 15 is called TTF_r66 gene; the polynucleotide of SEQ ID NO: 16 is called TTF_r84 gene; and the polynucleotide of SEQ ID NO: 17 is called TTF_r86 gene.

The term "polynucleotide having a function of regulating a content of a plant metabolite" as used in the present specification indicates (a) an endogenous polynucleotide that is naturally present in a plant cell and that is involved in regulation of a content of a metabolite, or (b) the endogenous polynucleotide isolated. Here, regarding the "function", a polypeptide that is a translation product of the polynucleotide may have the "function". Alternatively, like a functional RNA encoding no polypeptide, the polynucleotide itself may have the "function". Known examples of such a functional RNA are Xist RNA involved in dosage compensation (Non-Patent Literature: Plath K et al., 2002. Annu Rev Genet. 36, 233-78), roX RNA (Non-Patent Literature: Meller and Rattner 2002. Embo J, 21, 1084-91), and SRA that is an activator of a steroid hormone receptor (Non-Patent Literature: Lanz R B et al. 1999. Cell, 97:17-27).

The term "polynucleotide" as used in the present specification is interchangeable with a term "gene", "nucleic acid", or "nucleic acid molecule". This term "polynucleotide" is used to mean a polymer of nucleotides. The term "base sequence" is as used in the present specification is interchangeable with a term "nucleic acid sequence" or "nucleotide sequence". This "base sequence" is shown as a sequence of deoxyribonucleotide (abbreviated by using letters A, G, C, and T).

The polynucleotide of the present invention may be present in a form of RNA (e.g., mRNA) or DNA (e.g., cDNA or genomic DNA). DNA may be present in a double stranded form or a single stranded form. A single-stranded DNA or RNA may correspond to a coding strand (also known as a sense strand) or a non-coding strand (also known as an antisense strand).

In the present specification, in a case where the term "mutant" is used in regard to a polynucleotide, the term "mutant" may be (a) a polynucleotide having a base sequence in which one or several bases are deleted, inserted, substituted or added in the base sequence of any of SEQ ID NO: 1 to 17 or (b) a polynucleotide that hybridizes, under stringent conditions, to a complementary sequence of the base sequence of any of SEQ ID NO: 1 to 17. The "several bases" here means, for example, 2 to 30 bases, more preferably 2 to 10 bases, and most preferably 2 to 6 bases.

The phrase "hybridize, under stringent conditions" means that hybridization occurs only in a case where sequences are at least 90% identical, more preferably 95% identical and most preferably 97% identical. A specific example of the "stringent conditions" is conditions where after overnight incubation at 42° C. in hybridization solution (containing 50% formamide, 5×SSC (150 mM NaCl and 15 mM trisodium citrate), 50 mM sodium phosphate (pH 7.6), 5×Denhardt's solution, 10% dextran sulfate, and 20 μg/ml denatured sheared salmon sperm DNA), a filter is washed in 0.1×SSC at approximately 65° C. Regarding the hybridization, a method is not specifically limited, but may be a conventionally known method such as a method as described in J. Sambrook et al. Molecular Cloning, A Laboratory Manual, 2d Ed., Cold Spring Harbor Laboratory (1989). In general, the higher a temperature is and the lower a salt concentration is, the higher the stringency becomes (that is, the more difficult the hybridization becomes).

Further, the polynucleotide of the present invention may be a polynucleotide encoding a polypeptide of the present invention. In other words, the polynucleotide of the present invention may be (a) a polynucleotide having a base sequence encoding the amino acid sequence of any of SEQ ID NO: 18 to 32 or (b) a polynucleotide having a base sequence encoding an amino acid sequence in which one or several amino acids are deleted, inserted, substituted or added in the amino acid sequence of any of SEQ ID NO: 18 to 32. The term "several amino acids" here means, for example, 2 to 30 amino acids, more preferably 2 to 10 amino acids, and most preferably 2 to 5 amino acids. As described later, the polypeptide of the present invention has a function of regulating a content of a metabolite in plants.

The term "polypeptide" as used in the present specification is interchangeable with a term "peptide" or "protein". The polypeptide of the present invention may be isolated from a natural source or may be chemically synthesized.

The term "plant metabolite" as used in the present specification is interchangeable with a term "metabolite" or "component". The "plant metabolite" can be classified into a primary metabolite or a secondary metabolite. The primary metabolites are substances essential for maintaining a living body. Examples of such substances are sugars, organic acids, amino acids, and fats. The secondary metabolites are metabolites other than the primary metabolites. The secondary metabolite of plants is derived from a primary metabolic system and considered to be involved in, for example, protection against foreign enemies, resistance to stress, and attraction of insects. Specific examples of the secondary metabolism of plants are terpenoids, alkaloids, phenolic compounds, and derivatives of these substances.

The terpenoids basically mean compounds produced as a result of biosynthesis of a plurality of bound isoprene units. The alkaloids mean nitrogen-containing basic organic compounds derived from plants. The phenolic compounds mean phenol-ring-containing organic compounds such as phenylpropanoid and flavonoid.

Examples of the alkaloids are tropane alkaloids, pyrrolidine alkaloids, pyrrolizidine alkaloids, piperidine alkaloids, phenylethylamines, isoquinoline alkaloids, quinoline alkaloids, pyridine alkaloids, indole alkaloids, imidazole alkaloids, purine alkaloids, and benzylisoquinoline alkaloids. The tropane alkaloids are alkaloids each containing in a structure thereof a tropane skeleton. An example of such tropane alkaloids is atropine. The pyridine alkaloids are alkaloids each containing in a structure thereof a pyridine ring. An example of the pyridine alkaloids is nicotine. Note that nicotine as well as nornicotine is a main alkaloid in *Nicotiana* plants. Examples of nicotine-related alkaloids contained in *Nicotiana* plants are nornicotine, anatabine, anabasine, myosmine, N-methylmiosmine, cotinine, nicotyrine, nornicotyrine, nicotine N-oxide, and 2,3'-bipyridyl-metanicotine.

The term "content of plant metabolite" as used in the present specification means an amount of a specific plant metabolite in a plant body. Similarly, the term "alkaloid content" means an amount of specific alkaloid in a plant body. Note that an analysis of the content of the plant metabolite may be carried out by conventionally known methods such as gas chromatography. The content of the plant metabolite can be expressed by weight with respect to dry weight of the plant or weight with respect to fresh weight of the plant.

The phrase "having a function of regulating a content of a plant metabolite" as used in the present specification broadly means involvement in a content of a plant metabolite. That is, the phrase means not only (a) having a function of directly regulating biosynthesis of a plant metabolite but also (b) having a function of indirectly varying a content of a plant metabolite, that is, having a function of changing a content of the plant metabolite consequently even though the change occurs outside a biosynthesis pathway of the plant metabolite. Here, "regulating" means decreasing or increasing a content of a specific plant metabolite.

The term "isolated" as used in regard to the polynucleotide in the present specification indicates to obtain, by "a method for obtaining a polynucleotide" described later, only a specific polynucleotide from a condition where the polynucleotide is naturally present in plant cells. In addition, the term "isolated" also indicates that the polynucleotide may be obtained by chemically synthesizing a full length polynucleotide or the polynucleotide may be synthesized by joining a plurality of polynucleotides that are chemically synthesized.

The method for obtaining the polynucleotide of the present invention is not specifically limited, but may be a general method. For example, the polynucleotide of the present invention may be obtained by cutting out, with use of an appropriate restriction enzyme, and purifying a polynucleotide from a genomic DNA or cDNA library of an organism having a gene of the present invention. The genomic DNA of the gene of the present invention can be obtained, for example, by (i) extracting a genomic DNA from a plant cell or tissue, (ii) preparing a genomic library, and (iii) carrying out colony hybridization or plaque hybridization by using a probe or primer designed based on the base sequence of SEQ ID NO: 1, 2, 3, 4, 5, 6, 7, 8, 9, 10, 11, 12, 13, 14, 15, 16, or 17 from the library prepared above. Alternatively, the polynucleotide of the present invention can be obtained by PCR employing cDNA or genomic DNA of the gene of the present invention as a template.

The gene of the present invention is found as a gene influencing a nicotine content in leaves of *Nicotiana* plants, through analysis by use of a VIGS (Virus-induced gene silencing) system. The gene is found from among selected 149 types of tobacco genes that have responsiveness to plant hormones or some relevance to a transcription factor.

The VIGS system is a method for clarifying a function of a gene by using a mechanism of PTGS (post-transcriptional gene silencing). In the present invention, a TRV (Tobacco Rattle Virus) vector (Ratcliff F. et al., 2001, Plant Journal, 25, 237-245, and U.S. Pat. No. 7,229,829) is used as the VIGS system. Moreover, as a polynucleotide to be inserted into the vector, a partial length cDNA of tobacco (*Nicotiana tabacum* cv. Burley 21, or Tsukuba No. 1) is used. As a plant to which the vector is introduced, *Nicotiana benthamiana* is used.

A new function of the gene of the present invention thus obtained may be further found by use of an accurate mass spectrometer such as a liquid chromatography—time-of-flight mass spectrometry (LC-TOF/MS).

More specifically, influence of the gene of the present invention on a plant metabolite can be clarified in a wide range by analyzing the plant metabolite of (i) plants that are transformed so that the gene of the present invention is overexpressed or progenies of such plants or (ii) plants that are transformed so that expression of the gene of the present invention is suppressed or progenies of such plants. Such analysis is carried out by using an accurate mass spectrometer such as an LC-TOF/MS.

The LC-TOF/MS is an apparatus in which a time-of-flight mass spectrometry (TOF/MS) as a detector is combined with a liquid chromatography (LC) that is a separation/analysis method of refractory or thermolabile compounds. Components separated by the LC are ionized by an ionization section (e.g. ESI; ElectroSpray Ionization). In the TOF/MS, thus obtained ions are flied by electromagnetic force and detected according to difference in flight time caused by mass difference. According to the LC-TOF/MS, various metabolites can be analyzed all at once by using extract from plant leaves. The analysis of the plant metabolites by use of the LC-TOF/MS can be performed specifically as follows.

First, a sample taken from a plant that is transformed or a progeny of the transformed plant, or a wild-type plant is dried and then ground. To the sample ground, 50% acetonitrile is added and extraction is performed. Then, extract is subjected to centrifugation. Further, supernatant obtained as a result of the centrifugation is ultrafiltered and then provided for the LC-TOF/MS analysis. In the analysis using the LC-TOF/MS, 100 or more metabolites can be analyzed all at once in a case where, for example, a tobacco leaf is used as a sample.

Alternatively, the influence of the gene of the present invention on the plant metabolites can also be clarified in a wide range by using a gene expression analysis method such as microarray analysis. For example, by clarifying a gene whose expression level in an above mentioned transformed plant or its progeny is different from that in a wild type plant, it is possible to clarify other genes' expression and a metabolic pathway on both of which the gene of present invention gives effects.

The term "transcription factor" as used in the present specification indicates a protein that has a function of increasing or decreasing transcription of a specific gene. Such a protein works by (a) binding to DNA, in particular, a promoter region of the DNA by interacting with a general transcription factor or (b) binding to another transcription factor that binds to DNA. As a result of studies on *Arabidopsis thaliana*, it is clarified that, as compared to animals and yeasts, higher plants have a remarkably wide variety of transcription factor genes. This suggests that regulation at a transcription level has an important part in biological activities of plants. Though a large part of functions of transcription factors of these plants have not been clarified yet, some functions have been known so far. Examples of such functions are functions relevant to the occurrence and regulation of differentiation of individuals, functions relevant to response to environmental stresses such as heat and drought, and functions relevant to response to disease and insect damages and injuries.

The genes whose functions are clarified as described above are the polynucleotides of the present invention respectively having the base sequences of SEQ ID NO: 1 to 17. For example, in *Nicotiana* plants, by silencing TTF_#20 gene, TTF_#53 gene, TTF_#54 gene, TTF_#55 gene, TTF_#56 gene, TTF_#80 gene, TTF_#84 gene, TTF_r20 gene, TTF_r25 gene, TTF_r33 gene, TTF_r35 gene, TTF_r40 gene, TTF_r48 gene, TTF_r49 gene, TTF_r66 gene, TTF_r84 gene, or TTF_r86 gene, a nicotine content can be decreased or increased as compared to a nicotine content in a plant where the above gene is not silenced.

From the function as described above, it can be said that the genes shown by the base sequences of SEQ ID NO: 1, 2, 3, 4, 5, 6, 7, 8, 9, 10, 11, 12, 13, 14, 15, 16 and 17 are regulatory factors each regulating a "leaf nicotine content" in *Nicotiana* plants.

Some of the genes of the present invention have a domain specific to a transcription factor and therefore considered to be a transcription factor. As the domain specific to the transcription factor that some of the genes of the present invention have, TTF_#20 gene and TTF_#55 gene have WRKY domain. Moreover, TTF_r20 gene, TTF_r25 gene, and TTF_r33 gene have AP2 domain, and TTF_r40 gene and TTF_r48 gene have tify domain. Further, TTF_r49 gene has AUX/IAA domain, and TTF_#53 gene has bHLH domain. In addition, TTF_#54 gene has SANT domain. Note that no domain specific to a transcription factor is found in other genes of the present invention. The genes of the present invention may be involved in any one step of generation, translocation, accumulation and the like of nicotine in *Nicotiana* plants. As a result, it is considered that each of the genes of the present invention affect the "leaf nicotine content".

The functions of the above 17 types of genes of the present invention have not conventionally been clarified. The inventors of the present invention first clarified that each of these 17 types of genes of the present invention has a function of regulating a content of a metabolite.

As possible effects of the above 17 types of genes of the present invention, resistance to environmental stresses such as heat and drought and resistance to disease and insect damages can be provided by (i) increasing/decreasing a content of a plant metabolite or (ii) regulating various signal transduction and transcription.

The vector of the present invention may be prepared by a known genetic recombination technique. In this preparation, the polynucleotide of the present invention or a part thereof is inserted into a predetermined vector. This predetermined vector is not specifically limited, but it is possible to use a cloning vector as well as a gene expression vector described later.

[2. Polypeptide Having Function of Regulating Content of Plant Metabolite]

In one aspect, the present invention provides a polypeptide having a function of regulating a content of a plant metabolite.

The polypeptide of the present invention is preferably a polypeptide having the amino acid sequence of any of SEQ ID NO: 18 to 32 or a mutant of the polypeptide.

The term "mutant" as used in regard to a protein or a polypeptide in the present specification indicates a polypeptide retaining a specific activity that a target polypeptide has. The "mutant of the polypeptide having the amino acid sequence of any of SEQ ID NO: 18 to 32" indicates a polypeptide having a function of regulating a content of a plant metabolite.

It has been known in the field to which the present invention pertains that some amino acids in an amino acid sequence constituting a polypeptide can be easily modified without significantly affecting a structure or function of the polypeptide. Further, it is also conventionally known that, other than the mutant obtained by artificial modification, there is a mutant that is present as a natural protein which mutant has a structure or function not significantly changed from that of the natural protein. Further, the present invention encompasses a polypeptide of an allele of the gene encoding the polypeptide described above.

It is possible for a person skilled in the art to easily cause mutation of one or several amino acids in an amino acid sequence of a polypeptide, by using a conventionally known technique. For example, according to a method of conventional induced point mutation, it is possible to cause mutation of any base of a polynucleotide encoding a polypeptide. Further, it is also possible to prepare a deletion mutant or an additional mutant by designing a primer for any part of the polynucleotide encoding the polypeptide.

The polypeptide of the present invention includes a natural purified product, a product synthesized by chemical synthesis, and a product produced by a recombination technique from a prokaryotic host or a eukaryotic host (including, for example, a bacterial cell, a yeast cell, a higher plant cell, an insect cell, and a mammal cell). Depending on the host used in recombination production procedures, the polypeptide of the present invention can be glycosylated or non-glycosylated. Further, the polypeptide of the present invention may include a modified initiating methionine residue as a result of a host-mediated process.

The polypeptide of the present invention may be a polypeptide that forms a peptide bond with an amino acid, but not limited to this polypeptide. The polypeptide of the present invention may be a complex polypeptide having a structure other than that of polypeptide. The term "structure other than that of polypeptide" as used in the present specification may be a sugar chain, an isoprenoid group, or the like, but not limited to these.

Further, the polypeptide of the present invention may include an additional polypeptide. Examples of such an additional polypeptide are an epitope indicator polypeptide such as His tag, Myc tag, and FLAG (Registered Trademark) peptide.

[3. Vectors]

The vector of the present invention can be prepared by a known genetic recombination technique. In this preparation, the polynucleotide of the present invention or a part thereof is inserted into a predetermined vector. This predetermined vector is not specifically limited, but encompasses a cloning vector as well as a plant transformation vector for transformation of plants described later. Further, the plant transformation vector encompasses a gene expression vector and a gene suppression vector. The gene expression vector and the gene suppression vector may be used according to need for regulating a content of a plant metabolite. The plant transformation vector to be used may be vectors intended for (i) homologous recombination, (ii) expression of dominant negative gene products (Patent Literature: Japanese Patent Application Publication, Tokukai, No. 2005-027654), and (iii) introduction of decoy molecules (Patent Literatures: Publications of Japanese Translations of PCT International Applications, Tokuhyo, No. 2001-510987 and Tokuhyo, No. 2004-507250; and Non-Patent Literature: Sullenger et al., 1991, J. Vitrol., 65, 6811-6816.).

(Gene Expression Vector)

Among recombinant vectors used for genetic transformation of a plant, the gene expression vector is a vector for overexpressing the gene of the present invention within a plant cell. The gene expression vector is constructed by inserting, into an appropriate vector, a polynucleotide encoding the amino acid sequence of any of SEQ ID NO: 18 to 32 or a mutant of the amino acid sequence or a polynucleotide having the base sequence of any of SEQ ID NO: 1 to 17 or a mutant of the polynucleotide having the base sequence. Here, the phrase "overexpressing the gene of the present invention" is used to mean both increase in an amount of mRNA that is a transcription product of the gene of the presnet invention and increase in an amount of protein that is a translation product of the gene of the present invention. Further, it is desirable that one polynucleotide selected from the polynucleotides described above is inserted into the vector. However, a plurality of polynucleotides may also be selected here.

The appropriate vector above is not specifically limited as long as the vector is capable of causing expression of the polynucleotide inserted into the vector within a plant cell. Suitable examples of such a vector are pBI, pPZP, and pSMA vectors each of which allows introduction of a target gene into a plat cell via *Agrobacterium*. Particularly, plasmids of binary vectors (e.g., pBIG, pBIN19, pBI101, pBI121, pBI221, and pPZP202) are preferable. In a case where the gene is directly introduced into a plant cell, it is possible to use, for example, pUC vectors (e.g., pUC18, and pUC19). It is also possible to use plant virus vectors such as Cauliflower mosaic virus (CaMV), Bean golden mosaic virus (BGMV), and Tobacco mosaic viruses (TMV). Here, the phrase "inserting a polynucleotide into a vector" means inserting the polynucleotide into a vector in a manner such that a promotor is connected to a 5' upstream region of the polynucleotide and a terminator is connected to a 3' downstream region of the polynucleotide. Further, in a case where the polynucleotide is derived from a genomic DNA and the polynucleotide includes a promoter or a terminator, it is possible to insert the polynucleotide into a vector that does not have a promoter or a terminator.

The term "introducing" as used in the present invention in relation to a gene or a vector is interchangeable with the term "transforming" or "transfecting". Similarly, the term "introduction" is used so as to be interchangeable with "transformation" or "transfection". Further, the term "introduction" as used in the present specification in relation to plants includes a case of a transient plant transformation in which DNA introduced into a plant is not integrated into a host genomic DNA as well as a case where the DNA is integrated into a host genomic DNA.

In a case where the gene has an ORF, the gene expression vector only needs to include at least an ORF region of the gene. That is, for example, the gene expression vector only needs to include a polynucleotide encoding the amino acid sequence of SEQ ID NO: 18 to or a mutant of the amino acid sequence. Alternatively, the gene expression vector may include an UTR (untranslated region) of each gene. As a further alternative, in a case where the gene has no ORF, the gene expression vector may be a part of the gene as long as the part of the gene has a function of regulating a content of a plant metabolite. For example, the gene expression vector may include a polynucleotide having the base sequence of any of SEQ ID NO: 1 to 17 or a mutant of the polynucleotide or a part of such a polynucleotide.

Further, in the recombinant vector, it is possible to provide a promoter sequence, an enhancer sequence, a terminator sequence, a poly A additional signal, a 5'-UTR sequence, a selection marker gene, a reporter gene, and a replication origin for amplification in *Agrobacterium*.

The promoter is not specifically limited as long as the promoter is capable of functioning in a plant cell. In particular, suitable examples of the promoter are a promoter constitutively expressing a polynucleotide in a plant cell and a promoter whose activity is induced by an external stimulus. Examples of the promoter constitutively expressing a polynucleotide are a Cauliflower mosaic virus (CaMV) 35S promoter, a promoter of *Agrobacterium* nopaline synthase gene, a maize ubiquitin gene promoter, and a rice actin gene promoter. An example of a promoter whose activation is inducible is a heat shock gene promoter. Alternatively, it is also possible to use a promoter activating gene expression specifically in a tissue. Examples of such a promoter that can be used are a promoter of root-specific extensin-like protein gene in tomato (Patent Literature: Publication of Japanese Translation of PCT International Application, Tokuhyo, No. 2002-530075), a TobRB7 promoter of Tobacco (Patent Literature: U.S. Pat. No. 5,459,252) and the like, and a root cortex specific TobRD2 gene promoter (Patent Literature: Publication of Japanese Translation of PCT International Application, Tokuhyohei, No. 11-510056), a promoter of *Arabidopsis thaliana* phosphate transporter gene PHT1 (Patent Literature: Patent Application Publication, Tokukai, No. 2005-046036) and the like.

An example of the enhancer sequence is an enhancer region having an upstream sequence of the CaMV 35S promoter which enhancer region is used for enhancing an expression efficiency of a target gene.

The terminator sequence only needs to be a sequence capable of terminating mRNA synthesis of a gene transcribed by a promoter sequence. Examples of such a terminator sequence are a terminator of nopaline synthase (NOS) gene and a terminator of CaMV 35S RNA gene.

Examples of the selection marker gene are ampicillin resistance gene (Amp, bla), neomycin resistance gene (NPTII), kanamycin resistance gene (NPTIII), hygromycin resistance gene (htp), glufosinate resistance gene (Bar), and chloramphenicol acetyltransferase (CAT). By using these selection marker genes, for example, it becomes possible to easily select a recombinant into which a target gene is introduced on a culture medium containing a selection agent such as ampicillin, neomycin, kanamycin, hygromycin, glufosinate, and chloramphenicol.

The reporter gene may be any reporter gene that makes it possible to check whether or not a plant cell is transformed by expression of genes. Examples of such a reporter gene are β-glucuronidase (GUS), luciferase (LUC), fluorescent proteins such as green fluorescent protein (GFP) and cyan fluorescent protein (CFP), and β-galactosidase (LacZ).

Note that it is also possible to provide a target gene and an expression cassette including the reporter gene on separate recombinant vectors. In this case, both the vectors should be cotransfected into a host.

(Gene Suppression Vector)

Among the recombinant vectors used in transformation of a plant, the gene suppression vector is a vector for suppressing endogenous gene expression within a plant cell. This gene suppression vectors allows producing a transformed plant whose content of a plant metabolite is regulated. The gene suppression vector is constructed by inserting, into an appropriate vector, (a) a part of a polynucleotide encoding the amino acid sequence of any of SEQ ID NO: 18 to 32 or a mutant of the amino acid sequence, or (b) a part of a polynucleotide encoding the base sequence of any of SEQ ID NO: 1 to 17 or a mutant of the polynucleotide. The term "part" as used in the present specification is explained later in detail in a section of various gene suppression vectors, but the "part" is a polynucleotide having a base sequence including 21 or more consecutive bases in the gene of the present invention. This "part" may include a full length gene of the present invention. Further, the "part" may be selected from any part of the gene of the present invention. Therefore, the part may be selected from a UTR. Further, the "base sequence having 21 or more consecutive bases" may be selected from a plurality of parts of the gene of the present invention. For example, it is possible to connect and use these parts of the gene of the present invention. For example, siRNAs used for gene silencing may be used as a cocktail of a plurality of siRNAs mixed, for ensuring an effect of silencing. Further, the "part" may be selected from a polynucleotide derived from a genomic DNA fragment containing the gene of the present invention. For example, the "part" may be selected from an intron, a promoter and the like. Further, though it is desirable that, as in the case of the gene expression vector, one of the polynucleotides described above is selected as the polynucleotide, several polynucleotides may also be selected.

The phrase "Suppression of gene expression" as used in the present specification is intended to mean both decrease in an amount of mRNA that is a transcription product of an endogenous gene and decrease in an amount of protein that is a translation product of the endogenous gene. The gene suppression vector has basically the same components as those of the gene expression vector except the polynucleotide inserted. Therefore, an explanation of the components of the gene suppression vector is omitted.

As a method for causing suppression of gene expression, a conventionally known method can be used. Examples of the method are methods employing antisense, co-suppression, RNA interference (RNAi), microRNA, VIGS, ribozyme, homologous recombination, expression of dominant negative gene products, and standard mutagenesis technology.

In other words, the gene suppression vector indicates an RNAi vector, an antisense vector, a VIGS vector, and the like.

For example, the RNAi vector is a vector expressing a double-stranded RNA (dsRNA) that causes RNAi. Thus expressed dsRNA is digested by a double-stranded-RNA-specific RNase (Dicer) and becomes an RNA having 21 to 25 bases. This RNA is called siRNA. The siRNA forms a complex called RNA-induced silencing complex (RISC). The RISC ultimately recognizes a target mRNA by base sequence homology and degrades the target mRNA. The RNAi vector is preferably a vector that expresses, as a hairpin dsRNA, dsRNA that causes RNAi. The RNAi vector that expresses dsRNA may be a hairpin RNAi vector. This hairpin RNAi vector is constructed, by positioning, at each end of a spacer sequence having at least several bases such as an intron, DNA corresponding to a part in which the dsRNA is formed, and thereby forming IR (inverted repeat). The spacer is not specifically limited, but, an example of the spacer that can be suitably used is a pdk intron (Non-Patent Literature: Wesley S V et al., 2001., Plant J., 27, 581-90.). Further, the RNAi vector may be a tandem-type RNAi. In the tandem RNAi, the sense RNA and the antisense RNA are transcribed by separate promoters and hybridized within a cell and as a result, dsRNA is produced. Alternatively, it is possible to cause RNAi by constructing a plurality of expression vectors from which a sense RNA and an antisense RNA are transcribed, respectively.

Examples of the polynucleotide to be inserted into the RNAi vector is (i) a polynucleotide having the base sequence of 21 or more consecutive bases, more preferably 50 or more consecutive bases, and most preferably 100 or more consecutive bases of (a) a part of a polynucleotide encoding the amino acid sequence of any of SEQ ID NO: 18 to 32 or a mutant of the amino acid sequence, or (b) a part of a polynucleotide encoding the base sequence of any of SEQ ID NO: 1 to 17 or a mutant of the polynucleotide and (ii) a polynucleotide having a complementary sequence of the above base sequence.

Further, for example, the VIGS vector is a vector used for simply checking a function of a gene. Into this vector, a polynucleotide for causing VIGS of a target gene is integrated. The VIGS is a mechanism included in a mechanism of PTGS and considered as a defense mechanism of a plant against viruses. Into the VIGS vector, a part of a base sequence of the target gene is contained. In a plant into which the VIGS vector is introduced, VIGS is induced against amplification of recombinant virus RNA to be produced and an endogenous target gene is silenced.

A usable example of the VIGS vector is a TRV vector. Regarding a VIGS system using the TRV vector, it is possible to refer to Non-Patent Literature: Ratcliff F. et al., 2001, Plant Journal, 25, 237-245 and U.S. Pat. No. 7,229,829.

A possible examples of the polynucleotide inserted into the VIGS vector is a polynucleotide having a base sequence of 100 or more consecutive bases, more preferably 150 or more consecutive bases, and most preferably 200 or more consecutive bases of (a) a part of a polynucleotide encoding the amino acid sequence of any of SEQ ID NO: 18 to 32 or a mutant of the amino acid sequence, or (b) a part of a polynucleotide encoding the base sequence of any of SEQ ID NO: 1 to 17 or a mutant of the base sequence. The polynucleotide may be inserted into the vector either in a sense direction or in an antisense direction.

Further, for example, the antisense vector is a vector into which a polynucleotide for expressing an antisense RNA bound to mRNA of a target gene is integrated. The "antisense" RNA is a polynucleotide having a base sequence that is complementary to endogenous mRNA having a "sense" sequence. The antisense vector used here is, for example, a polynucleotide having, at a downstream of a promoter, a base sequence of 50 or more consecutive bases, more preferably 100 or more consecutive bases, and most preferably 500 or more consecutive bases of (a) a part of a polynucleotide encoding the amino acid sequence of any of SEQ ID NO: 18 to 32 or a mutant of the amino acid sequence or (b) a part of a polynucleotide encoding the base sequence of any of SEQ ID NO: 1 to 17 or a mutant of the base sequence of any of SEQ ID NO: 1 to 17.

Further, regarding the ribozyme vector, it is possible to use a vector in which a ribozyme is connected to a downstream of a promoter such as CaMV 35S promoter in a recombinant vector in a manner such that the ribozyme can be transcribed within a plant cell. The ribozyme here is designed so as to be able to digest a target mRNA.

Further, for example, the co-suppression vector is a vector into which DNA having a sequence identical or similar to a base sequence of a target gene is integrated. The term "co-suppression" is a phenomenon in which expression of both an exogenous gene introduced and a target endogenous gene is suppressed as a result of introduction of a gene having a sequence identical or similar to that of the target endogenous gene into a plant. The gene used in the co-suppression does not need to be completely identical to the target gene. However, it is preferable that the sequence of the gene used in the co-suppression is at least 70% identical, preferably 80% or more identical, and more preferably 90% or more (e.g., 95% or more) identical to that of the target gene. A conventional method can be used to determine the identity of sequence.

Note that results of gene suppression methods may be different due to difference in mechanisms of the methods (e.g., whether the mechanism is transient or constitutive) or difference in experimental systems. Therefore, it is preferable to select a gene suppression method in accordance with a purpose. For example, as compared to VIGS that is a transient assay system under virus infection, RNAi gene silencing in a stably transformed plant provides an embodiment that is closer to cultivation by farmers.

[4. Method for Producing Transformed Plant Whose Content of Plant Metabolite is Regulated]

The transformed plant of the present invention whose content of a plant metabolite is regulated can be produced by transforming a target plant by use of the vector of the present invention described above.

The term "transformed plant of the present invention whose content of a plant metabolite is regulated" means a transformed plant whose content of a specific plant metabolite is decreased or increased as compared to a control plant. Here, the "control plant" is a plant satisfying the following conditions: (i) the plant is a wild-type plant whose content of a plant metabolite is not regulated; (ii) the plant is of the same species or the same variety as the plant whose content of a plant metabolite is regulated; and (iii) the plant is cultivated or cultured under the same conditions as the plant whose content of a plant metabolite is regulated. Alternatively, the "control plant" also encompasses a plant satisfying the following conditions: (i) the plant is a transformed plant into which a gene used as a control or a part of the gene is introduced, and the gene here is not involved in regulation of a content of a plant metabolite; (ii) the plant is of the same species or the same variety as the plant whose content of a plant metabolite is regulated; and (iii) the plant is cultivated or cultured under the same conditions as the plant whose content of a plant metabolite is regulated.

For example, the phrase "content of plant metabolite is regulated" preferably means that a content of a specific plant metabolite is decreased or increased by 10% or more. The "10% or more" of decrease or increase above is preferably 20% or more, more preferably 30% or more, much more preferably 40% or more, and the most preferably 50% or more of decrease or increase. The "increase or decrease" here is accomplished preferably in a plant on which topping for removing an apical bud and an axillary bud has been carried out. However, the "increase or decrease" may be accomplished in a plant on which topping has not been carried out. The content is "regulated" preferably in a specific tissue such as a leaf or a root, though not limited to this. Note that the topping is carried out on various crops and is an important process that has a large effect on quality and yield of crops.

The term "transformed plant" as used in the present specification indicates a genetically modified plant (also called a transgenic plant) in which DNA introduced into a plant is integrated into a host genomic DNA. In addition to such a genetically modified plant, the "transformed plant" here encompasses a transiently transformed plant in which DNA introduced into a plant is not integrated into a host genomic DNA. Further, the term "transformed plant" indicates a transformed plant cell prepared by using the vector of the present invention, a plant body originating from the transformed plant cell or a part of the plant body. Further, as described below, the "transformed plant" may also be a progeny that receives, through the transgenic plant cell, a genome into which a desired polynucleotide of the present invention is integrated. The "transformed plant" may also be a plant cell, a plant body, a part of the plant body, or a seed.

In the present invention, a plant material to be a target of transformation indicates any of whole plant bodies, plant organs (e.g., root, stalk, leaf, seed, embryo, ovule, shoot apex, anther, and pollen), plant tissues (e.g., epidermis, phloem, parenchyma, xylem, vascular bundle, palisade tissue, and spongy tissue), plant cells including cultured plant cells (e.g., suspension cultured cell) and protoplasts, segments of leaves, and calluses.

The plant used for transformation is not specifically limited, but preferably a dicotyledonous plant. In particular, a solanaceous plant or an asteraceae plant is preferable. Examples of the solanaceous plant are *Duboisia, Anthocericis, Salpiglessis, Nicotiana*, and the like. Examples of the asteraceae plant are *Eclipta, Zinnia*, and the like. Among the plants above, solanaceous plants are more preferable and among the solanaceous plants, a *Nicotiana* plant is particularly preferable. The *Nicotiana* plant is not specifically limited as long as the plant belongs to *Nicotiana*. Examples of such *Nicotiana* plant are *Nicotiana acaulis, Nicotiana acuminata, Nicotiana acuminata* var. *multzjlora, Nicotiana africana, Nicotiana alata, Nicotiana amplexicaulis, Nicotiana arentsii, Nicotiana attenuata, Nicotiana benavidesii, Nicotiana benthamiana, Nicotiana bigelovii, Nicotiana bonariensis, Nicotiana cavicola, Nicotiana clevelandii, Nicotiana cordifolia, Nicotiana corymbosa, Nicotiana debneyi, Nicotiana excelsior, Nicotiana forgetiana, Nicotiana fragrans, Nicotiana glauca, Nicotiana glutinosa, Nicotiana goodspeedii, Nicotiana gossei, Nicotiana ingulba, Nicotiana kawakamii, Nicotiana knightiana, Nicotiana langsdorfi, Nicotiana linearis, Nicotiana longiflora, Nicotiana maritima, Nicotiana megalosiphon, Nicotiana miersii, Nicotiana noctiflora, Nicotiana nudicaulis, Nicotiana obtusifolia, Nicotiana occidentalis, Nicotiana occidentalis* subsp. *Hesperis, Nicotiana otophora, Nicotiana paniculata, Nicotiana pauczjlora, Nicotiana petunioides, Nicotiana plumbaginifolia, Nicotiana quadrivalvis, Nicotiana raimondii, Nicotiana repanda, Nicotiana rosulata, Nicotiana rosulata* subsp. *Ingulba, Nicotiana rotundifolia, Nicotiana rustica, Nicotiana setchellii, Nicotiana simulans, Nicotiana solanifolia, Nicotiana spegauinii, Nicotiana stocktonii, Nicotiana suaveolens, Nicotiana sylvestris, Nicotiana tabacum, Nicotiana thyrsiflora, Nicotiana tomentosa, Nicotiana tomentosifomis, Nicotiana trigonophylla, Nicotiana umbratica, Nicotiana undulata, Nicotiana velutina, Nicotiana wigandioides*, and a hybrid of *Nicotiana* plants. Among the above *Nicotiana* plants, *Nicotiana benthamiana, Nicotiana rustica*, and *Nicotiana tabacum* are more preferable. Particularly preferable examples are *Nicotiana rustica*, and *Nicotiana tabacum* that are used as materials of leaf tobacco.

Once a desired polynucleotide contained in the vector of the present invention is integrated into a genome of a plant and the plant having such a genome is obtained, it is possible to obtain a progeny of this plant by sexual reproduction or asexual reproduction of such a plant. Further, for example, a seed, a leaf, a stalk, a root, a stamen, a pollen, a callus or a protoplast obtained from the plant or its progeny can be used to proliferate the plants in each of which a desired polynucleotide is introduced into the genome. Therefore, the present invention includes a plant into which a desired polynucleotide in the vector of the present invention is introduced or a plant that is a progeny of this plant or a tissue derived from the above plant or the progeny that has the same nature as the plant.

As a method of transformation, a method conventionally known to a person skilled in the art can be used. Preferable examples of such a method are an *Agrobacterium* method, a particle gun method, a PEG-calcium phosphate method, and an electroporation method. These methods are broadly divided into a method using *Agrobacterium* and a method in which introduction is carried out directly into a plant cell. In particular, employing the *Agrobacterium* method is preferable. Examples of *Agrobacterium* preferably used in transformation are bacterial strains GV2260, LBA 4404 and C58 of *Rhizobium* radiobacter (old name: *Agrobacterium tumefaciens*). In a case where transformation is carried out by the *Agrobacterium* method, pBI binary vectors can be preferably used. Note that for preparation of *Agrobacterium* for transformation having a target vector, a conventionally known method can be used.

The transformed plant cell into which the gene is introduced is first selected according to resistance to an agent using the above-described selection marker gene. Then, the transformed plant cell is reproduced in the form of a plant body by a conventional method. The reproduction of the plant body from the transformed cell can be performed by a method conventionally known to a skilled person, in accordance with a type of the plant cell.

Whether or not a gene is introduced into a plant can be checked by, for example, PCR, Southern hybridization and Northern hybridization. For example, DNA is prepared from a transformed plant and primers specific to a polynucleotide introduced is designed. Then, PCR is carried out by using thus prepared DNA as a template. After the PCR, for example, agarose gel electrophresis, polyacrylamidogel electrophresis, capillary electrophoresis, and the like are carried out on an amplified product. Further, the amplified product is stained by ethidium bromide, SYBR Green solution, and the like, and detected. Thereby, whether or not transformation has occurred can be checked. Alternatively, it is also possible to perform PCR by use of primers labeled in advance by fluorescent dye or the like and then to detect an amplified product. As a further alternative, it is possible to employ a method in which the amplified product is bound to a solid phase such as a microplate or the like and the amplified product is checked by fluorescence or enzyme reaction. Alternatively, it is possible to check, by expression of the reporter gene, whether or not a plant cell is transformed. Whether or not the VIGS vector is introduced into a plant can be checked by checking infection and amplification of a recombinant plant virus integrated into the VIGS vector in each tissue of the plant. The infection and amplification of the recombinant plant virus can be checked by RT-PCR or RT-QPCR each of which uses total RNA extracted from each tissue and a PCR primer for virus genome.

As a result of the above procedures, it is possible to obtain a transformed plant whose expression of the following genes in the plant is modified: TTF_#20 gene, TTF_#53 gene, TTF_#54 gene, TTF_#55 gene, TTF_#56 gene, TTF_#80 gene, TTF_#84 gene, TTF_r20 gene, TTF_r25 gene, TTF_r33 gene, TTF_r35 gene, TTF_r40 gene, TTF_r48 gene, TTF_r49 gene, TTF_r66 gene, TTF_r84 gene or TTF_r86 gene.

In the "transformed plant whose content of a plant metabolite is regulated", an amount of a specific plant metabolite is decreased or increased. Accordingly, for example, a "tobacco whose content of a plant metabolite is regulated" can be used for production of leaf tobacco whose component is different in terms of quantity or quality from that of conventional leaf tobacco. By using such "leaf tobacco whose content of a plant metabolite is regulated", it is possible to further widen a range of taste and flavor of tobacco products created by blending. Here, the "leaf tobacco" indicate materials of tobacco products. Such materials are obtained by drying leaves (including stalks) of *Nicotiana* plants harvested. The *Nicotiana* plants that can be used for "leaf tobacco" are *Nicotiana tabacum* and *Nicotiana rustica*. Further, the tobacco products typically encompass cigarette, cigar, pipe, snuff, and chewing tobacco, but the tobacco products are not limited to the tobacco.

Note that the present invention can be restated as follows.

That is, a polynucleotide set forth in any one of the following (f), (g), and (h), the polynucleotide having a function of increasing or decreasing a content of a plant metabolite:

(f) a polynucleotide consisting of the base sequence of any of SEQ ID NO: 1 to 17;

(g) a polynucleotide consisting of a base sequence in which one or several bases are deleted, inserted, substituted or added in the base sequence of any of SEQ ID NO: 1 to 17; and (h) a polynucleotide that hybridizes, under a stringent condition, to a polynucleotide consisting of a complementary sequence of the polynucleotide (f).

A polynucleotide encoding a polypeptide set forth in any one of the following (i) and (j), the polypeptide having a function of increasing or decreasing a content of a plant metabolite:

(i) a polypeptide consisting of the amino acid sequence of any of SEQ ID NO: 18 to 32; and (j) a polypeptide consisting of an amino acid sequence in which one or several amino acids are deleted, inserted, substituted or added in the amino acid sequence of any of SEQ ID NO: 18 to 32.

A vector including: a promoter functioning in a plant cell; and at least one of the polynucleotides above, wherein the promoter and the polynucleotide are connected so as to make expression of the at least one polynucleotide possible in the plant cell.

A vector including: a promoter functioning in a plant cell; and a polynucleotide consisting of a consecutive base sequence that is a part of the polynucleotides above, wherein the promoter and the at least one polynucleotide are connected so that RNA is transcribed as RNA of a sense strand or an antisense strand of the at least one polynucleotide in the plant cell.

A vector of one of the following (k) and (l), the vector including: a promoter functioning in a plant cell; and a polynucleotide consisting of a base sequence having 21 or more consecutive bases that is a part of at least one of the polynucleotides above, wherein the promoter and the polynucleotide are connected so that RNA is transcribed so as to form a double-stranded RNA of the polynucleotide within the plant cell:

(k) a vector including both a sense strand and an antisense strand each as the polynucleotide; and (l) a vector to which the promoter is connected so that each of the sense strand and the antisense strand of the polynucleotide is transcribed, the promoter being connected to each of 5' end and 3' end of the polynucleotide.

A method for preparing a transformed plant cell whose content of a plant metabolite is decreased or increased, the method including the step of transforming a plant by using the vector above.

The above method for preparing a transformed plant cell whose content of a plant metabolite is decreased or increased, wherein the vector used for transforming the plant cell includes a promoter of any one of the following (m), (n), and (o):

(m) a promoter being active in constitutively expressing a target gene in a plant;

(n) a promoter being active in selectively expressing the target gene in a root tissue cell of a plant; and (o) a promoter being active in selectively expressing the target gene in a root cortex cell of the plant.

A method for preparing a transformed plant cell whose content of a plant metabolite is decreased or increased, the method employing a plant cell transformation method of any one of the following (p) and (q):

(p) a method performed through mediation of *Agrobacterium* having the vector; and (q) a method performed by bombardment of fine particles to which the vector is adhered.

A method for preparing the above transformed plant cell, the method including the step of reproducing a plant body from the transformed plant cell.

In the method for preparing the transformed plant cell, the transformed plant cell is more preferably a cell of a dicotyledonous plant. Much more preferably, the dicotyledonous plant is a solanaceous plant. Particularly preferably, the solanaceous plant is *Nicotiana* plant. Most preferably, the *Nicotiana* plant is *Nicotiana tabacum*.

Further, in the method for preparing the transformed plant cell, the transformed plant is preferably a plant cell or a plant body.

Further, the present invention encompasses (i) a transformed plant prepared by any of the methods above for preparing the transformed plant and (ii) a progeny of the transformed plant.

The present invention encompasses (i) a tobacco material (leaf tobacco) obtained from the plant whose content of a plant metabolite is decreased or increased, the plant being *Nicotiana tabacum*, and (ii) a tobacco product produced by using the tobacco material.

The vector of the present invention is a vector allowing production of a transformed plant whose content of a plant metabolite is regulated, the vector including a part of the above polynucleotide.

The following provides Examples and the embodiments of the present invention are explained in more detail. Certainly, the present invention is not limited to the following Examples and various embodiments are possible in regard to details. Further, the present invention is not limited to the description of the embodiments above, but may be altered by a skilled person within the scope of the claims. An embodiment based on a proper combination of technical means disclosed in different embodiments is encompassed in the technical scope of the present invention. All documents described in the present specification are incorporated herein as references.

EXAMPLES

Example 1

Plant Hormone Treatment of Root Segments

An apical bud (1-2 cm) cut from a seedling plant of sterilely cultivated tobacco (*Nicotiana tabacum*, varieties: Burley21 and LA Burley21) was cultured for approximately a month on a ½ MS agar medium (culture vessel: plant box, volume: 50 ml, containing 0.65% agar and 1.5% sucrose). A root of thus grown seedling plant was picked. Then, a root segment whose length was approximately 1 cm was tested. The root segment was a center portion of the root from which a tip portion including a root apex and a base portion having a lot of lateral roots were removed. Note that LA Burley21 is an isogenic line of Burley21. The LA Burley21 is a strain mutated at both of two regulatory loci (Nic1 and Nic2) involved in biosynthesis of nicotine, so that nicotine-related alkaloids such as nicotine are scarcely accumulated (Non-Patent Literature: Legg et al., 1970, Crop Sci, 10., 212.). Further, as compared to expression of nicotine biosynthesis enzyme gene in Burley21, the expression of nicotine biosynthesis enzyme gene is severely suppressed in the LA Burley21 (Non-Patent Literature: Hibi et al., 1994, Plant Cell., 6, 723-35.).

(Jasmonate Treatment)

The following procedures were used for obtaining a total RNA sample for clarifying genes inducible by jasmonate.

The root segments were precultured (80 rpm) in the dark at 25° C. in a HF modified liquid medium containing 1% sucrose and 5 µM indole acetate (IAA) (pH5.8, Non-Patent Literature: Mano et al., 1989, Plant Sci, 59, 191-201.). After 24 hour culturing, the root segments were washed with sterile water. Then, the root segments were cultured on 40 ml of HF liquid medium (culture vessel: 100 ml conical flask) containing 1% sucrose and 0.5 µM methyl jasmonate (MeJA). Part of the root segments washed with the sterile water after the preculture were cultured as a control on a HF modified liquid culture containing 1% sucrose and 5 µM IAA. Approximately 10 root segments were collected at each time point of 0, 30, 60, and 120 minutes after the start of the culturing. At each time point above, the root segments collected were immersed in 0.4 ml of RNAlater (product name, Ambion Ltd.) and stored at −30° C. until RNA extraction. For replication of this experiment, the root segments were collected into 3 tubes at each time point in each experimental lot. Then, by using RNeasy Plant Mini Kit (product name, QIAGEN), the total RNA was extracted from the root segments.

From thus obtained samples, cDNA was synthesized. Thus synthesized cDNA was used to check, by quantitative PCR, a change in amount of transcription products including 4 types of nicotine synthase genes (PMT1, ODC1, MPO1, and QPT). These 4 types of nicotine synthase genes are known to be inducible by jasmonate. As a result, a large increase in the amount of the transcription products was observed in the time period from 60 to 120 minutes after the start of the culturing. Therefore, the total RNA obtained was considered to be useful for screening of genes inducible by jasmonate.

(Auxin Removing Treatment)

The following procedures were taken for obtaining total RNA samples for clarifying genes inducible by removal of auxin from liquid culture medium.

The root segments were precultured for 24 hours on a HF modified medium containing 1% sucrose and 5 µM IAA and then washed with sterile water. Further, the root segments were cultured on a HF modified medium containing 1% sucrose. Part of the root segments were cultured as a control on a HF modified medium containing 1% sucrose and 5 µM IAA. At each time point of 0, 1, 2, and 4 hours after the start of the culturing, approximately 10 root segments were collected. Then, as in the case of the jasmonate treatment, total RNA samples were extracted from the root segments.

In regard to these samples, there was a change in amount of a transcription product of known nicotine synthase gene whose transcription was regulated by presence of auxin. Therefore, the total RNA obtained was considered to be useful for screening of genes to be inducible by removal of auxin.

(Auxin Treatment, Ethylene Treatment)

Similar experiments were performed for clarifying genes whose expression was inducible by addition of auxin or ethylene.

The root segments were precultured for 24 hours on a HF modified medium containing 1% sucrose and then washed with sterile water. Further, the root segments were cultured on a HF modified medium containing (i) 1% sucrose and (ii) 1 µM IAA or 5 µM 1-aminocyclopropane-1-carboxylic acid (ACC) that was a precursor of ethylene in a plant body. Part of thus precultured root segments were cultured as a control on a HF modified medium containing 1% sucrose. At each time point of 0, 30, and 60 minutes after the start of the culturing, approximately 10 root segments were collected. Then, as in the case of the jasmonate treatment, total RNA samples were extracted from the root segments.

Example 2

Topping of Tobacco Plant Individual

For clarifying genes expressed in roots in response to topping (also called decapitation) in which apical bud sections of a plant individual is removed, the following experiment was carried out and total RNA was extracted. First, a tobacco plant (variety: Tsukuba No. 1) was grown in a phytotron (Koitotron, manufactured by Koito Industry Ltd.) whose conditions were set as follows: 12 hours/26° C./humidity of 60% (light period) and 12 hours/18° C./humidity of 60% (dark period). Then, after one month from seeding, the Tobacco plant was transplanted into a 12 cm terracotta pot in which vermiculite was filled. Then, 60 to 75 ml of 2000-fold diluted Hyponex (HYPONEX JAPAN Corp. Ltd.) was provided every day. This was intended to also serve as watering. Topping was carried out 18 days after the Tobacco plant was transplanted. In the topping, lower 12 leaves were left on the Tobacco plant. At a time before the topping and each time point of 1, 3, 9, 24, and 48 hours after the topping, roots were taken from the plant individual and provided for total RNA extraction. As a control, roots were taken from an individual on which the topping was not performed. Samples were taken from 4 individuals at each one time point and the samples were used for replication of the experiment. The roots taken was immediately frozen by using liquid nitrogen and stored at −80° C. Thus frozen roots were ground by using a pestle and a mortar in liquid nitrogen. Then, total RNA was extracted. The extraction of the total RNA was carried out as in Example 1.

Example 3

Selection of Genes By Microarray Analysis

The total RNA obtained in Examples 1 and 2 were provided for microarray analysis.

A microarray is a 44K custom array manufactured on contract by Agilent Technologies Inc. The microarray has probes for assembled base sequences obtained by clustering base sequences from terminal sequence information of a full-length cDNA library (*Nicotiana tabacum* cv. Tsukuba No. 1) that the applicant has and from sequence information of *Nicotiana tabacum* gene registered in GenBank.

Hybridization and labeling were carried out by a method according one-color protocol (file name: One-Color Microarray-Based Gene Expression Analysis, ver 5.5, February 2007) recommended by Agilent Technologies Inc.

Proceeding to microarray data analysis, BLASTX homology search was performed by using KOG database (ftp://ftp.ncbi.nih.gov/pub/COG/KOG/kyva, version 2003/03/02). As a result of this search, a list of genes was produced. Here, each of the genes in the list was considered to encode a transcription factor from among the assembled base sequences. Based on this list, microarray data was analyzed by using GeneSpring GX (Agilent Technologies Inc.).

(Selection of Genes Inducible by Jasmonate)

The genes inducible by jasmonate were selected as follows. First, in an experiment in which the MeJA treatment was performed on root segments of the variety Burlay21, microarray signals of genes at a time point of 30 minutes or 60 minutes after the MeJA treatment were compared with microarray signals of genes before the MeJA treatment. Then, each gene whose microarray signal ratio in the comparison was 2 or higher was selected. Further, at a time point of 30 minutes or 60 minutes after the MeJA treatment, microarray signals of genes were compared with genes of the control. Then, each gene whose microarray signal ratio was 2 or higher was selected. Consequently, a union of the genes selected in the above two cases were determined to be the genes inducible by jasmonate.

(Selection of Genes Influenced By Nic1 and Nic2 Loci)

Under a condition where the MeJA treatment has not been carried out or at the time point 30 minutes after MeJA induction treatment, microarray signals of genes of wild-type Burley21 was compared with microarray signals of genes of low-nicotine-type LA Burley21. Then, each gene of wild-type Burley21 whose signal ratio was 2 or higher in the above comparison was selected. The genes from wild-type Burley21 here were selected as genes influenced by Nic1 and Nic2 loci.

(Selection of Genes Inducible by Auxin or Ethylene)

The following procedures were taken for selection of genes inducible by addition of auxin or ACC. First, microarray signals of genes at a time point 1 hour or 2 hours after the addition of auxin or ACC were compared with microarray signals of genes before the addition of auxin or ACC. Then, each gene whose microarray signal ratio was 2 or higher was selected. Then, at a time point 1 hour or 2 hours after the addition of auxin or ACC, the microarray signals of the genes were compared with microarray signals of genes of the control. Then, each gene whose microarray signal ratio was 2 or higher was selected. Consequently, a union of the genes of the above two cases were determined to be genes inducible by auxin or ethylene.

(Selection of Genes Inducible by Removal of Auxin)

At a time point 1 hour or 2 hours after the removal of auxin, microarray signals of genes were compared with microarray signals of genes of the control. Then, each gene whose microarray signal ratio was 2 or higher was selected. The genes here were selected as genes inducible by removal of auxin.

(Selection of Genes Induced by Topping)

Microarray signals of genes 9 hours after the topping were compared with microarray signals of genes before the topping. Then, each gene whose microarray signal ratio was 2 or higher was selected as a gene induced by topping.

Example 4

Selection of Genes According to Known Information

There are genes whose expression is induced in response to treatment that induces synthesis of nicotine in tobacco. Such treatment includes jasmonate treatment and wounding. Such genes were extracted according to known information disclosed in the following Non-Patent Literatures: Proc. Natl. Acad. Sci (2003) 100(14) p 8595-8600: Supplement Data Table2, Plant Sci. (2000) 158 p 19-32, Plant J. (2005) 44 p 1065-1076, Plant Physiol (2005) 139 p. 949-959: Supplement Data, Nature (2007) 448 p 661-665, Nature (2007) 448 p 666-673, Plant Physiol (2002) 129 p. 661-677: Table1, Plant Cell (2007) 19 p 2225-2245: Supplement Data (Table1), Plant Cell (2004) 16 p 1938-1950, Gene Dev. (2004) 18 p 1577-1591, Plant Molecular Biology (2005) 58 p 585-595, J. of Biochemistry (2004) 279(53) p 55355-55361, Plant Molecular Biology (2004) 55 p 183-192, Plant Cell Physiol (1998) 39(10) p 993-1002, Plant Molecular Biology (2004) 55 p 743-761, Plant Molecular Biology (2006) 60 p 699-716, Plant Molecular Biology (2001) 45 p 477-488, EMBO J (1991) 10(7) p 1793-1802, EMBO J (1999) 18(16) p 4455-4463, Plant J. (2001) 25(1) p 43-53, J. of Biochemistry (2004) 279(51) p 52940-52948, Plant Physiol (2007) 144 p 1680-1689, and Plant Physiol (1997) 115 p 397-407. In regard to these gene sequences, BLAST® search was carried out on the assembled base sequences. As a result, corresponding 250 genes were selected. From among these 250 genes, 45 genes respectively having high gene expression levels in roots were extracted. Further, 13 types of genes were selected. Each of these 13 types of genes selected were either a gene that was not on the 44K custom array described in Example 3 or a gene in which no unique probe sequence was designed.

Meanwhile, by using the assembled base sequences as a query, Blastx search was carried out on Non-redundant protein sequence(nr) database of National Center for Biotechnology (NCBI). In the Blastx search, assembled base sequences that hit on the following amino acid sequence were selected. That is, the amino acid sequence of thus selected assembled base sequences had IAA, auxin, bHLH, MYC, C2H2, zinc finger, ZAT, WZF, ZPT, or ethylene as a keyword. Further, by using EAR motif (SEQ ID NO: 94 to 113) shown in Table 1 as a query, tblastn search was carried out on the assembled base sequences. Thereby, assembled base sequences having the EAR motif were extracted. The assembled base sequences selected above were 178 genes in total. From these 178 genes, 27 genes respectively having a high gene expression levels in roots were selected.

TABLE 1

| GENE NAME | MOTIF NAME | | SPECIES |
|---|---|---|---|
| IAA1 | TELRLGLPG | 94 | ARABIDOPSIS THALIANA |
| IAA20 | TDLRLGLSF | 95 | ARABIDOPSIS THALIANA |
| IAA12 | ELELGLGL | 96 | ARABIDOPSIS THALIANA |
| IAA11 | ELGLTLSL | 97 | ARABIDOPSIS THALIANA |
| IAA29 | ELDLGLSL | 98 | ARABIDOPSIS THALIANA |
| IAA34 | DLGLSLRT | 99 | ARABIDOPSIS THALIANA |
| IAA31 | NLSLSLTF | 100 | ARABIDOPSIS THALIANA |
| IAA26 | KKLELRL | 101 | ARABIDOPSIS THALIANA |
| NtERF3 | IDLDLNLAP | 102 | TOBACCO |
| AtERF4 | LDLDLNLPP | 103 | ARABIDOPSIS THALIANA |
| AtERF8 | LDLDLNLAP | 104 | ARABIDOPSIS THALIANA |
| OsERF3 | FDLDLNRP | 105 | RICE |
| AtERF3 | FQFDLNFPP | 106 | ARABIDOPSIS THALIANA |
| AtERF10 | LDLNASP | 107 | ARABIDOPSIS THALIANA |
| AtERF11 | LDLDLNFPP | 108 | ARABIDOPSIS THALIANA |
| ZAT10 | FDLNIPP | 109 | ARABIDOPSIS THALIANA |
| ZAT11 | LDLNLTP | 110 | ARABIDOPSIS THALIANA |
| ZAT1 | IDLNLP | 111 | ARABIDOPSIS THALIANA |

TABLE 1-continued

| GENE NAME | MOTIF NAME | | SPECIES |
|---|---|---|---|
| ZCT1 | LDLNLTP | 112 | *CATHARANTHUS ROSEUS* |
| ZCT3 | FDLNLPA | 113 | *CATHARANTHUS ROSEUS* |

Example 5

Yeast One-Hybrid Screening

In addition to the selection in the microarray analysis in Example 3 and the selection according to known information in Example 4, selection of genes was carried out by Yeast One-Hybrid Method described below. For the Yeast One-Hybrid selection, Matchmaker™ One-Hybrid Library Construction & Screening Kit (Takara Bio Inc.) was used. The Yeast One-Hybrid selection here was carried out by following a manual attached to the above kit. Note that as to yeast transformation method, High efficiency method found at the following homepage address (www.umanitoba.ca/faculties/medicine/biochem/gietz/method.html) was partially improved and used.

(1. Yeast Transformation)

The following procedures were used to prepare a yeast competent cell for transformation. First, Y187 yeast strain was cultured on a YPDA plate at 30° C. for 3 days. Then, a single colony (2 to 3 mm) of the Y187 yeast strain was picked. Further, this single colony of the Y187 yeast strain was put in 6 ml of 2×YPDA liquid medium and shaken for approximately 24 hours at 200 rpm. Thereby, preculture was prepared. Then, 2 ml of this preculture was added to 100 ml of 2×YPDA liquid medium. Further, the culture (for 2 to 4 hours) was shaken at 30° C. until OD600 becomes approximately 0.5. Then, thus cultured yeast was harvested by low-speed centrifugation for 5 minutes and washed with sterile water. Ultimately, the yeast was suspended in 1 ml of sterile water and every 300 µl of thus obtained yeast suspension was poured into a separate 1.5 ml tube.

The following procedures were taken for yeast transformation. First, the yeast suspension was subjected to centrifugation for 30 seconds at 10000 rpm and supernatant was removed. Then, to a yeast pellet thus prepared, 360 µl of Transformation Mix (50% PEG3500: 240 µl, 1M lithium acetate: 36 µl, dH$_2$O: 64 µl, 10 mg/ml denatured carrier DNA: 10 µl, plasmid DNA: 10 µl) prepared in advance was added and fully suspended by vortex. Further, a heat shock was given by keeping thus obtained suspension at 42° C. for 20 minutes. Subsequently, the suspension was subjected to centrifugation for 30 seconds at 10000 rpm, and a supernatant was removed. The pellet of the centrifugation was then gently suspended in 1 ml of sterile water. Further, 200 µl of thus obtained suspension was plated onto an SD plate and cultured at 30° C. for 2 to 7 days.

(2. Preparation of cDNA for Screening)

The following procedures were taken for preparing cDNA for screening. First, 24-hour preculture of root segments was carried out on a HF modified medium, described in Example 1, that does not contain a plant hormone. Then, IAA or ACC was added and the root segments were further cultured. Subsequently, by using, as a template, total RNA extracted from the root segments, the cDNA for screening was prepared according to a manual attached to the kit.

(3. Preparation of Bait Vector)

With reference to information on presence of known cis-elements and promoter activity, the following two types of Bait sequences were selected from promoter sequences of nicotine biosynthesis enzyme genes. As one of the two types of Bait sequence, a polynucleotide consisting of 90 bases including ARE motif (GAGCAC: Non-Patent Literature: Guilfoyle et al., 2002, Plant Molecular Biology, 49, 373-385.) was selected as a QPT1 Bait sequence (SEQ ID NO: 33). This polynucleotide was selected from a quinolinate phosphoribosyltransferase gene (QPT1, GenBank Accession Number AJ748262) of tobacco. The quinolinate phosphoribosyltransferase gene has conventionally known expression specificity in roots and wound inducibility. As another type of the Bait sequences, a sequence in which actaataattgcaccgagacaaac (24mer: SEQ ID NO: 93) of TAA-Box/ARE motif from a putrecine N-methyltransferase gene (PMT1, GenBank Accession Number AF126810) was repeated three times and connected was selected as PMT1 Bait sequence (SEQ ID NO: 34). These sequences were cloned into pHis2.1 Vector according to a manual attached to the kit.

(4. Screening)

For screening, for each 360 µl of Transformation Mix, 250 ng of Bait Vector, 150 ng of pGADRec Vector, 100 ng of cDNA were used as plasmid DNA. In this screening, a colony grown on an PD plate of TDO (-His/-Leu/-Trp) containing 10 mM 3-Amino-1,2,4-Triazole (3-AT, Sigma-Aldrich Corporation) was selected as a positive clone. Note that for PMT1 Bait, an SD plate of TDO containing 20 mM 3-AT was used. The positive colony was re-streaked onto an SD plate of TDO containing 3-AT and clones thus grown were selected. Further, base sequences that the clones have respectively were analyzed. By using these base sequences as a query, blastx search and blastn search were carried out. Thereby, the following genes were selected: (i) genes whose possibility of encoding a transcriptional factor was suggested; or (ii) genes encoding a protein whose function was unknown. By transforming the yeast again with use of thus selected genes, genes whose bindability to Bait was reproducible were selected.

Example 6

VIGS Assay

Regarding each of the 149 types of genes selected in total in Examples 3, 4, and 5, a relation with nicotine content in leaf of *Nicotiana* plant was examined by VIGS assay using a TRV vector.

(Construction of TRV Vector)

The following documents can be used as references for details of the TRV vector: Ratcliff F. et al., 2001, Plant Journal, 25, 237-245, Liu Y. et al., 2002, Plant Journal, 31, 777-786, Liu Y. et al., 2002, Plant Journal, 30, 415-429, Burch-Smith T. M. et al., 2004, Plant Journal, 39, 734-746, and Baulcombe D., 2004, Nature, 431, 356-363; and U.S. Pat. No. 6,369,296 and U.S. Pat. No. 7,229,829.

For preparation of a construct of VIGS, pSP221 was used. This pSP221 is TRV-RNA2 vector that employs Gateway (Registered Trademark) system. This pSP 221 was prepared, by inserting a TRV-RNA2 expression cassette of pTRV2-attR2-attR1 (Non-Patent Literature: Liu Y. et al, 2002, Plant Journal, 31, 777-786) into a multiple cloning site of pSP 202 originating from a binary vector pBI 121. Note that pSP 202 was modified by inserting Amp gene of pUC18 into pBI121 so that pSP 202 could be used in selection by carbenicillin.

By using primers specific to the base sequences of the 149 types of genes selected in total in Examples 3, 4, and 5, DNA fragments to be inserted into pSP 221 were amplified by PCR. Among the primers, Table 2 shows primers used for preparing the DNA fragments each having a partial base sequence of TTF_#20 gene, TTF_#53 gene, TTF_#54 gene, TTF_#55 gene, TTF_#56 gene, TTF_#80 gene, TTF_#84 gene, TTF_r20 gene, TTF_r25 gene, TTF_r33 gene, TTF_r35 gene, TTF_r40 gene, TTF_r48 gene, TTF_r49 gene, TTF_r66 gene, TTF_r84 gene or TTF_r86 gene. Note that PCR amplification was carried out by using PfuUltra High-Fidelity DNA Polymerase (product name, Stratagene Corporation) and GeneAmp PCR System 9700 (product name, Applied Biosystems Inc.). PCR amplification was carried out by (a) heating at 95° C. for 2 minutes, (b) carrying out 35 cycles of heating at 95° C. for 30 seconds and heating at 65° C. for 2 minutes, and then (c) heating at 72° C. for 10 minutes. Further, PCR amplification was carried out by using a reverse transcription reaction product as a template. This reverse transcription reaction product was prepared from the total RNA described in Example 1 by using Omniscript RT Kit (product name, QIAGEN). Moreover, cloning of a PCR product was carried out by using pENTR/D-TOPO cloning kit (product name, Invitrogen Corporation).

TABLE 2

| PRIMER NAME | SEQUENCE (SEQ ID NO) |
| --- | --- |
| TTF_#20_TRV_F | CACCACAAGATACAATTGCAGCTGCTAC (SEQ ID NO: 35) |
| TTF_#20_TRV_R | GGCTAAAGCAATGACTTCAGTAAGCG (SEQ ID NO: 36) |
| TTF_#53_TRV_F | CACCATTGCTTACATAACTGAGATGC (SEQ ID NO: 37) |
| TTF_#53_TRV_R | ACGATATGATTCTTCACTACACTTTATGCC (SEQ ID NO: 38) |
| TTF_#54_TRV_F | CACCGCATCAAGTGCTGAAAACATAGCC (SEQ ID NO: 39) |
| TTF_#54_TRV_R | CACTAATGTTAAAACAGTCATACCTGGCC (SEQ ID NO: 40) |
| TTF_#55_TRV_F | CACCATTATTACCATCCTTATAATTTTCCC (SEQ ID NO: 41) |
| TTF_#55_TRV_R | GAACTTATCCTGAATCTACCTATACTCCC (SEQ ID NO: 42) |
| TTF_#56_TRV_F | CACCGAGCAATGATTCAAGTATGGGG (SEQ ID NO: 43) |
| TTF_#56_TRV_R | CGATGTCTACTACACAGAGAATTGCC (SEQ ID NO: 44) |
| TTF_#80_TRV_F | CACCATCGTCGGAATTTCAATTTGCTACC (SEQ ID NO: 45) |
| TTF_#80_TRV_R | ATTGTTGAGAAGGGAAGGAAGTCACAGC (SEQ ID NO: 46) |
| TTF_#84_TRV_F | CACCATCTTGCCTACCGCCATTTTCC (SEQ ID NO: 47) |
| TTF_#84_TRV_R | TGTATGCATTTAACGAGGGGTCTAAAGG (SEQ ID NO: 48) |
| TTF_r20_TRV_F | CACCAAGAATTTAATAATGAGATTCGGC (SEQ ID NO: 49) |
| TTF_r20_TRV_R | ATCGAACAAATTGTTAAACTCACTGCG (SEQ ID NO: 50) |
| TTF_r25_TRV_F | CACCAAGTTCGCAGCAGAAATTCGTGACC (SEQ ID NO: 51) |
| TTF_r25_TRV_R | TACACATCTTCTATTGAGTCCTAATCCC (SEQ ID NO: 52) |
| TTF_r33_TRV_F | TATAATAATGAGATTCCACAGTCGGC (SEQ ID NO: 53) |
| TTF_r33_TRV_R | AATAAATACGTAGGTTTTAGTAGGTATATGC (SEQ ID NO: 54) |
| TTF_r35_TRV_F | CACCGATGATAGTTTATCTTTGAGAAAGGC (SEQ ID NO: 55) |
| TTF_r35_TRV_R | AACTTCAATTGAATTACATGAAAGAATGGC (SEQ ID NO: 56) |
| TTF_r40_TRV_F | CACCGAAGATGAGAAGAAACTGTAACTTGG (SEQ ID NO: 57) |
| TTF_r40_TRV_R | CTGGAGATTGTAAAAATGGTGATGAAGGC (SEQ ID NO: 58) |
| TTF_r48_TRV_F | CACCCATAACACAACACCTACTCTCCC (SEQ ID NO: 59) |
| TTF_r48_TRV_R | TATTGAAGTCAAAACGACCACCAATTTAGC (SEQ ID NO: 60) |
| TTF_r49_TRV_F | CACCAAAGGTTGATATCAAAACTTACAGCG (SEQ ID NO: 61) |
| TTF_r49_TRV_R | CTTCTTAAACCAGTGCTTTTCCTTTCAGG (SEQ ID NO: 62) |
| TTF_r66_TRV_F | CACCGCTATAGTTTATAAAATTACCAAGAACGTCG (SEQ ID NO: 63) |
| TTF_r66_TRV_R | TACATCATCATATACATGTGACATACGGG (SEQ ID NO: 64) |
| TTF_r84_TRV_F | CACCAGAAGCTGAAGGAGAAGAGAATATCGG (SEQ ID NO: 65) |
| TTF_r84_TRV_R | AAACAGGAGATGACCAGTTCCCAACC (SEQ ID NO: 66) |
| TTF_r86_TRV_F | CACCAAGAGAAATCCCTAAATGGCGACG (SEQ ID NO: 67) |
| TTF_r86_TRV_R | AGCACATTGTAAGTATACAGCAAAAGATGG (SEQ ID NO: 68) |
| GUS_TRV_F | CACCTACGGCAAAGTGTGGGTCAA (SEQ ID NO: 69) |
| GUS_TRV_R | TGTCTGGCTTTTGGCTGTGA (SEQ ID NO: 70) |

Base sequences of the DNA fragments amplified by PCR are shown, respectively, in SEQ ID NO: 71 (TTF_#20), 72 (TTF_#53), 73 (TTF_#54), 74 (TTF_#55), 75 (TTF_#56), 76 (TTF_#80), 77 (TTF_#84), 78 (TTF_r20), 79 (TTF_r25), 80 (TTF_r33), 81 (TTF_r35), 82 (TTF_r40), 83 (TTF_r48), 84 (TTF_r49), 85 (TTF_r66), 86 (TTF_r84), and 87 (TTF_r86).

In this way, each of the DNA fragments having the base sequences of any one of SEQ ID NO: 71 to 87 was cloned into a pENTR/D-TOPO vector. As a result, an entry clone for Gateway (Registered Trademark) system was attained. Further, for use as a control in VIGS assay, DNA of a partial base sequence of GUS gene was amplified by PCR by using primers shown in Table 2. In this PCR amplification, the binary vector pBI121 was used as a template. Then, thus amplified DNA was cloned into pENTR/D-TOPO vector (entry clone). A base sequence of this DNA obtained by PCR is shown in SEQ ID NO: 88.

Each DNA fragment having the base sequence of any one of SEQ ID NO: 71 to 88 had been cloned into pENTR/D-TOPO vector. Thus obtained DNA fragment was integrated into pSP221 that was TRV-RNA2 vector. This integration was carried out by attL×attR recombination reaction by use of Gateway (Registered Trademark) LR Clonase II. Note that *E. coli* containing a target recombinant construct was selected in the presence of μg/mL carbenicillin. As a result of the above procedures, the following TRV/RNA2 constructs were obtained: pTRV2-TTF_#20, pTRV2-TTF_#53, pTRV2-TTF_#54, pTRV2-TTF_#55, pTRV2-TTF_#56, pTRV2-TTF_#80, pTRV2-TTF_#84, pTRV2-TTF_r20, pTRV2-TTF_r25, pTRV2-TTF_r33, pTRV2-TTF_r35, pTRV2-TTF_r40, pTRV2-TTF_r48, pTRV2-TTF_r49, pTRV2-TTF_r66, pTRV2-TTF_r84, pTRV2-TTF_r86, and pTRV2-GUS. These TRV-RNA2 constructs were introduced by the electroporation method, into *Agrobacterium* strain GV2260 (See Non-Patent Literature: Deblaere R., 1985, Nucleic Acids Res., 13, 4777-88.).

Further, in addition to the above TRV-RNA2 constructs, a TRV-RNA1 construct (GenBank Accession No. AF406990) was similarly introduced into *Agrobacterium* strain GV2260. The TRV-RNA1 construct encodes RNA-dependent RNA replication enzyme of Tobacco Rattle Virus.

(Virus Infection)

Each of *Agrobacterium* containing the TRV-RNA2 construct and *Agrobacterium* containing the TRV-RNA1 construct was cultured overnight at 28° C. in 10 ml of LB liquid medium (containing 50 mg/L kanamycin). On the following day, a part of this preculture was added to 50 ml of LB liquid medium (containing 50 mg/L kanamycin) and cultured overnight at 28° C. Each *Agrobacterium* collected by centrifugation at 3000×g for 15 min was suspended in 10 mM MES buffer (pH 5.7) so that a value of OD600 became 1.0. The MES buffer here contains 10 mM $MgCl_2$ and 150 μM Acetosyringone. Thus obtained suspension was gently shaken for 3 hours at a room temperature. Then, inoculum was prepared by mixing (i) *Agrobacterium* suspension containing the TRV-RNA1 construct and (ii) *Agrobacterium* suspension containing the TRV-RNA2 at a proportion of 1:1. *Nicotiana benthamiana* was cultivated in soil in a phytotron whose conditions were set as follows: 12 hours/25° C./humidity of 60% (light period) and 12 hours/18° C./humidity of 60% (dark period). Approximately 18 days after seeding, the inoculum was injected into leaves of plants. Then, the conditions for cultivation was changed to 12 hours/22° C./humidity of 60% (light period) and 12 hours/18° C./humidity of 60% (dark period) and the plants were cultivated for additional 17 days. In this period, the plants were transplanted into 9 cm terracotta pots. The injection of *Agrobacterium* was carried out onto fully expanded leaves by infilteration (Non-Patent Literature: Kapila et al, 1997, Plant Sci., 122, 101-108., Rossi et al., 1993, Plant Mol. Biol. Rep., 11, 220-229., and Van der Hoorn et al, 2000, Mol. Plant-Microbe Interact., 13, 439-446.) with use of 1 ml syringe having no needle.

On the 18th day from the injection, topping was carried out on half the number of the plants having received the injection. In the topping, an apical bud section was removed while 13 leaves were left. From the 18th day after the injection, all the plants having received the injection were cultivated under the following conditions: 12 hours/26° C./humidity of 60% (light period) and 12 hours/18° C./humidity of 60% (dark period). Then, on 24th day from the injection, all leaves and roots were collected. The leaves thus collected were ground after dried overnight by hot air at 70° C. (humidity 10%). Then, the leaves were used as samples for nicotine analysis. Further, after 18th day from the injection, all auxiliary buds having started developing were removed from all plants having received the injection.

(Measurement of Nicotine Content)

The following procedures were taken for analysis of nicotine contents. First, 5 ml of water, 10 ml of 0.5 g/L n-heptadecane-containing hexane and 2.5 ml of 8M NaOH were added to 0.3 g of dried leaf powder. Then, shaking was carried out for 60 minutes. Subsequently, a hexane layer (upper layer) was taken and used as a sample for the analysis. The analysis of nicotine contents was carried out by using a gas chromatograph (Agilent 6890N, Agilent Technologies Inc.) and DB-17 column (Agilent Technologies Inc.).

As a result of the VIGS assay described above, it was found that, among the 149 types of genes selected in total in Examples 3, 4, and 5, the following gene affects nicotine content per dry weight of a leaf of *Nicotiana* plant (FIG. 1, Table 3): TTF_#20 gene, TTF_#53 gene, TTF_#54 gene, TTF_#55 gene, TTF_#56 gene, TTF_#80 gene, TTF_#84 gene, TTF_r20 gene, TTF_r25 gene, TTF_r33 gene, TTF_r35 gene, TTF_r40 gene, TTF_r48 gene, TTF_r49 gene, TTF_r66 gene, TTF_r84 gene or TTF_r86 gene. Note that FIG. 1 shows each nicotine content in leaves of (i) a control plant to which *Agrobacterium* containing pTRV2-GUS was injected and (ii) a plant to which *Agrobacterium* containing TRV-RNA2 construct was injected. Into this TRV-RNA2 construct, a part of the gene of the present invention had been inserted. Moreover, Table 3 shows each ratio of nicotine contents in leaves of (i) a plant obtained by silencing the gene of the present invention and (ii) a control plant. As shown in FIG. 1 and Table 3, as compared to the control plant, silencing of the following genes increased, by 17% to 69%, the nicotine content of the leaves in *Nicotiana benthamiana* subjected to the topping: TTF_#20 gene, TTF_#53 gene, TTF_#54 gene, TTF_#55 gene, TTF_#56 gene, TTF_r20 gene, TTF_r25 gene, TTF_r33 gene, TTF_r35 gene, TTF_r40 gene, TTF_r48 gene and TTF_r66 gene. Further, as compared to the control, silencing of the following genes decreased, by 15% to 74%, the nicotine content of the leaves in *Nicotiana benthamiana* subjected to the topping: TTF_#80 gene, TTF_#84 gene, TTF_r49 gene, TTF_r84 gene, and TTF_r86 gene. As compared to the control, silencing of TTF_r66 gene increased, by approximately 40%, the nicotine content of the leaves in *Nicotiana benthamiana* under a condition where the topping had not been performed. The term "untreated" in FIG. 1 means that the topping had not been performed, whereas the term "topping" means that the topping had been performed.

TABLE 3

| | AFTER VIRUS INFECTION | |
|---|---|---|
| GENE | CASE WHERE TOPPING WAS CARRIED OUT | CASE WHERE TOPPING WAS NOT CARRIED OUT |
| TTF_#20 GENE | 138%** | 110% |
| TTF_#53 GENE | 167%** | 128%* |
| TTF_#54 GENE | 133%* | 108% |
| TTF_#55 GENE | 169%** | 109% |
| TTF_#56 GENE | 138%** | 124%* |
| TTF_#80 GENE | 85%* | 76%* |
| TTF_#84 GENE | 26%** | 55%* |
| TTF_r20 GENE | 117%* | 121% |

TABLE 3-continued

| | AFTER VIRUS INFECTION | |
|---|---|---|
| GENE | CASE WHERE TOPPING WAS CARRIED OUT | CASE WHERE TOPPING WAS NOT CARRIED OUT |
| TTF_r25 GENE | 131%* | 126% |
| TTF_r33 GENE | 146%** | 127%* |
| TTF_r35 GENE | 120%* | 92% |
| TTF_r40 GENE | 135%* | 91% |
| TTF_r48 GENE | 128%** | 143%* |
| TTF_r49 GENE | 80%* | 104% |
| TTF_r66 GENE | 105% | 146%* |
| TTF_r84 GENE | 72%* | 79% |
| TTF_r86 GENE | 69%** | 94% |

**SIGNIFICANTLY DIFFERENT VALUE AT SIGNIFICANCE LEVEL OF 1%
*SIGNIFICANTLY DIFFERENT VALUE AT SIGNIFICANCE LEVEL OF 5%

Example 7

Cloning of cDNA Having Full-Length ORF

TTF_#20 Gene

A full-length cDNA of TTF_#20 gene was obtained from a cDNA clone library that the applicant has. TTF_#20 gene was selected as a gene whose expression was inducible by addition of jasmonate and removal of auxin in the microarray analysis as described in Example 3. TTF_#20 gene has the base sequence of SEQ ID NO: 1. It is inferred that TTF_#20 gene encodes the amino acid sequence of SEQ ID NO: 18. This amino acid sequence has WRKY domain and accordingly TTF_#20 gene is predicted to be a transcription factor.

(TTF_#53 Gene)

A full-length cDNA of TTF_#53 gene was obtained from a cDNA clone library that the applicant has. TTF_#53 gene was selected as a gene whose expression was inducible by addition of jasmonate in the microarray analysis as described in Example 3. A base sequence of the full-length cDNA is shown in SEQ ID NO: 2. It is inferred that TTF_#53 gene encodes the amino acid sequence of SEQ ID NO: 19. This amino acid sequence has bHLH domain and accordingly TTF_#53 gene is predicted to be a transcription factor.

(TTF_#54 Gene)

A full-length cDNA of TTF_#54 gene was obtained from a cDNA clone library that the applicant has. TTF_#54 gene was selected as a gene whose expression was inducible by addition of jasmonate in the microarray analysis as described in Example 3. TTF_#54 gene was also selected as a gene whose expression was suppressed in LA Burley21. A base sequence of the full-length cDNA is shown in SEQ ID NO: 3. It is inferred that TTF_#54 gene encodes the amino acid sequence of SEQ ID NO: 20. This amino acid sequence has SANT domain, and accordingly TTF_#54 gene is predicted to be a transcription factor.

(TTF_#55 Gene)

A full-length cDNA of TTF_#55 gene was obtained from a cDNA clone library that the applicant has. TTF_#55 gene was selected as a gene whose expression was inducible by addition of jasmonate in the microarray analysis as described in Example 3. A base sequence of the full-length cDNA is shown in SEQ ID NO: 4. It is inferred that TTF_#55 gene encodes the amino acid sequence of SEQ ID NO: 21. This amino acid sequence has WRKY domain and accordingly TTF_#55 is predicted to be a transcription factor.

(TTF_#56 Gene)

A full-length cDNA of TTF_#56 gene was obtained from a cDNA clone library that the applicant has. TTF_#56 gene was selected as a gene whose expression was inducible by addition of jasmonate and removal of auxin in the microarray analysis as described in Example 3. A base sequence of the full-length cDNA is shown in SEQ ID NO: 5. In regard to TTF_#56 gene, no clear ORF was found in the base sequence.

(TTF_#80 Gene)

A full-length cDNA of TTF_#80 gene was obtained from a cDNA clone library that the applicant has. TTF_#80 gene was selected as a gene that responded to jasmonate and injury in Example 4. A base sequence of the full-length cDNA is shown in SEQ ID NO: 6. It is inferred that TTF_#80 gene encodes the amino acid sequence of SEQ ID NO: 22. This amino acid sequence has NadA domain and SufE domain and shows 64% homology with quinolinate synthetase of *Arabidopsis thaliana*.

(TTF_#84 Gene)

A full-length cDNA of TTF_#84 gene was obtained from a cDNA clone library that the applicant has. TTF_#84 gene was selected as a gene that responded to jasmonate and injury in Example 4. A base sequence of the full-length cDNA is shown in SEQ ID NO: 7. It is inferred that TTF_#84 gene encodes the amino acid sequence of SEQ ID NO: 23. Like the amino acid sequence of TTF_#84 gene, this amino acid sequence shows homology (66%) with quinolinate synthetase of *Arabidopsis thaliana*. TTF_#84 gene is a homolog of TTF_#80 gene.

(TTF_r20 Gene)

A full-length cDNA of TTF_r20 gene was not in a cDNA clone library that the applicant has. Accordingly, by using Primer 1 (5'-GGATTCCCGGGATTTTGAATTCTTG-3': SEQ ID NO: 89) and Primer 2 (5'-ATCGAACAAATTGT-TAAACTCACTGCGTA-3': SEQ ID NO: 90), PCR was performed. In this PCR, the reverse transcription reaction product described in Example 1 was used as a template. This provided a cDNA having a full-length ORF. TTF_r20 gene is selected as a gene inducible by auxin and ethylene in the microarray analysis as described in Example 3. A base sequence of this cDNA having the full-length ORF is shown in SEQ ID NO: 8. It is inferred that TTF_r20 gene encodes the amino acid sequence of SEQ ID NO: 24. This amino acid sequence has AP2 domain and accordingly TTF_r20 gene is predicted to be a transcription factor.

(TTF_r25 Gene)

A full-length cDNA of TTF_r25 gene was not in a cDNA clone library that the applicant has. Accordingly, by using Primer 3 (5'-CTTTCCCTCGTTTTATTAGCAGATCA-3': SEQ ID NO: 91) and Primer 4 (5'-CTATTTACAAGAAT-TAACGCTTAATCAATG-3': SEQ ID NO: 92), cDNA having a full-length ORF was obtained as in the case of TTF_r20 gene described above. TTF_r25 gene was selected as a gene inducible by auxin and ethylene in the microarray analysis as described in Example 3. A base sequence of this cDNA having the full-length ORF is shown in SEQ ID NO: 9. It is inferred that TTF_r25 gene encodes the amino acid sequence of SEQ ID NO: 25. This amino acid sequence has AP2 domain and accordingly TTF_r25 gene is predicted to be a transcription factor.

(TTF_r33 Gene)

A full-length cDNA of TTF_r33 gene was obtained from a cDNA clone library that the applicant has. TTF_r33 gene was selected as a gene inducible by auxin and ethylene in the microarray analysis as described in Example 3. A base sequence of this cDNA having the full-length ORF is shown in SEQ ID NO: 10. It is inferred that TTF_r33 gene encodes the amino acid sequence of SEQ ID NO: 26. This amino acid sequence has AP2 domain and accordingly TTF_r33 gene is predicted to be a transcription factor.

(TTF_r35 Gene)

A full-length cDNA of TTF_r35 gene was not in a cDNA clone library that the applicant has. Further, 5' upstream region and 3' downstream region of a transcription product could not be clarified even by RACE. In regard to TTF_r35 gene, only a polynucleotide (SEQ ID NO: 11) used in the VIGS assay could be isolated. Note that TTF_r35 gene was selected as a gene whose expression was suppressed by addition of jasmonate and removal of auxin in the microarray analysis as described in Example 3. A partial amino acid sequence that TTF_r35 gene is predicted to have is shown in SEQ ID NO: 27.

(TTF_r40 Gene)

A full-length cDNA of TTF_r40 gene was obtained from a cDNA clone library that the applicant has. TTF_r40 gene was selected as a gene inducible by jasmonate treatment and topping in the microarray analysis as described in Example 3. A base sequence of this full-length cDNA of TTF_r40 gene is shown in SEQ ID NO: 12. It is inferred that TTF_r40 gene encodes the amino acid sequence of SEQ ID NO: 28. This amino acid sequence has tify domain and accordingly TTF_r40 gene is predicted to be a transcription factor.

(TTF_r48 Gene)

A full-length cDNA of TTF_r48 gene was obtained from a cDNA clone library that the applicant has. TTF_r48 gene was selected as a gene inducible by jasmonate treatment and topping in the microarray analysis as described in Example 3. A base sequence of the full-length cDNA of TTF_r48 gene is shown in SEQ ID NO: 13. It is inferred that TTF_r48 gene encodes the amino acid sequence of SEQ ID NO: 29. This amino acid sequence has tify domain and accordingly TTF_r48 gene is predicted to be a transcription factor.

(TTF_r49 Gene)

A full-length cDNA of TTF_r49 gene was obtained from a cDNA clone library that the applicant has. TTF_r49 gene was selected as a gene whose expression was suppressed by jasmonate treatment in the microarray analysis as described in Example 3. A base sequence of this full-length cDNA of TTF_r49 gene is shown in SEQ ID NO: 14. It is inferred that TTF_r49 gene encodes the amino acid sequence of SEQ ID NO: 30. This amino acid sequence has AUX/IAA domain and accordingly TTF_r49 gene is predicted to be a transcription factor.

(TTF_r66 Gene)

A full-length cDNA of TTF_r66 gene was obtained from a cDNA clone library that the applicant has. TTF_r66 gene was selected in Example 4 as a gene related to an amino acid sequence having ethylene as a keyword. A base sequence of this full-length cDNA of TTF_r66 gene is shown in SEQ ID NO: 15. No clear ORF is found in the base sequence of TTF_r66 gene.

(TTF_r84 Gene)

A full-length cDNA of TTF_r84 gene was obtained from a cDNA clone library that the applicant has. TTF_r84 gene was selected by using QPT1 Bait sequence in Example 5. A base sequence of the full-length cDNA of TTF_r84 gene is shown in SEQ ID NO: 16. It is inferred that TTF_r84 gene encodes the amino acid sequence of SEQ ID NO: 31. In this amino acid sequence, no conserved domain structure is found.

(TTF_r86 Gene)

A full-length cDNA of TTF_r86 gene was obtained from a cDNA clone library that the applicant has. TTF_r86 gene was selected by using PMT1 Bait sequence in Example 5. A base sequence of the full-length cDNA of TTF_r86 gene is shown in SEQ ID NO: 17. It is inferred that TTF_r86 gene encodes the amino acid sequence of SEQ ID NO: 32. This amino acid sequence has a conserved domain structure of Cytochrome c oxidase subunit VIa.

Note that names of the domains of the amino acid sequences are described in Conserved Domain Database (CDD) of NCBI.

Example 8

Modification of Component in Transformed Plant

A transformed plant was prepared by introducing an RNAi construct or an overexpression construct. Then, a change in components in thus prepared transformed plant was checked as below.

(Construction of Constructs)

A vector used for RNAi was pSP231 into which GFP expression cassette was inserted into SacI site of pHellsgate12 (Non-Patent Literature: Wesley et al., 2001, Plant J., 27, 581-590) that was a Gateway (Registered Trademark) vector.

The entry clone of Example 6 was used for RNAi construct of TTF_#53 gene, TTF_#54 gene, TTF_#55 gene, TTF_#56 gene, TTF_#80 gene, TTF_#84 gene, TTF_r33 gene, TTF_r35 gene, TTF_r40 gene, TTF_r48 gene, TTF_r49 gene, TTF_r66 gene, TTF_r84 gene, and TTF_r86 gene. For preparing RNAi construct of TTF_#20 gene, TTF_r20 gene, TTF_r25 gene, or NtPMT1 gene, a DNA fragment (SEQ ID NO: 122 (TTF_#20), SEQ ID NO: 123 (TTF_r20), SEQ ID NO: 124 (TTF_r25), or SEQ ID NO: 125 (PMT1)) was obtained by PCR amplification with use of primers shown in Table 4. Then, this DNA fragment was inserted into pENTR/D-TOPO vector and thereby an entry clone was obtained. By using this entry clone, the RNAi construct above was prepared. Note that the PCR amplification and cloning of the DNA fragment were carried out by the procedures described in Example 6. Further, note that a plasmid obtained form a full-length cDNA clone library that the applicant has was used as a template in the PCR amplification.

TABLE 4

| PRIMER NAME | SEQUENCE (SEQ ID NO) |
| --- | --- |
| TTF_#20_triger_F2 | CACCTACGACATGGAAGTGGCTTTCAGA (SEQ ID NO: 114) |
| TTF_#20_triger_R2 | GCCTTATCTTTGCTCAAGATTTTGG (SEQ ID NO: 115) |
| TTF_r20_triger_F2 | CACCTGACTATGAAGAAAGTCTGAG (SEQ ID NO: 116) |
| TTF_r20_triger_R2 | GGCTTTAATTGAATAACTTCATAAAATGAATCG (SEQ ID NO: 117) |
| TTF_r25_triger_F2 | CACCATTGTCTCCACATTTGCCTTA (SEQ ID NO: 118) |
| TTF_r25_triger_R2 | GAAAAGAATTCAAGACTCAAAGACACCC (SEQ ID NO: 119) |
| NtPMT1_D_TOPO_F | CACCTCAACGGCTACCAGAATGGC (SEQ ID NO: 120) |
| NtPMT1_D_TOPO_R | CCACCATTCTCTGTATGTTGAATTGCTCC (SEQ ID NO: 121) |

The DNA fragment contained in the entry clone was inserted into pSP231 that was a Gateway (Registered Trademark) RNAi vector by using LR clonase (Invitrogen Corporation). Thus constructed RNAi construct was purified from E. coli by using QIAprep Spin MiniprepKit (QIAGEN) and further introduced into Agrobacterium strain LBA4404 (Non-Patent Literature Hoekema et al., 1983, Nature, 303, 179-180) by the electroporation method. Note that for use as a positive control of decrease in nicotine content, an RNAi construct of NtPMT1 was prepared. Further, for producing a transformed plant that was to be a positive control of increase in nicotine content, an overexpression construct of NtPMT1 gene was prepared. As a transformation vector for overexpression, pRI201-AN (Takarabio Inc.) was used. The DNA fragment to be inserted into the transformation vector was obtained by (i) obtaining a DNA fragment (SEQ ID NO: 128) amplified by PCR by use of a forward primer having PshBI restriction enzyme recognition site and a reverse primer having SalI restriction enzyme recognition site which are shown in Table 5 and (ii) performing double digestion of thus obtained DNA fragment at NdeI and SalI. Thus obtained product of the double digestion was inserted at the NdeI/SalI site in a multiple cloning site of pRI201-AN. Thereby, the overexpression construct of NtPMT1 gene was obtained.

TABLE 5

| PRIMER NAME | SEQUENCE (SEQ ID NO) |
|---|---|
| pmt_oe_f | GCGATTAATGGAAGTCATATCTACCAACACAAATGGC (SEQ ID NO: 126) |
| pmt_oe_r | CGTGGTCGACTTAAGACTCGATCATACTTCTGGCG (SEQ ID NO: 127) |

(Preparation of Transformed Plant)

From a tobacco variety SR-1 cultivated for approximately 1.5 month in a greenhouse, an expanded top leaf was picked. Then, a surface of this leaf was disinfected for approximately 5 minutes with sodium hypochlorite solution (which contains available chlorine by 1% and to which several drops of Tween 20 were added per liter) and washed three times with sterile water. Further, by using a surgical knife, an approximately 5 mm square leaf segment was prepared from the leaf whose surface was disinfected. The leaf segment and Agrobacterium (approximately $10^8$ cells) containing a transformation construct were co-cultured for 48 hours on Murashige and Skoog medium (MS medium, Non-Patent Literature Physiol. Plant, 1962, 18, 100-127) containing 30 g/L sucrose. Subsequently, the leaf segment was washed three times with sterile water containing 250 mg/L cefotaxime so that bacteria was washed off. Then, the leaf segment was placed on an MS medium (pH 5.8) containing 30 g/L sucrose, 0.3 mg/L indole acetate, 10 mg/L 6-(γ,γ-dimethylallyl-amino)purine, 100 mg/L kanamycin, 250 mg/L cefotaxime, and 0.3% gellan gum. Approximately 2 weeks after the start of culturing on the MS medium, a callus-like cellular mass showing resistance to kanamycin was obtained. This callus-like cellular mass was placed on a ½ MS medium (pH 5.8) containing 15 g/L sucrose, 100 mg/L kanamycin, 250 mg/L cefotaxime and 0.3% gellan gum. Consequently, a redifferentiated individual was obtained.

Then, a transformed plant (T0 generation) into which a target construct was introduced was selected by GFP fluorescence. Approximately three months after the co-culture, thus selected transformed plant was transplanted into a 12 cm terracotta pot having a diameter of 124 mm, and cultivated in a closed system greenhouse whose temperature was regulated at approximately 23° C. Further, approximately 2.5 months after potting, pollen was collected from the transformed plant (T0 generation) and used for pollination with wild-type SR-1. Thereby, a seed of F1 hybrid was obtained.

(Cultivation of Transformed Plant)

Cultivation of F1 plants was carried out by using a phytotron (day length of 8 hours, illuminance: approximately 30000 1x, temperature: 26° C. (light period)/18° C. (dark period), and relative humidity: 60% (light period)/80% (dark period)).

Seeds of the F1 plants and SR-1 were sowed in rich soil for seeding (Supermix A, Sakata Seed Co.) and germinated by bottom irrigation. Then, 18 days after the seeding, seedlings germinated were temporarily planted. Further, 13 days after the temporary planting, the seedlings were transplanted into 12 cm terracotta pots. Note that approximately 4 weeks after the seeding, a leaf disc was taken from a leaf of each of the F1 plants and GFP fluorescence was observed. Thereby, transformed plants F1 each having a transgene were selected. Ultimately, 3 or 4 individuals for each line of the transformed plants F1 were selected and provided for the following experiment. Similarly, 5 or 6 individuals of SR-1 that was a control plant were provided for the experiment.

Thirteen days after the transplant, first to fourth leaves from the bottom were removed from the transformed plants F1 and the wild-type plants. On some of individuals, topping was carried out by leaving up to 7th leaves from the bottom. From the individuals subjected to topping, an auxiliary bud extending from each leaf axil was removed as appropriate. On individuals having not been subjected to topping, auxiliary buds were left as they were.

Twenty days after the transplant (7 days after the topping), all leaves of the individuals having been subjected to topping were picked. Further, from the individuals having not been subjected to topping, leaves (5th to 7th leaves) at the same stalk positions as the leaves picked from the individuals having been subjected to topping were picked. From thus picked leaves, mid-rib was removed. Then, the picked leaves were immediately frozen by using liquid nitrogen and stored at −80° C. Subsequently, the leaves frozen were freeze-dried, and then ground by using Multi Beads Shocker (Yasui Kiki Corporation).

(Measurement of Nicotine Content)

Analysis of nicotine contents in the transformed plants was carried out in the same manner as in Example 6. Table 6 shows, as a nicotine content ratio of each transformed plants F1 to the control, an influence of the transformation onto the nicotine content. As compared to the control plant, increase in leaf nicotine content was observed in the transformed plants F1 into which the RNAi constructs of the following genes had been introduced: TTF_#20 gene, TTF_#53 gene, TTF_#54 gene, TTF_#55 gene, TTF_r33 gene, TTF_r40 gene, TTF_r48 gene, and TTF_r66 gene. That is, RNA interference of these genes increased the nicotine contents of tobacco plants as in a case of the TRV assay of Example 6. Further, in each transformed plant F1 into which RNAi construct of TTF_#80 gene, TTF_#84 gene, or TTF_r86 gene was introduced, the leaf nicotine content was decreased as compared to the control plant. That is, the RNA interference of these genes decreased the nicotine contents of tobacco plants as in the case of the TRV assay.

TABLE 6

| RNAi CONSTRUCT | TRANSFORMATION LINE | NICOTINE CONTENT (RATIO TO CONTROL) | |
|---|---|---|---|
| | | CASE WHERE TOPPING WAS CARRIED OUT | CASE WHERE TOPPING WAS NOT CARRIED OUT |
| TTF_#20 | 1 | 134% | 105% |
| | 2 | 124% | 105% |
| | 3 | 110% | 104% |
| TTF_#53 | 1 | 155%* | 96% |
| | 2 | 123% | 108% |
| | 3 | 132%* | 115% |
| TTF_#54 | 1 | 121% | 99% |
| | 2 | 129%** | 106% |
| | 3 | 110% | 98% |
| TTF_#55 | 1 | 121% | 93% |
| | 2 | 139%* | 103% |
| | 3 | 123%* | 120% |
| TTF_#56 | 1 | 109% | 81%** |
| | 2 | 102% | 92% |
| | 3 | 113% | 72%** |
| TTF_#80 | 1 | 62%** | 69%** |
| | 2 | 16%** | 10%** |
| TTF_#84 | 1 | 2%** | 6%** |
| | 2 | 5%** | 1%** |
| | 3 | 1%** | 4%** |
| TTF_r20 | 1 | 100% | 100% |
| | 2 | 89% | 90% |
| | 3 | 101% | 99% |
| TTF_r25 | 1 | 99% | 124% |
| | 2 | 105% | 110% |
| | 3 | 101% | 104% |
| TTF_r33 | 1 | 101% | 86% |
| | 2 | 134%** | 123%** |
| | 3 | 123%** | 109% |
| TTF_r35 | 1 | 75%** | 101% |
| | 2 | 76%** | 77% |
| | 3 | 71%** | 108% |
| TTF_r40 | 1 | 139%** | 114%* |
| | 2 | 117% | 111%* |
| TTF_r48 | 1 | 136%** | 143%** |
| | 2 | 156%** | 117%** |
| | 3 | 196%** | 129%** |
| TTF_r49 | 1 | 124%* | 133%** |
| | 2 | 122%* | 111% |
| TTF_r66 | 1 | 94% | 131%* |
| | 2 | 99% | 134% |
| TTF_r84 | 1 | 98% | 105% |
| | 2 | 106% | 102% |
| | 3 | 113% | 101% |
| TTF_r86 | 1 | 85%** | 115% |
| | 2 | 85%** | 121%* |

**SIGNIFICANTLY DIFFERENT VALUE AT SIGNIFICANCE LEVEL OF 1%
*SIGNIFICANTLY DIFFERENT VALUE AT SIGNIFICANCE LEVEL OF 5%

TABLE 7

| CONTROL CONSTRUCT | TRANSFORMATION LINE | NICOTINE CONTENT (RATIO TO CONTROL) | |
|---|---|---|---|
| | | CASE WHERE TOPPING WAS CARRIED OUT | CASE WHERE TOPPING WAS NOT CARRIED OUT |
| NtPMT1_RNAi | 1 | 3%** | 7%** |
| | 2 | 3%** | 7%** |
| NtPMT OVEREXPRESSION | 1 | 96% | 140%** |
| | 2 | 95% | 148%** |
| | 3 | 104% | 107% |

Meanwhile, influence of RNA interference of TTF_#56 gene, TTF_r35 gene, and TTF_r49 gene was different from that in the case of TRV assay. That is, the RNA interference of TTF_#56 gene decreased leaf nicotine content of tobacco having not been subjected to the topping. The RNA interference of TTF_r35 gene decreased leaf nicotine content of tobacco having been subjected to the topping. The RNA interference of TTF_r49 gene increased leaf nicotine content of tobacco regardless of whether or not the topping had been carried out.

The RNAi constructs of TTF_#80 and TTF_#84 significantly decreased leaf nicotine content in the same manner as the RNAi construct of NtPMT1 gene that was used as a positive control of decrease in nicotine content. Meanwhile, the RNAi constructs of TTF_r35 gene and TTF_r86 gene significantly decreased leaf nicotine content by 15% to 29%. Further, the overexpression construct of NtPMT1 gene that was used as a positive control of increase in nicotine content increased leaf nicotine content of tobacco that had not been subjected to the topping. However, this overexpression construct did not affect leaf nicotine content of tobacco having been subjected to topping in accordance with an actual tobacco cultivation method.

As described above, some of the RNAi constructs of the genes of the present invention decreased or increased leaf nicotine content of tobacco plants. Conventionally, an example in which nicotine content is drastically decreased has been known. However, an example in which nicotine content is moderately decreased has not been known. Such an example of moderate decrease was realized by the cases of the RNAi constructs of TTF_r35 gene and TTF_r86 gene of the present invention. Further, there has been no known example of a stably transformed plant, like some of the transformed plants of the present invention, having leaf nicotine content increased by introduction of a construct suppressing gene expression. Furthermore, there has been no known example in which increase in nicotine content is checked in comparison of stably transformed tobacco and a control, by using individuals having been subjected to topping in a manner that is generally performed in actual tobacco cultivation.

Note that Shoji et al. found that there are at least 7 types of ERF genes present at NIC2 locus that had been considered as one of a master switch for alkaloid synthesis. Further, Shoji et al. report a transformed tobacco hairy roots (variety: Petit Havana SR1) whose alkaloid content is significantly decreased by overexpression of ERF189 and ERF179 caused by connecting EAR motif to ERF189 and ERF179 (Non-Patent Literature: Shoji et al, 2010, Plant Cell., 22, 3390-409). ERF189 and ERF179 are among the 7 types of ERF genes described above. Furthermore, Shoji et al. successfully improves the alkaloid content in roots of a nic (niclnic2) mutant line having a genetic background of a variety NC 95, by overexpression of ERF189 and ERF115.

(LC-TOF/MS Analysis)

As described in the section of Cultivation of Transformed Plant, freeze-dried powders of leaves was prepared. The leaves were picked from individuals of the control plant and the transformed plants F1 to each of which the topping had been carried out. The transformed plants F1 here had been obtained by introduction of RNAi construct of TTF_#53 gene, TTF_#56 gene, TTF_r20 gene, TTF_r25 gene, TTF_r84 gene, or TTF_r86 gene. Then, thus prepared freeze-dried powders were provided for LC-TOF/MS analysis. This LC-TOF/MS analysis was entrusted to Genaris, Inc. (Kanagawa, Japan).

The freeze-dried powders of 3 or 4 individuals (regarding the control, 5 or 6 individuals) of one line were mixed to give a sample to be provided for the analysis. An amount of each of the freeze-dried powders mixed was equal. Here, for the analysis, samples of two lines per construct were prepared. Further, from each of the freeze-dried powder samples, an extract to be provided for LC-TOF/MS analysis was obtained as follows. First, to 100 mg of the freeze-dried powders, 1 ml of 50% acetonitrile and 0.5 g of glass beads having Φ1.0 mm were added. Then, disruption was carried out at 4° C. for 5 minutes. Thus obtained disrupted sample solution was subjected to centrifugation (4° C.) for 1 min at 15000 rpm. Then, supernatant was 10-fold diluted. This diluted supernatant solution was subjected to ultrafiltration (molecular weight cut-off: 10,000, 10° C.) and provided as an extract for the LC-TOF/MS analysis. According to need, a sample diluted by 5% acetonitrile solution (water/acetonitrile=95/5) was used for the analysis.

In the analysis, LCT Premier XE/ACQUITY UPLC (Waters Corporation) was used. For separation in UPLC, ACQUITY UPLC T3 column (2.1×50 mm, Waters Corporation) was used and linear gradient elution (for 10 minutes) was carried out by using water/acetonitrile containing 0.1% formic acid. In a mass analysis section, two types of ionization modes of ESI Positive and ESI Negative were used and all peaks in a range of 50 to 1000 m/z were measured.

The following procedures were applied for extraction of peaks at which signal intensity increased or decreased in the transformed plants F1 as compared with the control. First, in the analysis by comparison between the transformed plants F1 and the control, each peak whose signal intensity is greater than 50 in regard to at least one sample was selected a target for analysis, among peaks whose retention time in LC is in a range of 0.3 min to 9.9 min. Though the target for analysis depends on each construct, there were approximately 1700 peaks.

Next, signal intensities of the two lines of the transformed plants F1 were compared with signal intensities of the control. As a result of the comparison, peaks at which the signal intensities of the two lines of the transformed plants F1 were ½ or less or twice or more of the signal intensities of the control were extracted. Table 8 shows the number of peaks extracted. Compounds responsible for the respective peaks are inferred by comparing information such as m/z value and retention time of each peak extracted, with those shown in known compound database or data obtained by analyzing standard compounds. Then, according to thus inferred compounds mapped on KEGG metabolic pathway and the compounds inferred from the data obtained by analyzing standard compounds, the following compounds were inferred as metabolites at the peaks which metabolites were found to increase or decrease in each transformed plant F1.

TABLE 8

NUMBER OF PEAKS EXTRACTED

| RNAi CONSTRUCT | NUMBER OF PEAKS THAT DECREASED BY HALF OR MORE | NUMBER OF PEAKS INCREASED TWICE OR MORE |
| --- | --- | --- |
| TTF_#53 | 21 | 14 |
| TTF_#56 | 37 | 81 |
| TTF_r20 | 31 | 11 |
| TTF_r25 | 14 | 45 |
| TTF_r84 | 78 | 6 |
| TTF_r86 | 52 | 132 |

In the transformed plant F1 into which the RNAi construct of TTF_#53 gene was introduced, anatalline (Pyridinealkaloid biosynthesis) increased. In the transformed plant F1 into which the RNAi construct of TTF_#56 gene was introduced, glutamine, arginine (arginine, proline metabolism), and phenylalanine (phenylalanine metabolism) increased. In the transformed plant F1 into which the RNAi construct of TTF_r20 gene was introduced, no inferred compound that allows inference of a metabolic pathway could be found. In the transformed plant F1 into which the RNAi construct of TTF_r25 gene was introduced, a compound in a naphthalene and anthracene degradation pathway, and a compound in fluorene degradation pathway decreased. In the transformed plant F1 into which the RNAi construct of TTF_r84 gene was introduced, erythronolide B (12-, 14-, 16-macrolide biosynthesis) decreased. In the transformed plant F1 into which the RNAi construct of TTF_r86 gene was introduced, succinic acid, 2-oxoglutaric acid (TCA cycle), and anatalline (Pyridinealkaloid biosynthesis) decreased. As described above, the RNA interference of each gene caused a change in plant leaf component. Therefore, any of TTF_#53 gene, TTF_#56 gene, TTF_r20 gene, TTF_r25 gene, TTF_r84 gene, and TTF_r86 gene has a function of regulating contents of various metabolites.

Example 9

Check Functions of TFF_#80 Gene and TFF_#84 Gene

By performing complementation tests using *E. coli*, respective functions of TFF_#80 gene and TFF_#84 gene were checked.

(Construction of *E. Coli* Expression Construct)

PCR was carried out by (i) using, as primers, #80_F_5-Bam (5'-GGATCCGTGATGGATGCCGCAAAT-3': SEQ ID NO: 129) and #80_F_3-Kpn (5'-GGTACCTTAAGCAGAGCTTGATCGTCC-3': SEQ ID NO: 130) and (ii) using, as a template, plasmid containing a full-length cDNA of TFF_#80 gene obtained from a cDNA clone library that the applicant has. In the PCR, a DNA fragment containing a full-length ORF of TFF_#80 was amplified. Similarly, PCR was carried out by (i) using, as primers, #84_F_5-Bam (5'-GGATCCGTTATGGACGCCGCAAAT-3': SEQ ID NO: 131) and #84_F_3-Kpn (5'-GGTACCTTAAGCGGAGCTTGATCGTTG-3': SEQ ID NO: 132) and (ii) using, as a template, plasmid containing a full-length cDNA of TFF_#84 gene obtained from a cDNA clone library that the applicant has. In the PCR, a DNA fragment containing a full-length ORF of TFF_#84 was amplified. By using 10 μM of each primer and PrimeStarMax (Takarabio Inc.) as enzyme, reaction was carried out according to an attached manual. By introducing an amplified fragment which was digested with both BamHI and KpnI into a BamHI/KpnI site in a multiple cloning site of pQE30 vector (Qiagen), IPTG inducible expression construct was prepared.

Competent cells of Nad deficient *E. coli*: JD26148 transferred from National Institute of Genetics were prepared by a general method, and transformation was carried out by using each of the constructs. Into thus obtained transformed *E. coli*, the expression constructs of TFF_#80 gene and TFF_#84 gene were introduced. These *E. coli* were called #80_pQE3O_JD and #84_pQE3O_JD, respectively.

(Complementation Tests Using *E. Coli*)

Figure 2:
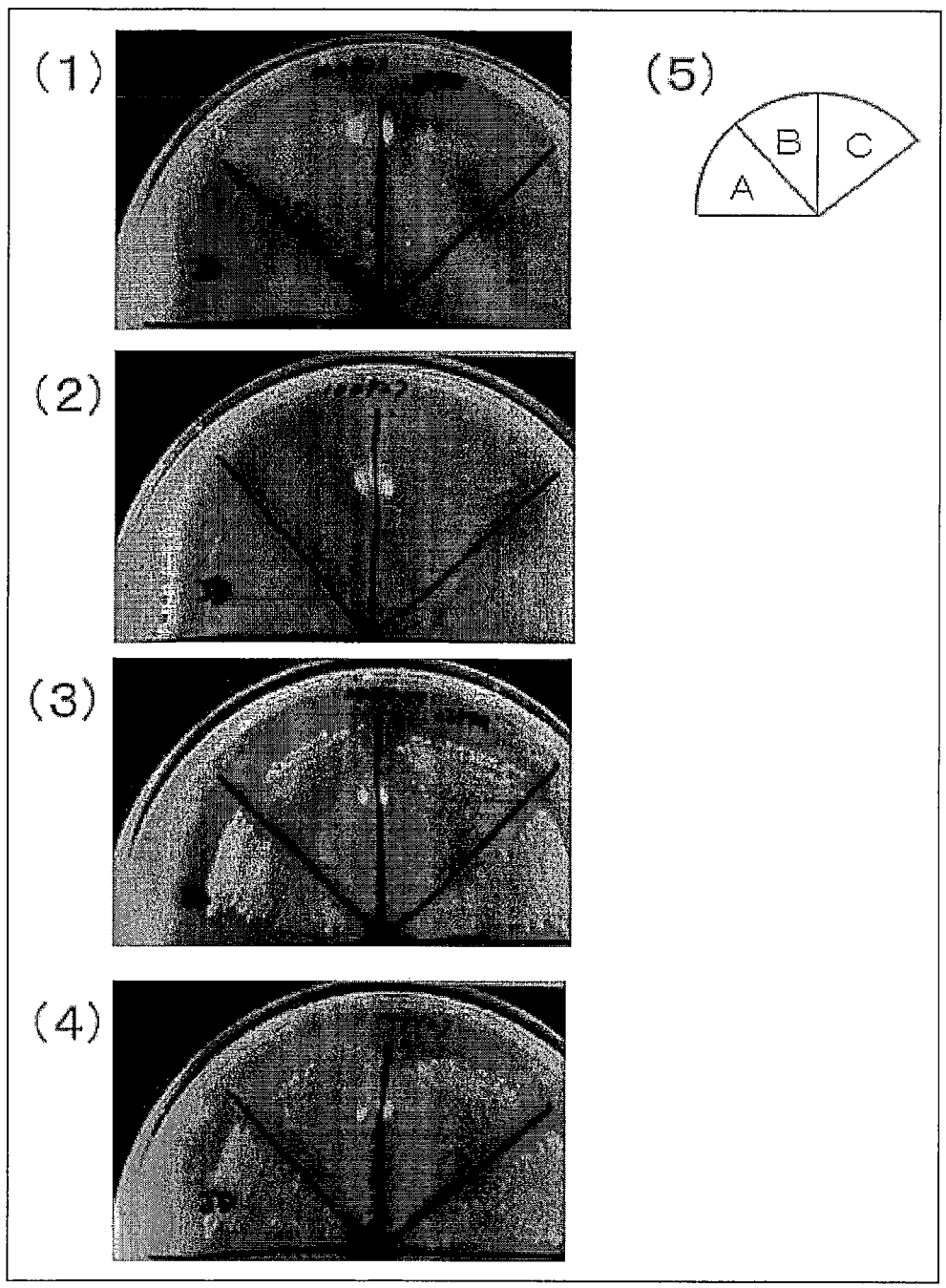
FIG. 2 is a diagram showing a result of complementation tests using *E. coli* on genes of the present invention.

JD26148 (control that had not been transformed), #80_pQE3O_JD and #84_pQE3O_JD were streaked on M9 medium that is a minimum medium, M9+IPTG (1 mM) medium, M9+NA (nicotinic acid: 10 μg/ml) medium, and M9+NA+IPTG medium, and then cultured at 37° C. for 4 days. JD26148 was resistant to kanamycin, and accordingly, 25 μg/ml kanamycin was added to the medium. FIG. 2 shows a result of this culture. (1) of FIG. 2 shows a result of the culture using the M9+IPTG medium; (2) of FIG. 2 shows a result of the culture using the M9 medium; (3) of FIG. 2 shows a result of the culture using the M9+NA+IPTG; and (4) of FIG. 2 shows a result of the culture using the M9+NA medium. In addition, (5) of FIG. 2 shows strains of *E. coli* streaked onto each division on the medium shown in (1) to (4) of FIG. 2. JD26148 was streaked in the division corresponding to "A"; #80_pQE3O_JD was streaked in the division corresponding to "B"; and #84_pQE3O_JD was streaked in the division corresponding to "C". As shown in FIG. 2, JD26148 did not grow on the M9 medium, but grew only on the medium containing NA. On the other hand, #80_pQE3O_JD and #84_pQE3O_JD did not grow on the M9 medium, but grew on the M9+IPTG (1 mM) medium that did not contain NA. All of JD26148, #80_pQE3O_JD and #84_pQE3O_JD grew in the presence of NA regardless of the presence of IPTG. Table 9 shows these results. JD26148 became capable of growing by expression of the full-length ORF of TFF_#80 gene or TFF_#84 gene. Therefore, it was inferred that TFF_#80 gene and TFF_#84 gene encodes Quinolinate Synthase (QS).

TABLE 9

RESULTS OF COMPLEMENTATION TESTS

|  | M9 + IPTG | M9 | M9 + NA | M9 + NA + IPTG |
|---|---|---|---|---|
| JD26148 | − | − | + | + |
| #80_pQE30_JD | + | − | + | + |
| #84_pQE30_JD | + | − | + | + |

INDUSTRIAL APPLICABILITY

According to the present invention, a specific metabolite content can be regulated. Therefore, it is possible, for example, to develop leaf tobacco having component that is different in terms of quantity and quality from that in conventional leaf tobacco. This makes it possible to further widen a range of taste and flavor of tobacco products created by blending.

The invention claimed is:

1. An isolated polynucleotide set forth in any one of the following (a) and (b), the isolated polynucleotide having a function of decreasing or increasing a content of a secondary plant metabolite selected from the group consisting of terpenoids, alkaloids, phenolic compounds, and derivatives thereof:
   (a) a polynucleotide consisting of SEQ ID NO:6; and
   (b) a polynucleotide that hybridizes, under a stringent condition, to a polynucleotide consisting of the complementary sequence of the polynucleotide (a), wherein the polynucleotide that hybridizes does not have less than 95% identity to the polynucleotide (a).

2. A vector comprising the isolated polynucleotide as set forth in claim 1.

3. A method for producing a transformed plant whose content of a secondary plant metabolite is decreased or increased, the method comprising the steps of transforming a plant cell by using the vector as set forth in claim 2, and reproducing a plant body from the transformed cell.

4. A transformed plant whose content of a secondary plant metabolite is decreased or increased, the transformed plant being produced by using the vector as set forth in claim 2.

5. A tobacco product produced by using a plant body of the transformed plant as set forth in claim 4, the transformed plant being *Nicotiana tabacum* or *Nicotiana rustica*, wherein the tobacco product comprises the isolated polynucleotide.

6. A vector comprising an isolated polynucleotide, the isolated polynucleotide having a function of decreasing or increasing content of a secondary plant metabolite selected from the group consisting of terpenoids, alkaloids, phenolic compounds, and derivatives thereof; and encoding a polypeptide consisting of the amino acid sequence of SEQ ID NO:22.

7. A method for producing a transformed plant whose content of a secondary plant metabolite is decreased or increased, the method comprising the steps of transforming a plant cell by using the vector as set forth in claim 6, and reproducing a plant body from the transformed cell.

8. A transformed plant whose content of secondary plant metabolite is decreased or increased, the transformed plant being produced by using the vector as set forth in claim 6.

9. A tobacco product produced by using a plant body of the transformed plant as set forth in claim 8, the transformed plant being *Nicotiana tabacum* or *Nicotiana rustica*, wherein the tobacco product comprises the vector encoding SEQ ID NO: 22.

* * * * *